(12) United States Patent
Dierenbach

(10) Patent No.: US 10,507,137 B2
(45) Date of Patent: Dec. 17, 2019

(54) TACTILE INTERFACE SYSTEM

(71) Applicant: Karl Allen Dierenbach, Centennial, CO (US)

(72) Inventor: Karl Allen Dierenbach, Centennial, CO (US)

( * ) Notice: Subject to any disclaimer, the term of this patent is extended or adjusted under 35 U.S.C. 154(b) by 138 days.

(21) Appl. No.: 15/825,099

(22) Filed: Nov. 28, 2017

(65) Prior Publication Data
US 2018/0078422 A1    Mar. 22, 2018

Related U.S. Application Data

(60) Provisional application No. 62/447,001, filed on Jan. 17, 2017.

(51) Int. Cl.
*A61F 11/04* (2006.01)
*H04R 25/00* (2006.01)

(52) U.S. Cl.
CPC .......... *A61F 11/045* (2013.01); *H04R 25/402* (2013.01); *H04R 25/405* (2013.01); *H04R 2225/025* (2013.01)

(58) Field of Classification Search
CPC ... A61F 11/045; A63F 13/285; H04R 25/405; H04R 25/402; H04R 5/033; H04R 2420/07; H04R 2225/021; H04R 25/407; H04R 2225/025
USPC ......................................................... 381/326
See application file for complete search history.

(56) References Cited

U.S. PATENT DOCUMENTS

| | | | |
|---|---|---|---|
| 4,319,081 A * | 3/1982 | Martin | G01H 3/12 340/407.1 |
| 4,354,064 A | 10/1982 | Scott | |
| 4,581,491 A | 4/1986 | Boothroyd | |
| 4,791,620 A | 12/1988 | Leysieffer et al. | |
| 5,035,242 A | 7/1991 | Franklin et al. | |
| 5,870,481 A | 2/1999 | Dymond et al. | |
| 7,251,336 B2 | 7/2007 | Amiri et al. | |
| 7,386,141 B2 * | 6/2008 | Beimel | H04R 25/407 381/312 |

(Continued)

FOREIGN PATENT DOCUMENTS

KR          20100004642 A          1/2010

OTHER PUBLICATIONS

Weisenberger, Janet M. et al., "Development and preliminary evaluation of an earmold sound-to-tactile aid for the hearing-impaired," The Journal of Rehabilitation Research and Development, Feb. 1987, pp. 51-66, vol. 24 No. 2, United States Department of Veterans Affairs, US.

(Continued)

*Primary Examiner* — Oyesola C Ojo

(57) ABSTRACT

A system for indicating a direction to a user is disclosed. The system may include a first unit and a second unit to be worn proximate to a first ear and a second ear of the user respectively. The system may indicate a direction to the user through tactile sensations delivered proximate to the ears of the user by the first and second units. The system may also include microphones to aid in determining the direction of a source of a sound and the system may indicate the determined direction, thereby allowing the user to localize the sound. The system may also function as hearing aids. The system may aid individuals with hearing disabilities by alerting them to the direction of the source of a sound.

18 Claims, 25 Drawing Sheets

(56) References Cited

U.S. PATENT DOCUMENTS

| | | |
|---|---|---|
| 7,571,018 B2 | 8/2009 | Roth et al. |
| 8,289,159 B2 | 10/2012 | Julian et al. |
| 8,494,507 B1 * | 7/2013 | Tedesco ............... A61F 4/00 |
| | | 434/112 |
| 8,526,647 B2 | 9/2013 | Pedersen et al. |
| 8,611,565 B2 | 12/2013 | Currano et al. |
| 8,638,960 B2 | 1/2014 | Gran et al. |
| 9,100,762 B2 | 8/2015 | Gran |
| 9,124,983 B2 | 9/2015 | Recker et al. |
| 9,148,733 B2 | 9/2015 | Gran et al. |
| 9,148,735 B2 | 9/2015 | Ma et al. |
| 9,167,358 B2 | 10/2015 | Fischer |
| 9,338,561 B2 | 5/2016 | Gran et al. |
| 9,432,778 B2 | 8/2016 | Ma |
| 9,584,933 B2 | 2/2017 | Recker et al. |
| 2007/0041595 A1 * | 2/2007 | Carazo ............... H04R 17/00 |
| | | 381/151 |
| 2010/0303267 A1 * | 12/2010 | Pedersen ............ H04R 25/407 |
| | | 381/313 |
| 2011/0019846 A1 * | 1/2011 | Anderson ............ A61B 5/121 |
| | | 381/313 |
| 2014/0146988 A1 * | 5/2014 | Lee ................. H04R 25/554 |
| | | 381/315 |
| 2014/0321662 A1 * | 10/2014 | Kihm ................. H04R 5/0335 |
| | | 381/74 |
| 2015/0098575 A1 * | 4/2015 | Kulavik ............... H04R 29/00 |
| | | 381/56 |
| 2015/0156595 A1 | 6/2015 | Zhong et al. |
| 2015/0230036 A1 * | 8/2015 | Pedersen ............ H04R 1/1041 |
| | | 381/330 |
| 2017/0085998 A1 * | 3/2017 | Fritsch ............... H04R 25/505 |
| 2017/0180863 A1 * | 6/2017 | Biggs ................. B06B 1/045 |
| 2018/0139533 A1 * | 5/2018 | Jain ................. H04R 1/1008 |

OTHER PUBLICATIONS

Hara, E. H., "Alternative paths to hearing a (conjecture). Photonic and tactile hearing systems displaying the frequency spectrum of sound," Applied Bionics and Biomechanics, Jan. 2006, pp. 61-66, vol. 3 No. 1, Hindawi Publishing Corp., Cairo, Egypt.

Byrne, Dennis et al, "Optimizing Sound Localization with Hearing Aids," Trends in Amplification, Jun. 1998, pp. 51-73, vol. 3(2), Sage Publications, California, US.

* cited by examiner

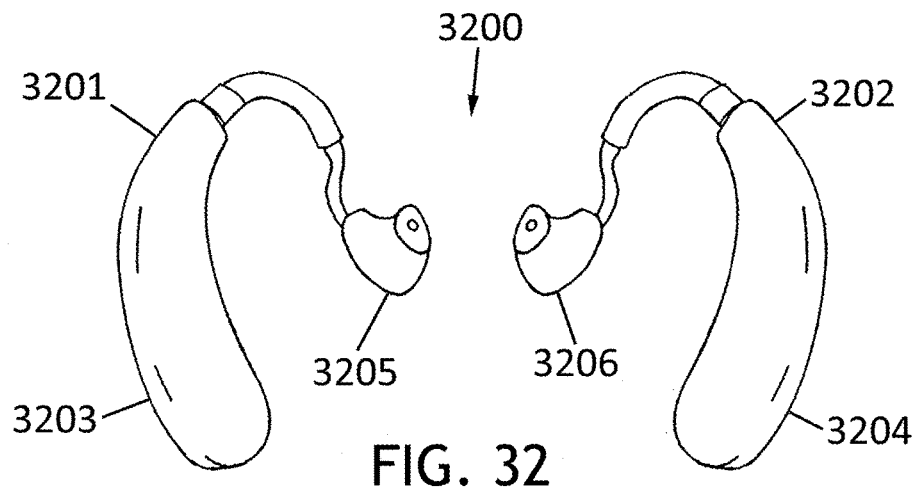
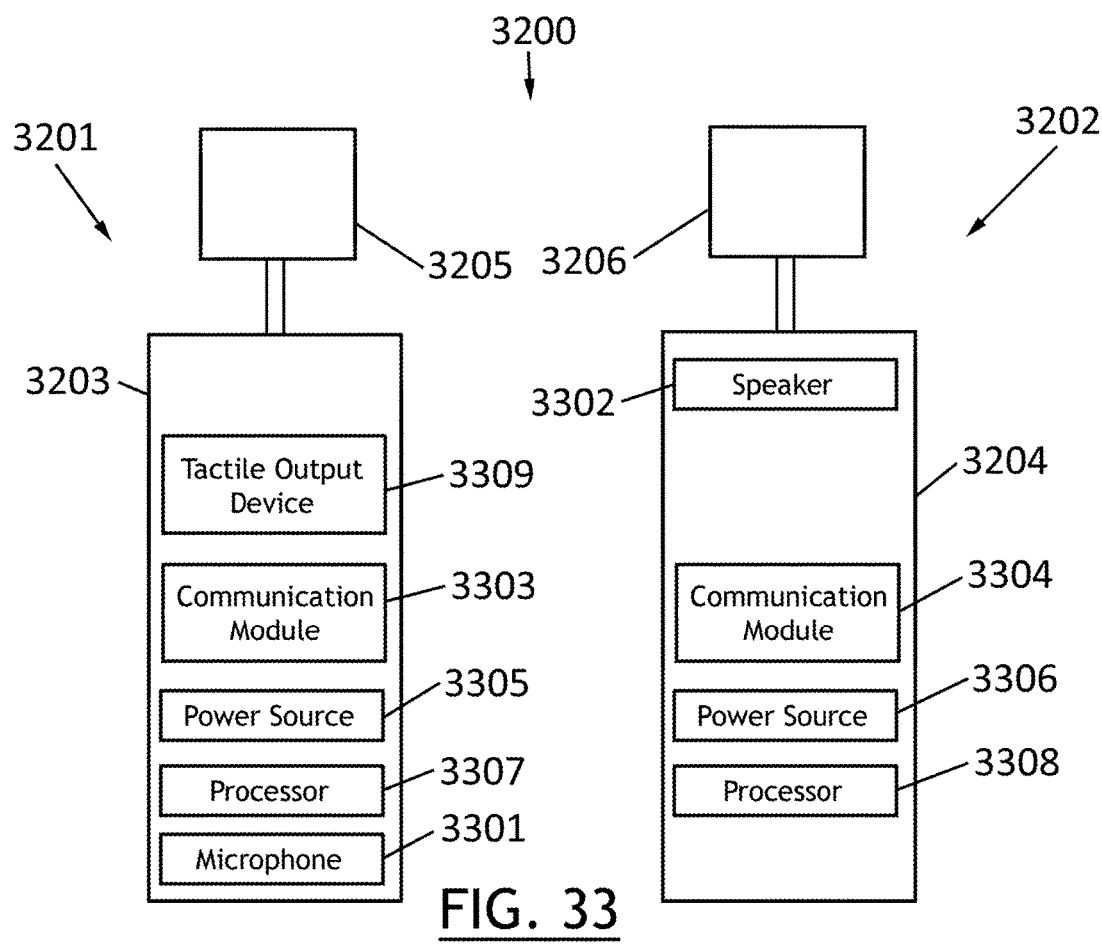

TACTILE INTERFACE SYSTEM

CROSS-REFERENCE TO RELATED APPLICATIONS

This application claims priority to prior U.S. Provisional Patent Application Ser. No. 62/447,001, filed Jan. 17, 2017, titled "Tactile Interface System," the entirety of which is hereby incorporated by reference.

FIELD OF THE INVENTION

The present invention relates to devices designed to improve the understanding of an individual's surroundings, specifically to provide individuals with information through tactile sensations. The information may include directional information, such as the localization of a sound source for an individual with hearing disabilities.

BACKGROUND OF THE INVENTION

An integral part of human sensory capability is the ability to localize sound sources. For example, the ability to localize sound sources allows for improved communication and increased safety. Communication may be improved, for example, by distinguishing sound sources by their location and by using location information to turn toward a person who is talking. Safety may be enhanced, for example, by localization in that an approaching hazard, such as an approaching car or animal, may be located before it becomes an imminent danger.

The human auditory system's ability to localize sound is believed to be based on several aspects of how sound reaches the left and right ears of the listener. Among these aspects are interaural time differences (ITD), interaural phase differences (IPD), and interaural level differences (ILD). The way in which a listener's head, shoulders, and ears filter sounds in a location and frequency dependent manner is referred to as the head-related transfer function (HRTF). The ability of a listener to localize sound by interpreting the HRTF is believed to be a learned response.

There are several situations where humans may suffer from reduced localization capability or completely lose their ability to localize sound sources. One such situation is complete loss of hearing in both ears. In such individuals, no sounds can be heard, and thus no unaided localization can occur.

Another situation is Single-Sided Deafness (SSD), where an individual suffers from complete hearing loss in one ear while retaining some level of hearing in the other ear. These individuals generally are unable to locate the source direction of a sound without some auxiliary information. Such auxiliary information may include visual cues and/or listening during physical movement. For example, a person with SSD may move around and make sound source estimations based on the strength of the sound being heard while in various locations or while facing various directions. However, such localization requires the sound source to occur over a substantial amount of time to enable the listener to move around. Individuals suffering from unilateral hearing loss (where one ear has some level of hearing loss, while the other ear is normal), may suffer from similar localization deficiencies as individuals with SSD.

Individuals suffering from bilateral hearing loss (where both ears have some level of hearing loss), may also have difficulty in localizing sound sources as compared to people with normal hearing.

Moreover, hearing aid users may have poorer ability to localize sound sources when wearing their hearing aids than without their hearing aids. Hearing aids typically reproduce sound such that the wearer perceives sound sources to be localized inside the head, and as such localization capabilities may be reduced or eliminated.

When the ability to localize sound sources is reduced or lost, individuals may experience greater cognitive loading during conversation, particularly when the conversation is among more than two people. Furthermore, such individuals may be slower to react to environmental dangers as compared to individuals with normal localization capabilities. Moreover, individuals with reduced localization capabilities may find some social activities, such as sports or group activities, more difficult.

SUMMARY OF THE INVENTION

In the following description, the invention is set forth in the context of apparatuses and methods for providing information to a user through tactile input to the user. Embodiments of tactile interface systems include systems to deliver location information, status information, and/or other information to a user through tactile output. The information may be delivered to a user through tactile outputs proximate to one or both ears of the user.

The user may, for example, be an individual who suffers from reduced sound source localization capabilities due to some hearing loss. The user may, for example, be an individual who wears hearing aids in both ears and suffers from reduced localization capabilities while wearing the hearing aids. In another example, the user may be a wearer of a crossover hearing aid system who may benefit from a tactile alert when a fault occurs with the crossover hearing aid system. In yet another example, the user may be an individual wearing headphones and/or a virtual reality head set where sound localization information may enhance the experience, such as playing computer games or watching immersive media. The user may be any other person who may benefit from receiving information, including directional information, through tactile input.

In an embodiment, a direction indication system includes a first unit configured to be worn at a first ear of a user and a second unit configured to be worn at a second ear of the user. The first unit includes a first tactile output device configured to deliver a tactile output to the first ear and a first communication module. The second unit includes a second tactile output device configured to deliver a tactile output to the second ear and a second communication module. The communication modules are configured to communicate with each other and/or other devices. The system further includes a processor configured to cause tactile output from at least one of the first and second tactile output devices indicative of a direction relative to the user.

In one aspect, the first and second units may be configured to be worn behind the ear of a user. In another aspect, the first and second units may be configured to be worn in the ear canal of a user. The communication modules may communicate wirelessly and/or they may be interconnected with wiring.

The tactile outputs may be vibration generating devices. In an aspect, a tactile output at a left ear of the user may indicate a direction to the left side of the head of the user, and a tactile output at a right ear of the user may indicate a direction to the right side of the head of the user. In an aspect, simultaneous tactile outputs at both the left ear and the right ear indicate a direction behind the head of the user.

Frequencies of the tactile outputs may be independent of the frequency of any sound proximate to the direction indication system. In an aspect, the frequency of the tactile outputs may be a function of the elevation of the direction to be indicated relative to the head of the user.

In an aspect, the first unit further comprises a third tactile output device, and the second unit further comprises a fourth tactile output device, and the direction indication system is operable to communicate a three-dimensional direction to the user wearing the direction indication system through tactile outputs.

In another embodiment, a directional information communication system includes a first unit configured to be worn at a first ear of a user and a second unit configured to be worn at a second ear of the user. The first unit includes a first tactile output device and the second unit includes a second tactile output device. The directional information communication system further includes a processor configured to cause tactile output from at least one of the first and second tactile output devices according to directional information received by the directional information communication system.

The directional information communication system is operable to communicate directional information to a user wearing the directional information communication system by causing the first and second tactile output devices to produce tactile output that correspond to the directional information received by the directional information communication system.

In another embodiment, an audio source localization aid system includes a first unit and a second unit. The first and second units are configured to be worn at the ears of a user. The first unit includes a first microphone, a first tactile output device, and a first communication module. The second unit includes a second microphone, a second tactile output device, and a second communication module. The communication modules are configured to communicate with each other. The audio source localization aid system further includes a processor configured to determine source location information of sound received by the audio source localization aid system based on sound received by the first and second microphones. The processor is also configured to cause tactile output from at least one of the first and second tactile output devices according to the determined source location information. In this regard, the audio source localization aid system is operable to communicate source location information to a user wearing the audio source localization aid system by causing the first and second tactile output devices to produce tactile output that correspond to the direction of sound received by the audio source localization aid system.

In an aspect, the audio source localization aid system may be configured for a user with unilateral hearing loss where the second unit transmits to the first unit a data stream representative of sound received by the second microphone and the first unit produces an audio stream according to the data stream.

In another aspect, the first and/or second units may be hearing aids capable of producing amplified audio streams.

In another aspect, the audio source localization aid system includes a third microphone and is able to localize sounds based on sound received by the first, second, and third microphones. In a variation of the current aspect, the audio source localization aid system further includes a fourth microphone and is able to localize sounds based on sound received by the first, second, third, and fourth microphones.

In a variation, the frequency of the tactile output from the tactile output devices may be independent of the frequency of sound received by the audio source localization aid system. In a variation, the frequency of the tactile output devices may be a function of the elevation of the source location relative to the head of the user.

In another embodiment, a crossover hearing aid system includes a first unit and a second unit. The first unit includes a microphone, an audio output device, a tactile output device, and a communication module. The second unit includes a microphone, a tactile output device, and a communication module. The crossover hearing aid system further includes a processor configured to determine source location information of sound received by the hearing aid system based on sound received by the first and second units and to cause tactile output from at least one of the first and second units according to determined source location information. Furthermore, the second unit is operable to transmit a data stream to the first unit that is representative of sound received by the second unit, and the first unit is operable to produce an audio stream according to the data stream.

In another embodiment, a hearing aid system includes a first hearing aid unit and a second hearing aid unit. The first hearing aid unit includes a microphone, an audio output device, a tactile output device, and a communication module. The second hearing aid unit includes a microphone, an audio output device, a tactile output device, and a communication module. The hearing aid system further includes a processor configured to determine source location information of sound received by the hearing aid system based on sound received by the first and second hearing aid units. The processor is also configured to cause tactile output from at least one of the first and second hearing aid units according to the determined source location information. The frequencies of the outputs of the tactile output devices may be independent from the frequency of sound received by the hearing aid system.

In another embodiment, a hearing aid system includes a first unit that includes an audio output device and a first communication module, and a second unit that includes a microphone, a tactile output device, and a second communication module. The communication modules are configured to communicate with each other. The hearing aid system is configured to produce a tactile output by the tactile output device upon the second unit losing communication with the first unit. The hearing aid system may be a crossover hearing aid system.

In another embodiment, headphones include a first unit configured to be worn at a first ear of a user and a second unit configured to be worn at a second ear of the user. The first unit includes a first tactile output device configured to deliver a tactile output to the first ear, and a first speaker configured to deliver a first audio stream. The second unit includes a second tactile output device configured to deliver a tactile output to the second ear. Such headphones may be used, for example, in conjunction with a video game system to provide directional information through tactile outputs. Such headphones may benefit users with SSD and/or users that have difficulty localizing sounds. In a variation, the second unit may include a second speaker configured to deliver a second audio stream. The headphones may be configured such that the first audio stream is the same as the second audio stream, thus the headphones may operate in a mono mode. Alternatively, the headphones may operate in a stereo mode. In another variation, the headphones may further include a processor configured to cause tactile output from at least one of the first and second tactile output devices indicative of a direction relative to the user. In another variation, the processor may be configured to determine the tactile outputs to be produced based on an audio stream provided to the headphones.

In another embodiment, a video game system includes a video game console, a first unit configured to be worn at a first ear of a user, a second unit configured to be worn at a second ear of the user, and a processor. The first unit includes a first tactile output device configured to deliver a tactile output to the first ear. The second unit includes a second tactile output device configured to deliver a tactile output to the second ear. The processor is configured to cause tactile output from at least one of the first and second tactile output devices indicative of a direction relative to the user. Such a system may benefit users with SSD and/or users that have difficulty localizing sounds. This may be achieved by producing tactile outputs simultaneously with particular sounds to indicate a direction associated with those particular sounds. In this regard, a user with SSD may hear particular sounds and also receive information as to the location of the source of those particular sounds, enabling them to receive similar information as a normal hearing user playing in a stereo environment. In a variation, the first unit may include a first speaker configured to deliver a first audio stream, and/or the second unit may include a second speaker configured to deliver a second audio stream. The video game system may be configured such that the first audio stream is the same as the second audio stream, thus the video game system may operate in a mono mode. Alternatively, the video game system may operate in a stereo mode.

In another embodiment, a method for transmitting directional information to a user includes wearing a first unit proximate to the right ear of a user and a second unit proximate to the left ear of the user, then obtaining a direction to be communicated to the user, and then producing a tactile output at at least one of the first unit and the second unit that is representative of the direction to be communicated to the user.

In another embodiment, a method for transmitting sound location information to a user includes receiving an audio event at a first microphone of a first unit being worn by the user proximate to a first ear of the user; receiving the audio event at a second microphone of a second unit being worn by the user proximate to a second ear of the user; calculating a direction of a source of the audio event based on the receiving at the first microphone and the receiving at the second microphone; and producing a tactile output at at least one of the first unit and the second unit that is representative of the calculated direction of the source of the audio event.

In a variation, the current method for transmitting sound location information to a user may include receiving an audio stream by the first unit; transmitting data representative of the audio stream from the first unit to the second unit; and producing an audio output by the second unit according to the transmitted data. In this regard, this variation may include operating as a crossover hearing aid system.

In another variation, the current method for transmitting sound location information to a user may include the first unit and/or the second unit operating as hearing aids.

In another embodiment, a method for operating a hearing aid system includes communicating between a first hearing aid unit and a second hearing aid unit of the hearing aid system, and producing a tactile output at the second hearing aid unit in response to losing communication between the first hearing aid unit and the second hearing aid unit.

In another embodiment, a method for operating a hearing aid system includes: receiving an audio event at a first microphone of a first unit being worn by a user proximate to a first ear of the user; receiving the audio event at a second microphone of a second unit being worn by the user proximate to a second ear of the user; calculating a direction of a source of the audio event based at least in part on the receiving at the first microphone and the receiving at the second microphone; producing a tactile output at at least one of the first unit and the second unit that is representative of the calculated direction of the source of the audio event; and producing amplified sound by at least one of the first unit and the second unit during the first receiving step, second receiving step, calculating step, and producing step.

The systems and methods discussed above may, for example, produce tactile outputs in response to sounds that are: above a predetermined level; a predetermined level above the ambient level of sound at the user; interpreted by the systems and methods as speech; and/or selected from a plurality of preprogrammed sounds.

The tactile output devices discussed above may, for example, be eccentric rotating mass vibration motors, linear resonant actuators, and/or piezoelectric transducers.

Additional aspects and advantages of the present invention will become apparent to one skilled in the art upon consideration of the further description that follows. It should be understood that the detailed description and specific examples are intended for purposes of illustration only and are not intended to limit the scope of the invention. Furthermore, any of the above aspects, arrangements, features and/or embodiments may be combined with any other of the above aspects, arrangements, features and/or embodiments where appropriate.

BRIEF DESCRIPTION OF THE DRAWINGS

FIG. 32 is a perspective view of a crossover hearing aid system that may be worn by a user.

FIG. 33 is a functional block diagram of a crossover hearing aid system that may be worn by a user.

DETAILED DESCRIPTION OF THE INVENTION

Figure 1:
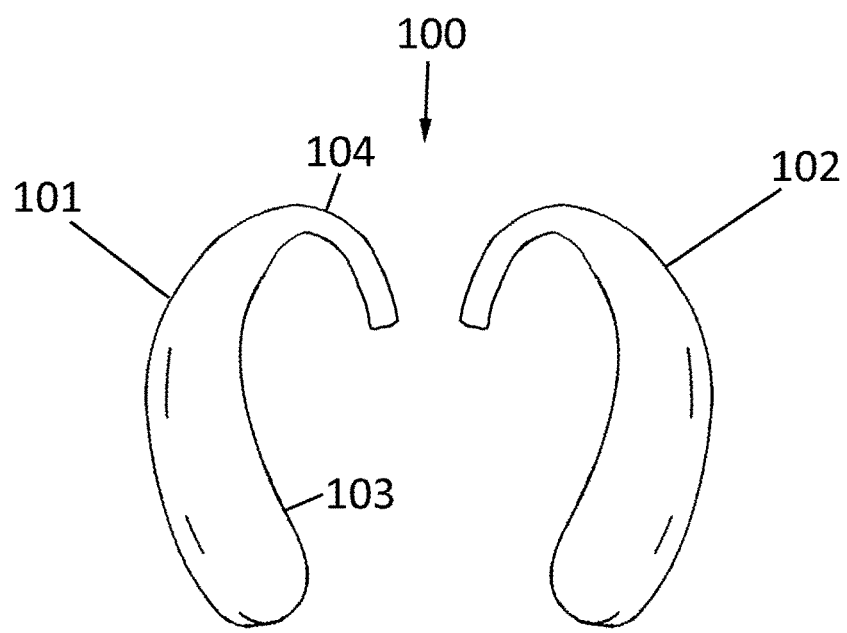
FIG. 1 is a perspective view of a directional indication system that may be worn by a user.

FIG. 1 is an illustration of an embodiment of a directional indication system 100. The directional indication system 100 is operable to indicate a direction to a user. The direction indicated may, for example, correspond to the direction of a sound source relative to the directional indication system 100. In such a scenario, the directional indication system 100 may inform the user of the direction from which a sound is originating. Such an embodiment may be helpful to a user who does not have the ability to localize sound sources, such as an individual who has SSD, unilateral hearing loss, bilateral hearing loss, or is completely deaf.

The direction indicated may, in another example, correspond to the direction of an element in a virtual reality simulation. The directional indication may be part of a game. Such a game may be used to help a user learn to interpret the tactile outputs as directional indications. In another example of the indicated direction being an element in a virtual reality simulation, the indicated direction may be used to indicate the direction from which an attack originated in a video game.

The direction indicated may, in yet another example, correspond to the direction of a teammate, thus allowing team members to know each other's positions without audible communications. Such an embodiment may be useful in military scenarios. In still other embodiments, the directional indication system 100 may indicate the direction of a target to be achieved or a hazard to be avoided.

Figure 2:
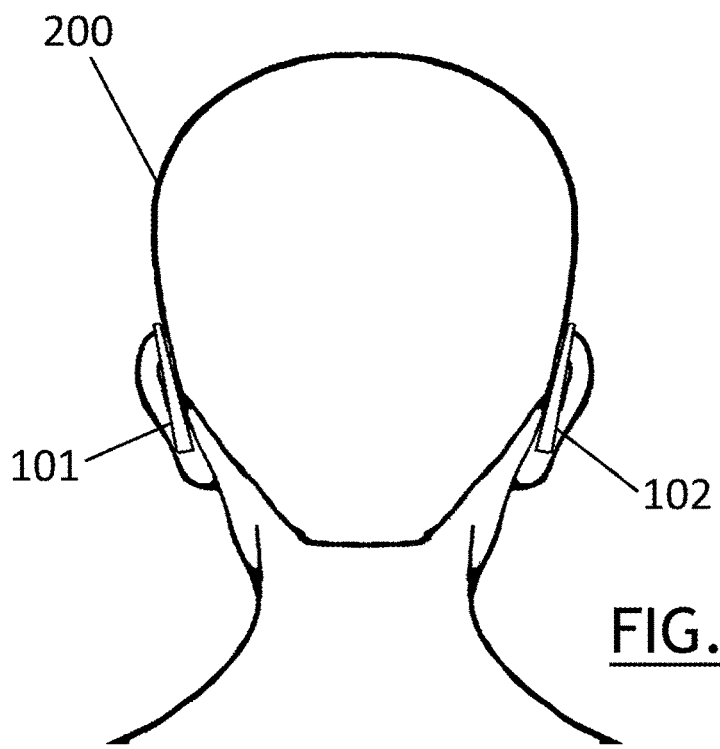
FIG. 2 is a rear view of a user wearing a directional indication system.

The directional indication system 100, shown in FIG. 1, comprises a left unit 101 and a right unit 102. The left and right units 101,102 may be shaped and include features such that the left and right units 101, 102 may be worn behind the left and right ears, respectively, of a user. FIG. 2 illustrates a user 200 wearing the left and right units 101,102.

Returning to FIG. 1, the left and right units 101, 102 may be shaped such that they are capable of being worn behind the ears of a user. In the illustrated embodiment, the left unit 101 includes a thick portion 103 that may house functional elements of the directional indication system 100 discussed below. The left unit 101 also includes a curved portion 104 that is shaped such that it can wrap around the top of the ear to secure the left unit 101 to the user. The right unit 102 is similarly shaped such that it can be worn behind the right ear.

Other configurations and related methods of attaching devices to the ear of a user known to those skilled in the art may be incorporated in the directional indication system 100. For example, a clip capable of attaching to a portion of an ear may be used to secure the left and right units 101, 102 to the ears of a user. In another example, the left and right units 101, 102 may be secured to the ears by portions of the left and right units 101, 102 fitting inside portions of the ears such as proximate to the triangular fossa and/or within the ear canals. Such portions may be custom molded for an individual's ears. In yet another example, the left and right units 101, 102 may be attached to a user's ears in the same fashion as pierced earrings are typically attached. Other examples include attachment to eyeglasses, or configured similar to headphones. Indeed, any appropriate method of attaching devices to and/or positioning devices near the ears of users may be incorporated in the left and right units 101, 102.

Figure 3:
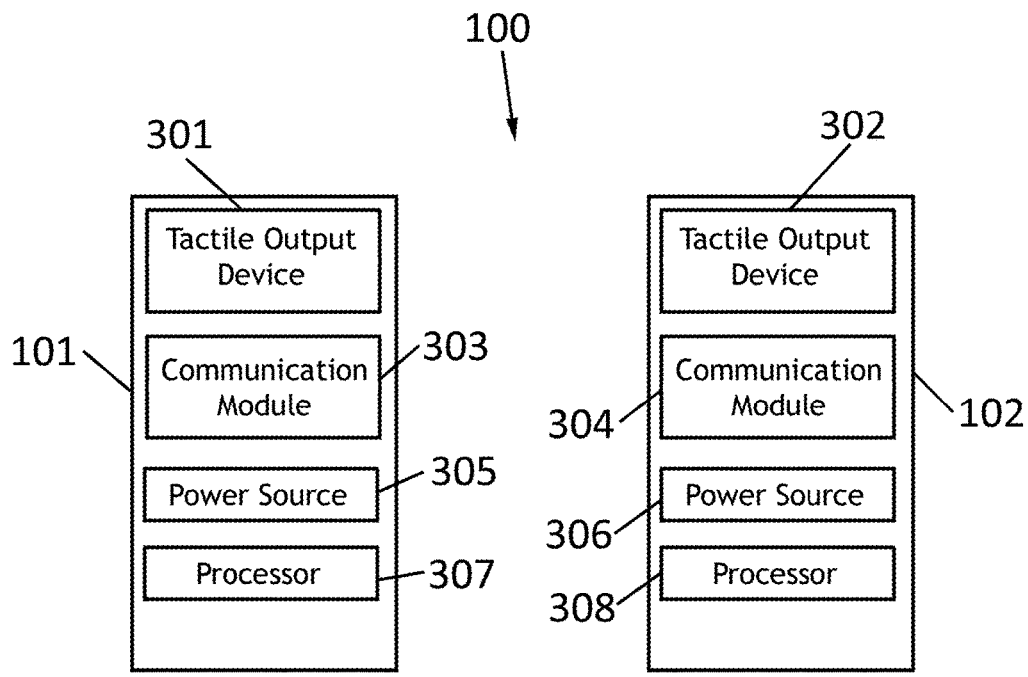
FIG. 3 is a functional block diagram of a directional indication system.

FIG. 3 is a block diagram of the directional indication system 100 depicting internal components of the left and right units 101, 102. The left unit 101 includes a tactile output device 301 and the right unit 102 includes a tactile output device 302. The tactile output devices 301, 302 are capable of independently producing a tactile output that a user wearing the left and right units 101, 102 can feel proximate to the user's left and right ears, respectively.

The tactile output devices 301, 302 may be positioned such that the tactile outputs produced are felt on the pinnae of the user. For example, the tactile output devices 301, 302 may be positioned to stimulate the pinnae of the ears of the user, such as behind the ears and facing the pinnae of the user. The pinna is an advantageous location since it is generally a sensitive area which may enable a user to quickly feel stimulation from the tactile output devices 301, 302.

The tactile output devices 301, 302 may be any appropriate device for producing a physical sensation felt by a user. For example, the tactile output devices 301, 302 may be vibration devices of any appropriate type, such as eccentric rotating mass vibration motors, linear resonant actuators, moving coil transducers, piezoelectric transducers or any combination thereof. The vibration created by each of the tactile output devices 301, 302 may be of any appropriate frequency. The vibrational frequency created by each of the tactile output devices 301, 302 may be selected based upon the ability of a user to consciously or unconsciously interpret the vibrations as an indication of direction. The vibrational frequency may also be selected based upon the comfort of a user. In particular, the vibrational frequency may be between about 100 Hz and 300 Hz to produce a vibration that will feel smooth to the user. The frequency of the output of the tactile output devices 301, 302 may be user adjustable. Such adjustments may be made through, for example, a wireless interface.

Figure 4:
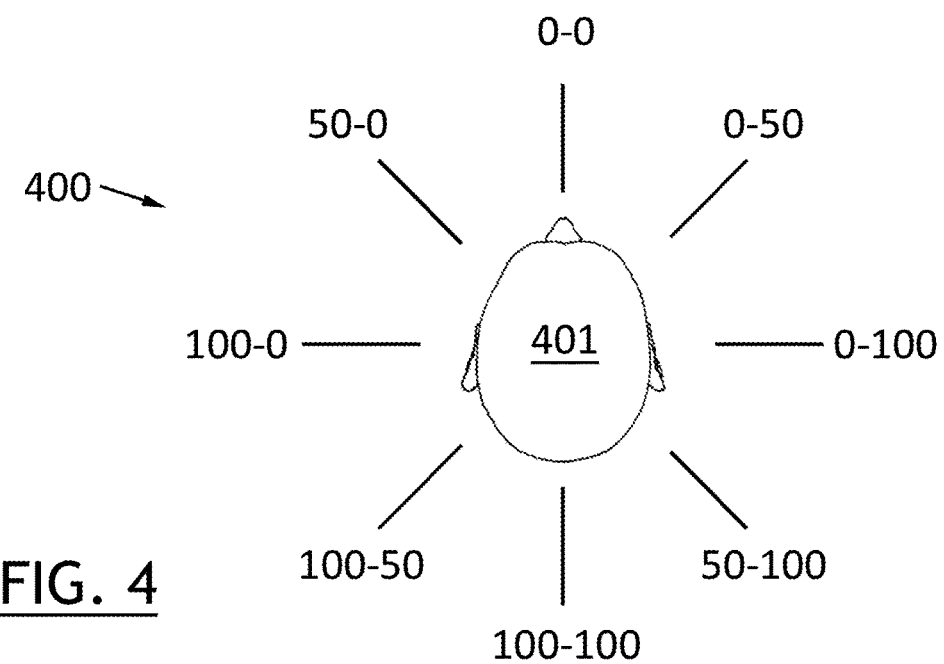
FIG. 4 is a chart indicating output power levels of a directional indication system for various directions within a transverse plane of a user.

The sensations delivered to a user wearing the directional indication system 100 by the tactile output devices 301, 302 may be used to communicate a direction to the user. The indicated direction is relative to the head of the user wearing the directional indication system 100. FIG. 4 is a chart 400 showing how the sensations delivered to the head 401 (viewed from above) of a user by the tactile output devices 301, 302 may be interpreted by the user as indicating a particular direction in the transverse plane of the head 401 of the user. The pairs of numbers positioned about the head 401 indicate the power output (in percentage of maximum set output) for the left tactile output device 301 and the right tactile output device 302, respectively, for that particular direction.

For example, to indicate a direction to the left of the head 401, the left tactile output device 301 would output a vibration at 100% of its maximum set output while the right tactile output device 302 would output no vibration (i.e., 0%). This situation is represented by the "100-0" positioned to the left of the head 401. In another example, to indicate a direction to the right of the head 401, the left tactile output device 301 would output a vibration at 0% of its maximum set output while the right tactile output device 302 would output a vibration at 100% of its maximum set output value. This situation is represented by the "0-100" positioned to the right of the head 401. In this regard, the directional indication system 100 may be used to indicate a left or right direction to the user, and the indicated direction will be relative to the head 401 of the user.

In an additional example, to indicate a direction directly behind the head 401, both the left tactile output device 301 and the right tactile output device 302 would output a vibration at 100% of their maximum set output. Accordingly, when both the left tactile output device 301 and the right tactile output device 302 output a vibration at 100% of their maximum set output, the user knows that the system is indicating a direction directly behind the head 401 of the user. This situation is represented by the "100-100" positioned directly behind head 401.

In the configuration illustrated in FIG. 4, the directional indication system 100 does not output a vibration from either the left tactile output device 301 or the right tactile output device 302 if a source of direction to the directional indication system 100 indicates a direction directly in front of the head 401 of the user. This is because in certain applications, the user may be aware of what is happening directly in front of their head 401 using their sight. For example, in an application where the directional indication system 100 is being used to indicate a direction of a source of a sound to a person with reduced sound localization capabilities (e.g., an individual with SSD), the individual may be aware of the sound through their hearing, and a lack of output from the directional indication system 100 may be interpreted as that sound having a source directly in front of the head 401 of the user. And since that is where the user is facing, the user may quickly be able to ascertain the source of the sound they are hearing through visual information (i.e., they may hear a dog barking and see a dog barking directly in front of them).

For directions not directly in front of, behind, to the left, or to the right of the user, the directional indication system 100 may indicate direction to the user by producing vibration output according to the following formulas, where D is the direction (expressed in degrees) to be indicated to the user with 0 degrees directly in front of the head 401, 90 degrees to the right, 180 degrees behind, and 270 degrees to the left.

Left tactile output device 301 output:

Left tactile output device 301 percentage of maximum output=LO

Direction indicated in degrees=D

For angles from 0 to 90 degrees $$LO=0$$

For angles from 90 to 180 degrees $$LO=((D-90)/90)*100$$

For angles from 180 to 270 degrees $$LO=100$$

For angles from 270 to 360 degrees $$LO=((360-D)/90)*100$$

Right tactile output device 302 output:

Right tactile output device 302 percentage of maximum output=RO

Direction indicated in degrees=D

For angles from 0 to 90 degrees $$RO=(D/90)*100$$

For angles from 90 to 180 degrees $$RO=100$$

For angles from 180 to 270 degrees $$RO=((270-D)/90)*100$$

For angles from 270 to 360 degrees $$RO=0 \qquad \text{Equation Set 1}$$

Thus, according to the above formulas, a direction to be indicated of 45 degrees will result in left tactile output device 301 having an output of 0% and the right tactile output device 302 having an output of 50%. Similarly, a direction to be indicated of 225 degrees will result in left tactile output device 301 having an output of 100% and the right tactile output device 302 having an output of 50%. These scenarios are illustrated in FIG. 4.

It is noted that the formulas described with relation to the outputs shown in FIG. 4 are exemplary and may be modified as appropriate. A feature of the formulas is that every degree of direction around the head 401 of the user is indicated by a unique combination of tactile outputs from the left tactile output device 301 and the right tactile output device 302. Such fine definition may allow a user to determine with high accuracy the direction indicated by the directional indication system 100.

It is further noted that the vibration power is discussed in terms of percentage of maximum set output value. This value represents the highest power level of vibration that the tactile output devices 301, 302 will produce during normal operation. However, this is not necessarily the highest output power that the tactile output devices 301, 302 are capable of producing. For example, the maximum set output value may be set at a value that represents 50% of the maximum power that the tactile output devices 301, 302 are capable of producing. This 50% level would then represent the highest level of output that would be produced during operation by the tactile outputs 301, 302, and therefore would represent 100% of the maximum set output value.

The maximum set output value may be adjustable, for example by an audiologist or the user. This may be beneficial to the user. For example, as a user learns to interpret the tactile outputs of the directional indication system 100, the user may find that he or she is able to understand and interpret indicated direction at a lower maximum set output than originally configured. By lowering the maximum set output, the directional indication system 100 may be able to operate for a longer period of time before needing a recharge or battery replacement. Also, the directional indication system 100 may feel less obtrusive and more holistic at a lower maximum set output.

Figure 5:
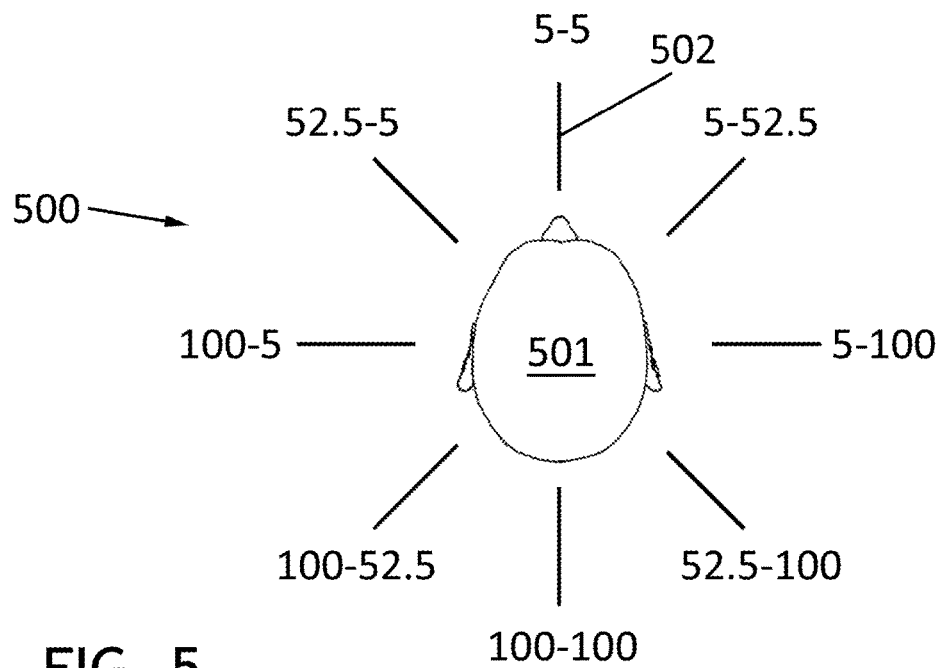
FIG. 5 is a chart indicating alternate output power levels of a directional indication system for various directions within a transverse plane of a user.

In an alternate embodiment illustrated in a chart 500 of FIG. 5, the directional indication system 100 may be configured such that it produces a signal to the user to indicate a direction directly in front of the head 501 of the user. As shown, when both the left tactile output device 301 and the right tactile output device 302 output a vibration at 5% of their maximum set output, this indicates a direction directly in front 502 of the user (0 degrees). Such a configuration may be beneficial since in certain applications, the user may not otherwise be aware of what is happening directly in front of their head 401. For example, in an application where the directional indication system 100 is being used to indicate a direction of a source of a sound to a user who is completely deaf, if the user's eyes are closed, the user may not be aware of another person directly in front of them trying to get their attention verbally. In such a situation, if the other person calls out to the user, information that a sound source is directly in front of the head 501 of the user may be provided to the directional indication system 100, which may in response cause both the left tactile output device 301 and the right tactile output device 302 to output a vibration at 5%, thereby alerting the user that something is in front of them. The user may then open their eyes, see the other person, and start communicating via sign language. In this regard, deaf people may beneficially be informed of the direction of sound sources to help them in communication and increase their awareness of their environment.

Such a configuration may produce vibration output according to the following formulas, where D is the direction (expressed in degrees) to be indicated to the user with 0 degrees directly in front of the head 501, 90 degrees to the right, 180 degrees behind, and 270 degrees to the left.

Left tactile output device 301 output:
Left tactile output device 301 percentage of maximum output=LO
Direction indicated in degrees=D
For angles from 0 to 90 degrees $LO=5$ For angles from 90 to 180 degrees $LO=5+((D-90)/90)*95$ For angles from 180 to 270 degrees $LO=100$ For angles from 270 to 360 degrees $LO=5+((360-D)/90)*95$ Right tactile output device 302 output:
Right tactile output device 302 percentage of maximum output=RO
Direction indicated in degrees=D
For angles from 0 to 90 degrees $RO=5+(D/90)*95$ For angles from 90 to 180 degrees $RO=100$ For angles from 180 to 270 degrees $RO=5+((270-D)/90)*95$ For angles from 270 to 360 degrees $RO=5$     Equation Set 2

Thus, according to the above formulas, a direction to be indicated of 45 degrees will result in left tactile output device 301 having an output of 5% and the right tactile output device 302 having an output of 52.5%. Similarly, a direction to be indicated of 225 degrees will result in left tactile output device 301 having an output of 100% and the right tactile output device 302 having an output of 52.5%. These scenarios are illustrated in FIG. 5.

In a variation of the alternate embodiment illustrated in chart 500 of FIG. 5, the output values discussed may be triggered by a sound that exceeds a predetermined decibel level, and for sounds below the predetermined decibel level, all of the values illustrated in chart 500 may be reduced, such as for example, they may be halved. In this regard, a completely deaf person using the directional indication system 100 to alert them of sound events may also receive some level of information regarding the intensity of the signaled sound event. It is noted that in such a configuration it may be disadvantageous to have the values reduced too far since the user may lose the ability to distinguish loud events directly in front of them from quiet events directly behind them. In this regard, for example, if a low level sound directly behind the user were to trigger tactile outputs of 10% maximum set output, it may be hard for the user to distinguish such an output from a high level sound directly in front of the user that triggers tactile outputs of 5% of maximum set output.

Figure 6:
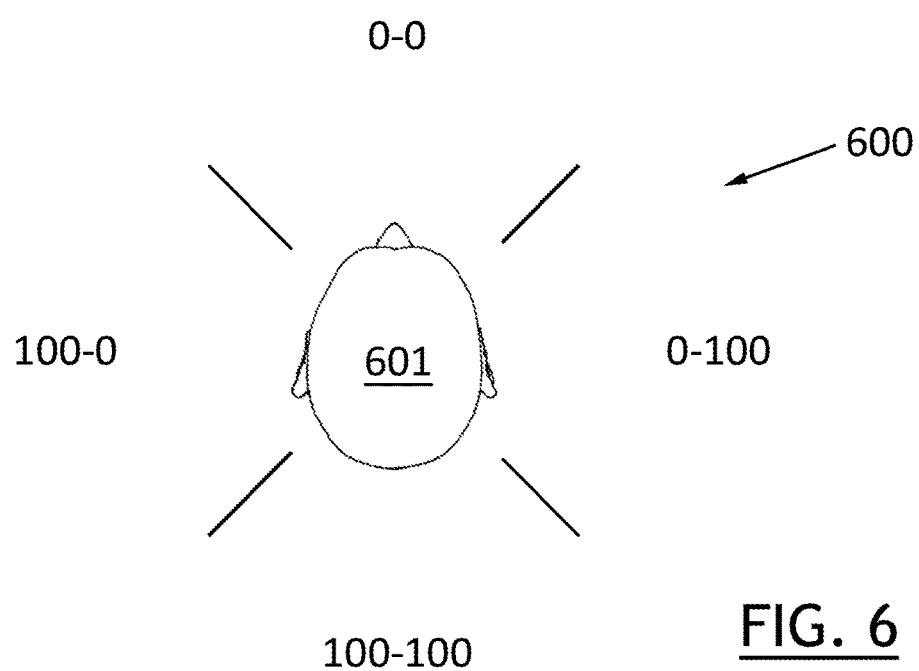
FIG. 6 is a chart indicating additional alternate output power levels of a directional indication system for various directions within a transverse plane of a user.

The configurations illustrated in FIGS. 4 and 5 show directional outputs that are continuously variable across the full 360 degrees. In an alternate embodiment, shown in chart 600 of FIG. 6, the directional indication from the directional indication system 100 may be a step function where the directional indication system 100 indicates a general direction. For example as shown in FIG. 6, to indicate a direction to the right of the head 601 of a user, the directional indication system 100 may produce a left tactile output of 0% and a right tactile output of 100%. Such outputs may indicate to the user a direction between 45 degrees and 135 degrees relative to the head 601 of the user. Similarly, to indicate a direction to the left of the head 601 of a user, the directional indication system 100 may produce a left tactile output of 100% and a right tactile output of 0%. Such outputs may indicate to the user a direction between 225 degrees and 315 degrees relative to the head 601 of the user. In the present configuration, the directional indication system 100 would produce no tactile outputs for directions between 315 degrees and 45 degrees relative to the head 601 of the user. To indicate a direction behind of the head 601 of a user, the directional indication system 100 may produce a left tactile output of 100% and a right tactile output of 100%. Such outputs may indicate to the user a direction between 135 degrees and 225 degrees relative to the head 601 of the user. These values are shown below:

TABLE 1

| Range | Left Output % | Right Output % |
| --- | --- | --- |
| 315-45 | 0 | 0 |
| 45-135 | 0 | 100 |
| 135-225 | 100 | 100 |
| 225-315 | 100 | 0 |

Figure 7:
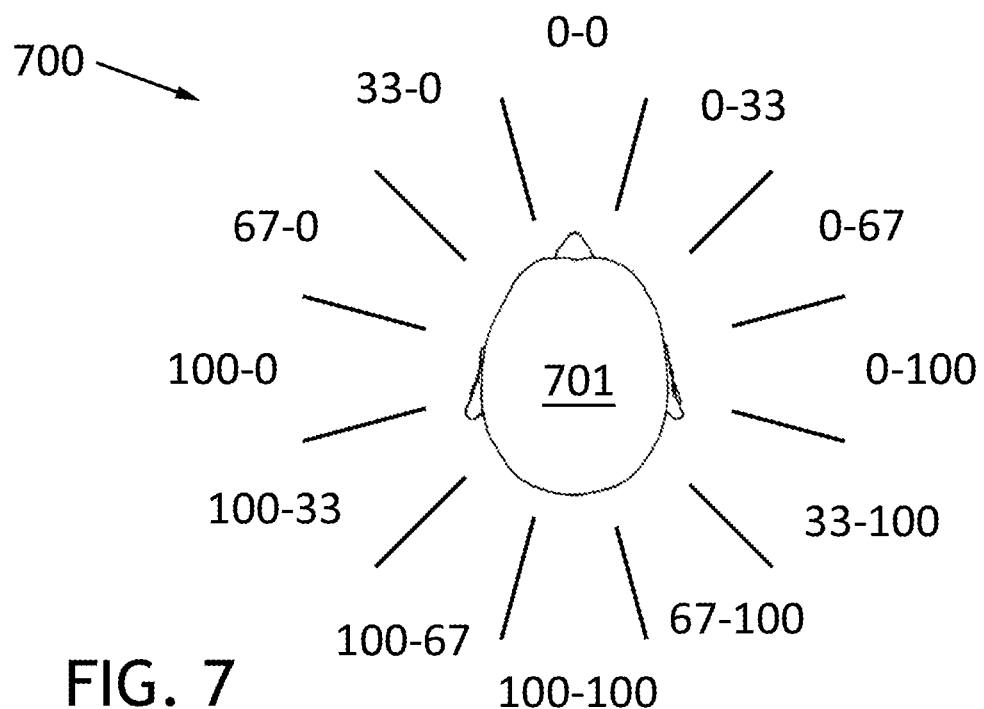
FIG. 7 is a chart indicating additional alternate output power levels of a directional indication system for various directions within a transverse plane of a user.

FIG. 7 is a chart 700 of a step function that is an alternate configuration of that shown in FIG. 6. In the configuration of FIG. 7, the 90 degree steps of the configuration of FIG. 6 are replaced with 30 degree steps. Thus, for example, a direction between 15 and 45 degrees relative to a head 701 of a user will be indicated by a left tactile output of 0% and a right tactile output of 33%, and a direction between 45 and 75 degrees relative to the head 701 of a user will be indicated by a left tactile output of 0% and a right tactile output of 67%. In this regard, the outputs may be as shown below:

TABLE 2

| Range | Left Output % | Right Output % |
| --- | --- | --- |
| 345-15 | 0 | 0 |
| 15-45 | 0 | 33 |
| 45-75 | 0 | 67 |
| 75-105 | 0 | 100 |
| 105-135 | 33 | 100 |
| 135-165 | 67 | 100 |
| 165-195 | 100 | 100 |
| 195-225 | 100 | 67 |
| 225-255 | 100 | 33 |
| 255-285 | 100 | 0 |
| 285-315 | 67 | 0 |
| 315-345 | 33 | 0 |

Figure 8:
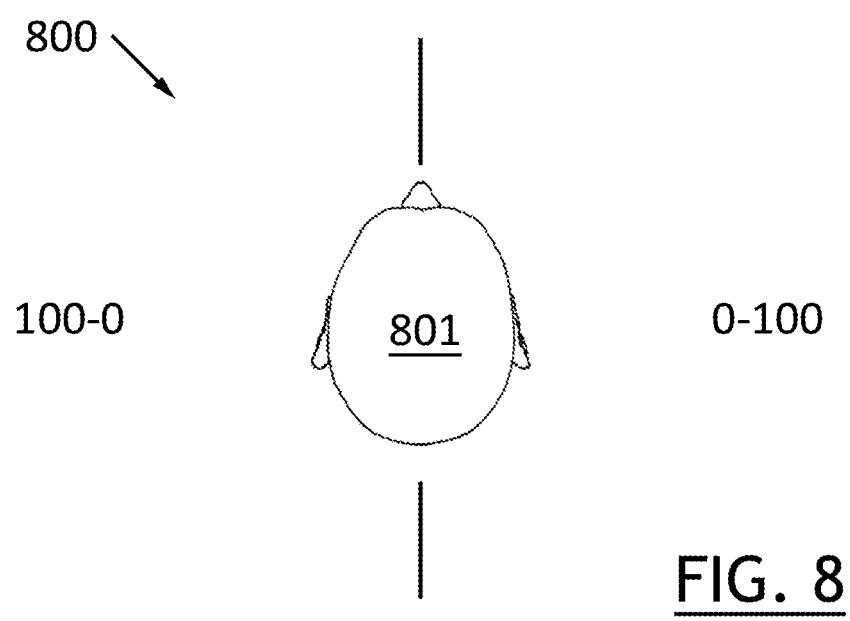
FIG. 8 is a chart indicating additional alternate output power levels of a directional indication system for various directions within a transverse plane of a user.

FIG. 8 is a chart 800 of a step function that is another alternate configuration. In the configuration of FIG. 8, the 90 degree steps of the configuration of FIG. 6 are replaced with 180 degree steps. Thus, for example, a direction between 0 and 180 degrees relative to a head 801 of a user will be indicated by a left tactile output of 0% and a right tactile output of 100%, and a direction between 180 and 360 degrees relative to a head 801 of the user will be indicated by a left tactile output of 100% and a right tactile output of 0%. In this regard, the outputs may be as shown below:

TABLE 3

| Range | Left Output % | Right Output % |
| --- | --- | --- |
| 0-180 | 0 | 100 |
| 180-360 | 100 | 0 |

The above described modes of directional indication are exemplary and additional modes, such as different formulas, different ranges, or combinations of ranges and formulas may be used to determine the outputs of the left tactile output device 301 and right tactile output device 302 for particular indicated directions.

The directional indication system 100 may be operable to switch between modes of operation. For example, a health care provider or the user may be able to switch between the various modes of directional indication described above or other available modes. A user may first use the mode of operation described with relation to FIG. 6 and then switch to the mode of operation of FIG. 7 as the user becomes acclimated to the directional indication system 100 and desires for more precise input as to an indicated direction.

As noted above, FIG. 5 represents a configuration of the directional indication system 100 where the directional indication system 100 produce an output to signal a direction directly ahead of the head 501 of the user. This is as a variation of the embodiment described in FIG. 4 where a low power value (5% in the configuration of FIG. 5) is used in place of 0% output values. Such an alteration may also be applied to the configurations of FIGS. 6 and 7 such that these systems may produce positive signals to indicate directions in front of the heads 601, 701 of users, respectively.

Hearing aids generally include openings for the input (through one or more microphones) and output (amplified to assist hearing) of sound. This typically results in most hearing aids being susceptible to damage from moisture. In contrast, the left and right units 101, 102 may be sealed such that they are dustproof and/or waterproof. As such, they may be worn in environments that are typically problematic for hearing aids such as while swimming or working in dusty environments.

As discussed earlier, the left and right units 101, 102 may be worn proximate to the left and right ears of a user. Such positioning has advantages. As noted above, the pinnae are particularly sensitive to tactile stimulation which may help users to quickly recognize the input and to better distinguish various levels of power output needed to discern the indicated direction as compared to stimulating other parts of the user. Additionally, positioning the left and right units 101, 102 proximate to the left and right ears, respectively, of a user is advantageous since the indicated direction will be relative to the head of the user in the same way that sound localization for a normal-hearing person is determined relative to the head. In this regard, the indicated directions being relative to the head of the user simulates the natural way that humans localize sound and therefore may make the directional indication system 100 easier to use and understand.

Returning to the block diagram of the directional indication system 100 in FIG. 3, the left unit 101 further includes a communication module 303 and a power source 305, and the right unit 102 further includes a communication module 304 and a power source 306. The communication modules 303, 304 may be capable of independently receiving communication regarding a direction to be indicated to the user by the directional indication system 100. The communication to the communication modules 303, 304 may be in any appropriate form.

Alternatively, one of the left unit 101 and the right unit 102 may be a master unit that it is capable of receiving communication regarding a direction to be indicated to the user by the directional indication system 100. In turn, the master unit may then communicate to the other unit the information necessary for the directional indication system 100 to indicate a direction to the user.

The communication to the directional indication system 100 may be in the form of a digital signal that includes data representative of the output to be generated by each of the tactile outputs 301, 302. In such a scenario, for example, a signal may be sent to the communication module 303 which causes the left tactile output device 301 to generate a tactile output at 100% of its maximum set output, while a signal may be sent to the communication module 304 which causes the right tactile output 302 to generate a tactile output at 50% of its maximum set output. Under the embodiment of FIG. 4, such a combination of outputs would signal to the user a direction of 225 degrees. Alternatively, the communication may be a digital signal that includes data representative of the direction to be indicated to the user and the left and right units 101, 102 may be operable to calculate the corresponding power outputs of the tactile output devices 301, 302 to indicate to the user the correct direction. In such a scenario, for example, and under the embodiment of FIG. 4, a signal may be sent to the communication modules 303, 304 that indicates a direction of 225 degrees, and in response the left tactile output device 301 generates a tactile output at 100% of its maximum set output, while the right tactile output device 302 generates a tactile output at 50% of its maximum set output. Accordingly, the left and right units 101, 102 may include processors 307, 308, respectively, to facilitate producing outputs at the tactile output devices 301, 302 based on signals received by the communication modules 303, 304. As used herein, the term processor designates a component or group of components capable of performing the described functions. In this regard, a processor may be a single electronic device, a group of devices, and/or portions of devices configured to perform a particular function. A processor may be any appropriate combination of software, firmware, and/or hardware capable of performing the described functions.

The left and right units 101, 102 may be capable of communicating with each other via the communication modules 303, 304. Such communication may be used to synchronize tactile output to better communicate an indicated direction to the user.

The power sources 305, 306 may be any appropriate source of power capable of powering the tactile outputs 301, 302, communication modules 303, 304, and processors 307, 308. The power sources 305, 306 may be replaceable batteries such as typically used in hearing aids. The power sources 305, 306 may be rechargeable batteries.

Figure 9:
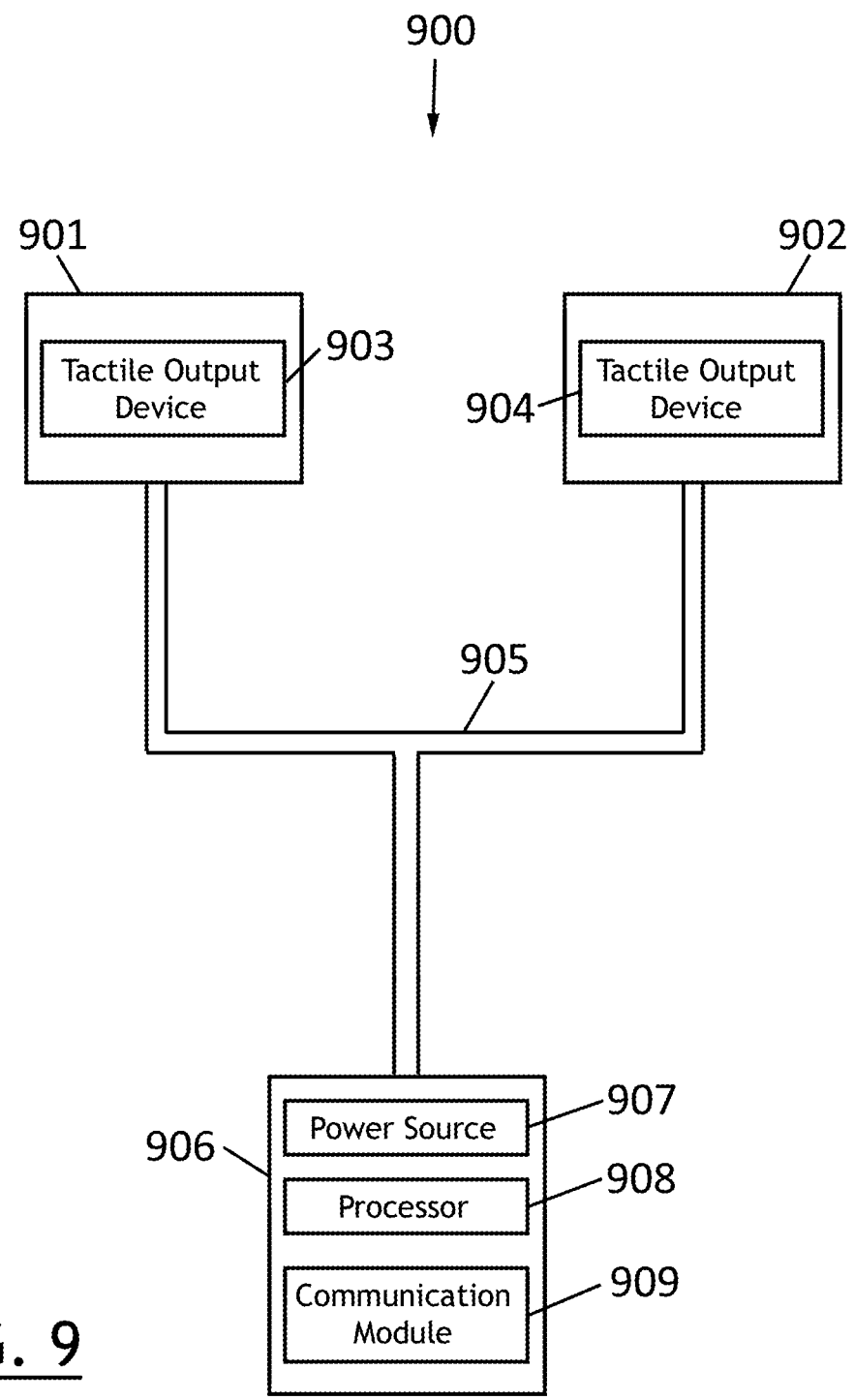
FIG. 9 is a functional block diagram of a directional indication system where components are interconnected by wiring.

FIG. 9 is an illustration of an alternate embodiment of a directional indication system 900. The directional indication system 900 is a wired version of the directional indication system 100 of FIG. 1. Indeed, all of the discussion above pertaining to how the directional indication system 100 may indicate to a user an indicated direction is also applicable to the directional indication system 900. In this regard, the directional indication system 900 has a left unit 901 and a right unit 902. These left and right units 901, 902 may be configured to be worn by a user in any appropriate fashion including similar to how the directional indication system 100 may be configured.

The directional indication system 900 may include wiring 905 that is connected to both the left unit 901 and the right unit 902. The wiring 905 may facilitate delivering power to, and/or controlling, a tactile output device 903 within the left unit 901 and a tactile output device 904 within the right unit 902. Accordingly, the communications modules 303, 304, power sources 305, 306, and processors 307, 308 of the directional indication system 100 may not be located within the left and right units 901, 902. The wiring 905 of the directional indication system 900 may be configured such that the tactile output devices 903, 904 may be remotely connected to a source of power and/or control.

For example, a remote control module 906 may be interconnected to the left and right units 901, 902 via the wiring 905. The remote control module 906 may include a power source 907 and processor 908 capable of controlling the tactile output devices 903, 904 similarly to how the tactile output devices 301, 302 are controlled in the directional indication system 100 previously described.

The remote control module 906 may be sized and configured to fit into a pocket or hang around the neck of a user. Any other appropriate way for a user to carry the remote control module 906 may be employed. The remote control module 906 may generate an indicated direction or it may receive an indicated direction from an external support. The remote control module 906 may include a communication module 909 through which it may receive indicated directions and/or other appropriate information.

In an exemplary configuration of the directional indication system 900, the directional indication system 900 may be configured similar to outside the ear headphones (which include two portions configured to fit over or against the outside of the ears of the user with an interconnecting portion that interconnects the two portions and enables the headphones to be secured to the user's head) with wiring 905 placed along the interconnecting portion of the. In such a configuration, the remote control module 906 may be positioned as previously described or it may be interconnected to any appropriate portion of the headphones which interconnects the ear pieces.

The directional indication systems 100, 900 may provide directional indications to users for any appropriate reason. For example, a completely deaf person may wear and use one of the directional indication systems 100, 900 to provide information regarding sounds in their environment. In such a scenario, the directional indication system 100, 900 may be coupled to a sound direction determination system. The directional indication systems 100, 900 may receive directional information regarding detected sounds and indicate to the deaf person a direction of a source of a sound in real-time or near real-time. Such information may be used to alert the deaf person as to the direction of a sound. In response the deaf person may turn toward the sound source and then may be able to determine the source of the sound and respond accordingly. For example, a person may call out to a completely deaf person and the directional indication system worn by the deaf person may indicate a direction to the deaf person, the deaf person may turn toward the sound and see the person who called out to them, and then engage in communication with the other person, such a through sign language. Other examples of sound sources a deaf person may wish to be aware of include alarm clocks, ringing phones, moving cars, car horns, falling objects, people or pets in distress, teachers, and teammates in sports. These examples represent a small fraction of the types of sounds that may be beneficial and/or desirable for a completely deaf person to be alerted to.

The directional indication systems 100, 900 may be interfaced with other systems to provide specific alerts. For example, directional indication systems 100, 900 may provide a unique tactile output as a notification that a doorbell has been activated or that an incoming communication on a telecommunications device for the deaf (TDD) has arrived. The unique tactile output may, for example, be a short vibration repeated three times in quick succession. This special signal may be used to alert the user of the specific event.

In another example of an application, the directional indication systems 100, 900 may be used by people who have some degree of hearing, but have reduced or no sound localization capabilities. For example, people who have SSD may also lack the ability to localize sound based solely on the sound they are hearing. That is, they cannot localize sounds in the same way that a normal hearing listener would localize sounds. When normal hearing listeners localize sound sources, they often rely on the interaural cues to determine the direction of the source of the sound. Since SSD individuals lack hearing in one ear, they also lack any interaural clues and thus lack normal localization abilities.

Accordingly, a SSD person may use the directional indication systems 100, 900, again interconnected to a sound direction determination system, to provide sound localization capabilities. In such an application, the SSD person may be capable of hearing sounds and may not use hearing aids, but may desire to have better localization capabilities. The directional indication systems 100, 900 may be used to provide real-time directional indications of environmental sounds. Alternately, the SSD person may were hearing aids, such as a crossover hearing aid system. A crossover hearing aid system is a hearing aid system that detects sounds at the deaf ear, transmits information regarding the detected sounds to a hearing aid at the functioning ear of the SSD person, and then plays sounds based on the detected sounds into the functioning ear of the SSD person. The sounds played may, for example, be filtered to make certain sounds such as speech more prominent and/or easier to understand. Thus for a person with SSD, their ability to hear sounds coming from their side corresponding to their deaf ear is enhanced with a crossover hearing aid system. The directional indication systems 100, 900 may be worn with a crossover hearing aid system or may be incorporated into a crossover hearing aid system to help provide sound localization.

People who have some degree of hearing loss in one or both ears and wear hearing aids may suffer from reduced sound localization capabilities depending on the individual and level of boosting needed. Hearing aids typically amplify sounds, however, oftentimes, hearing aid users perceive the amplified sounds as being produced in their ears as opposed to the 3 dimensional space surrounding them. This may result in diminished sound localization capabilities. The directional indication systems 100, 900 may be worn with a typical amplifying hearing aid system or may be incorporated into such a system to help provide and/or enhance sound localization.

The directional indication systems 100, 900 may be used in situations where the communication of directional information through audible or visual means may be undesirable. Furthermore, by using tactile output to indicate direction, a user's available visual and/or audible bandwidths (i.e., the total amount of information they are capable of receiving) may not be diminished.

The directional indication systems 100, 900 may be incorporated into virtual reality systems. The direction indicated may, for example, correspond to the direction of an element in a virtual reality simulation, such as the direction from which a gunshot originated in a video game. In this regard, instead of the typical left/right distinction of such systems use (due to their having speakers positioned at the user's ears similar to typical headphones), a virtual reality system with an incorporated directional indication system 100, 900 may be capable of indicating a more precise direction.

The direction indicated by directional indication systems 100, 900 may, in yet another example, correspond to the direction of a teammate, thus allowing team members to know each other's positions without audible communications. Such an embodiment may be useful in law enforcement and/or military scenarios where audible or visual communications may reveal a tactical position or where audible or visual communications may interfere with such a person's awareness of their environment.

In still other embodiments, the directional indication systems 100, 900 may indicate the direction of a target to be achieved or a hazard to be avoided. Such systems may help individuals navigate without taking up such an individual's available visual and/or audible bandwidths. For example, such systems may help blind people navigate while not taking up their audible bandwidth. Such navigation may be localized, such as within a building, or it may be larger, such as within a neighborhood or city. In such a system, the directional indication system 100, 900 may be interconnected to a navigation system, such as a GPS system or cell phone network.

Figure 10:
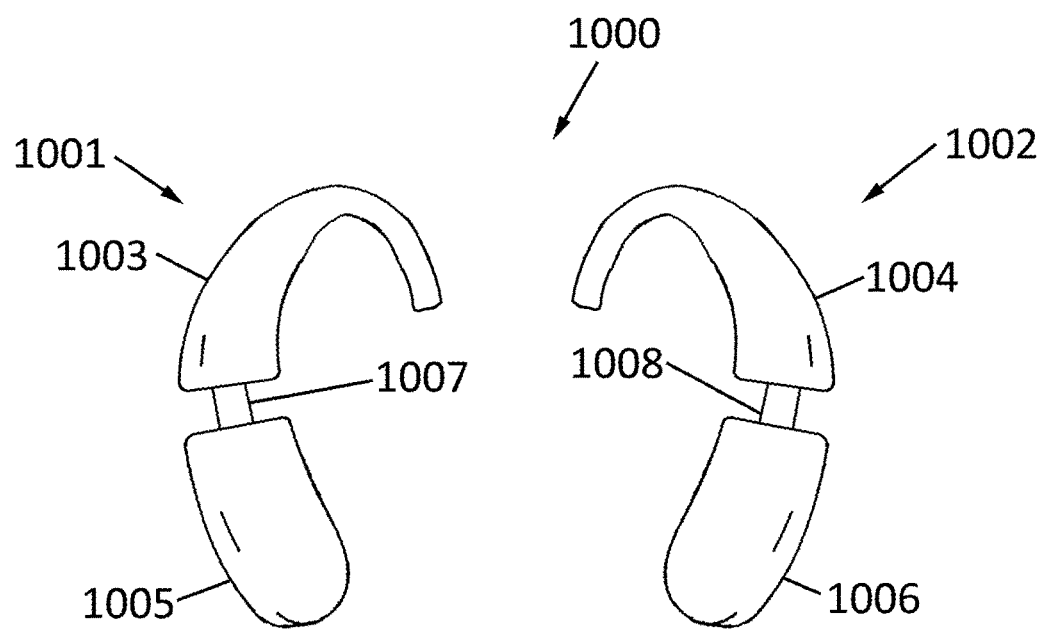
FIG. 10 is a perspective view of a directional indication system with vibration isolation that may be worn by a user.

FIG. 10 is an illustration of an embodiment of a three-dimensional directional indication system 1000. The three-dimensional directional indication system 1000 may operate similarly to the directional indication systems 100, 900 discussed above and may also be used in similar applications as described above. However, the three-dimensional directional indication system 1000 is operable to indicate a three-dimensional direction to a user, i.e., the three-dimensional directional indication system 1000 may be operable to indicate the directions within the transverse plane of the head of the user as described above with respect to the directional indication systems 100, 900, and also indicate inclination or declination relative to the transverse plane. Thus, the three-dimensional directional indication system 1000 may indicate any direction relative to the head of a user.

The direction indicated may, for example, correspond to the direction of a sound source relative to the three-dimensional directional indication system 1000. In such a scenario, the three-dimensional directional indication system 1000 may inform the user of the direction from which a sound is originating. Such an embodiment may be helpful to a user who does not have the ability to localize sound sources, such as an individual who has SSD, unilateral hearing loss, bilateral hearing loss or is completely deaf. The direction indicated may, similar to as discussed above, correspond to the direction of an element in a virtual reality simulation, the direction of a teammate, and/or the direction of a target to be achieved or a hazard to be avoided.

Figure 11:
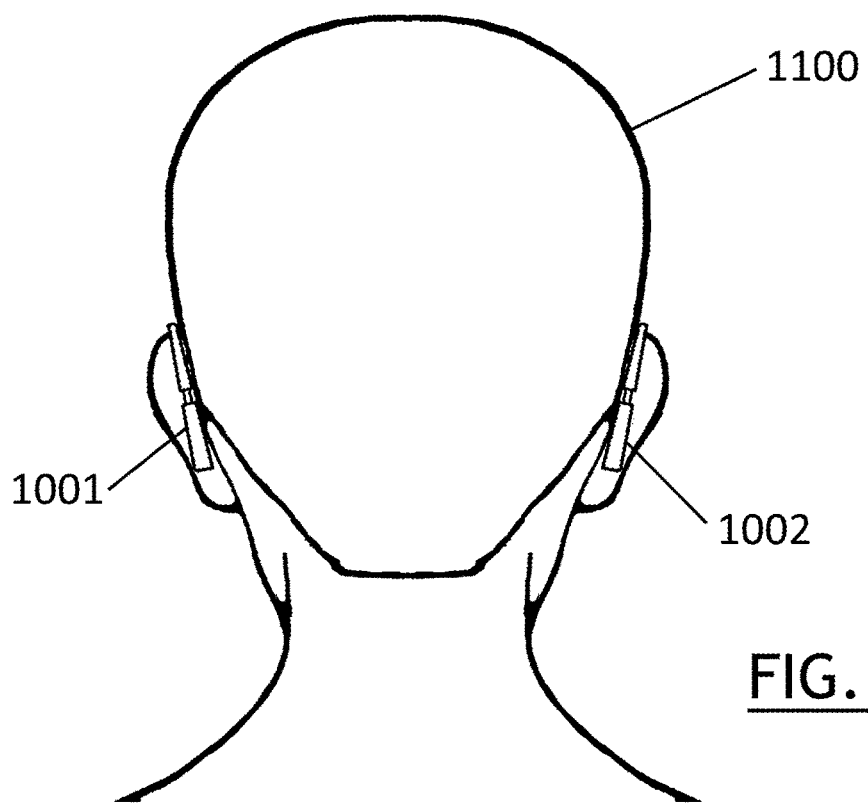
FIG. 11 is a rear view of a user wearing a directional indication system with vibration isolation.

The three-dimensional directional indication system 1000, shown in FIG. 10, comprises a left unit 1001 and a right unit 1002. The left and right units 1001, 1002 may be shaped and include features such that the left and right units 1001, 1002 may be worn behind the left and right ears, respectively, of a user. FIG. 11 illustrates a user 1100 wearing the left and right units 1001, 1002.

Returning to FIG. 10, the left and right units 1001, 1002 may be shaped such that they are capable of being worn behind the ears of a user similar to the left and right units 101, 102 of FIG. 1. The left unit 1001 includes an upper portion 1003 and a lower portion 1005. The upper portion 1003 and the lower portion 1005 are interconnected by an isolation link 1007. Similarly, the right unit 1002 includes an upper portion 1004 and a lower portion 1006. The upper portion 1004 and the lower portion 1006 are interconnected by an isolation link 1008. The left and right units 1001, 1002 may be shaped similarly to the left and right units 101, 102 of the directional indication system 100 discussed above (including the discussed configuration variations) such that the left and right units 1001, 1002 may be securely attached proximate to the ears of the user. The left and right units 1001, 1002 may be configured in any appropriate variation, similar to as discussed above with respect to the left and right units 101, 102. For example, the upper portion 1003 may be positioned behind the top of the ear and the lower portion 1005 may be configured as an earring.

Figure 12:
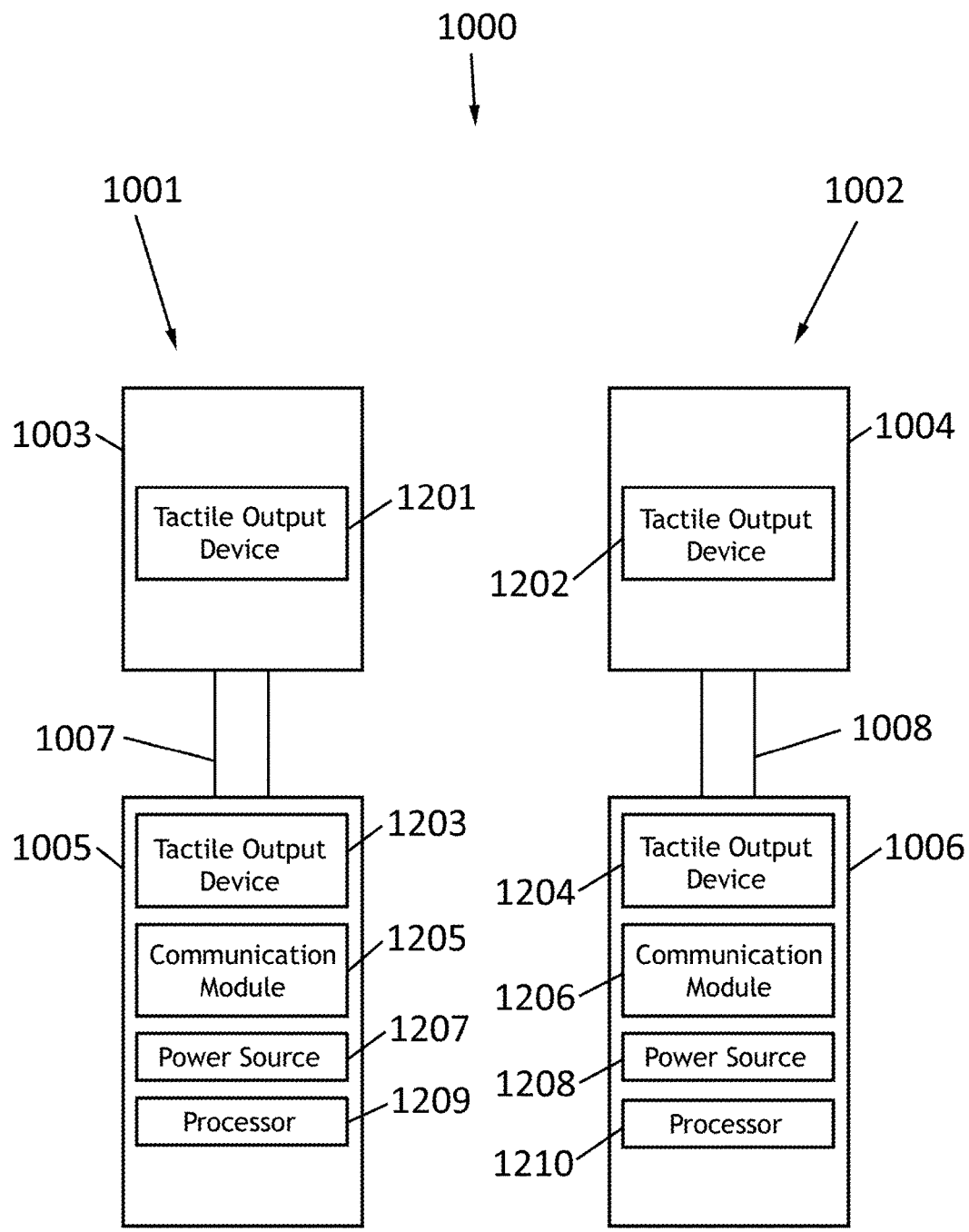
FIG. 12 is a functional block diagram of a directional indication system with vibration isolation.

FIG. 12 is a block diagram of the three-dimensional directional indication system 1000 depicting components of the left and right units 1001, 1002.

The left unit 1001 includes a tactile output device 1201 interconnected to the upper portion 1003 and a tactile output device 1203 interconnected to the lower portion 1005. The upper portion 1003 and the lower portion 1005 are interconnected to each other by the isolation link 1007. The right unit 1002 includes a tactile output device 1202 interconnected to the upper portion 1004 and a tactile output device 1204 interconnected to the lower portion 1006. The upper portion 1004 and the lower portion 1006 are interconnected to each other by the isolation link 1008. The tactile output devices 1201, 1202, 1203, 1204 are capable of independently producing a tactile output that a user wearing the left and right units 1001, 1002 can feel proximate to the user's left and right ears, respectively.

The isolation links 1007, 1008 are optional and when present function to vibrationally isolate the upper 1003, 1004 and lower 1005, 1006 portions from each other such that a user wearing the three-dimensional directional indication system 1000 may better discern between tactile outputs coming from the upper 1003, 1004 and lower 1005, 1006 portions. Thus, for example, if the tactile output device 1201 produces a tactile output while the tactile output 1205 does not produce a tactile output, the user will be able to determine that the tactile output is coming from the upper portion 1003. In this regard, the isolation links 1007, 1008 may not completely vibrationally isolate the upper 1003, 1004 and lower 1005, 1006 portions from each other, but they may do so to such a degree that the user may better discriminate between tactile outputs from the upper 1003, 1004 and lower 1005, 1006 portions.

The isolation links 1007, 1008 may be of any appropriate construction. For example, the isolation links 1007, 1008 may be made of a rubber material or polymer that may, to an appropriate degree, vibrationally isolate the upper 1003, 1004 and lower 1005, 1006 portions from each other. In another embodiment, the isolation links 1007, 1008 may be a set of insulated wiring that serves to vibrationally isolate the upper 1003, 1004 and lower 1005, 1006 portions and to provide electrical interconnection between elements in the upper portions 1003, 1004 and lower portions 1005, 1006.

The tactile output devices 1201, 1202, 1203, 1204 may be positioned such that the tactile outputs produced are felt on the pinnae of the user. For example, the tactile output devices 1201, 1202, 1203, 1204 may be positioned to stimulate the pinnae of the ears of the user, such as behind the ears and facing the pinnae of the user. The tactile output devices 1201, 1202, 1203, 1204 may be any appropriate device for producing a physical sensation felt by a user, similar to as described previously with respect to the tactile output devices 301, 302.

Figure 13:
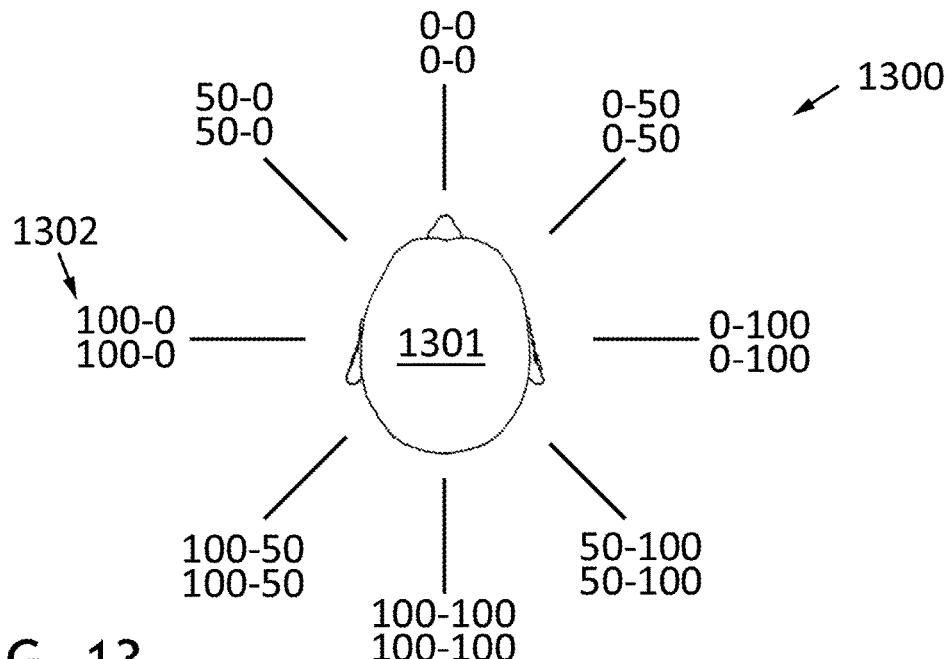
FIG. 13 is a chart indicating output power levels of a directional indication system with vibration isolation for various directions within a transverse plane of a user.
Figure 14:
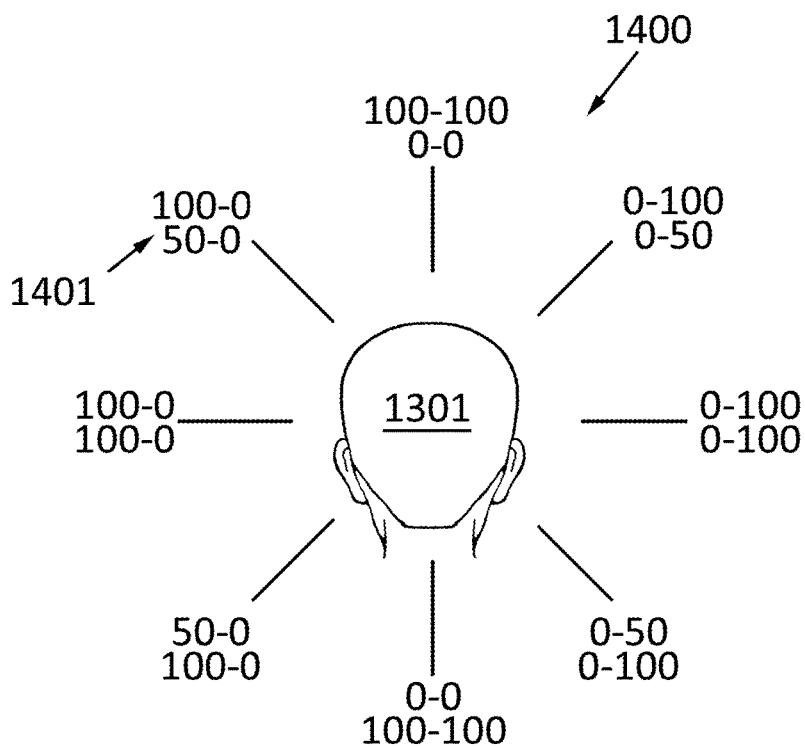
FIG. 14 is a chart indicating output power levels of a directional indication system with vibration isolation for various directions within a frontal plane of a user.
Figure 15:
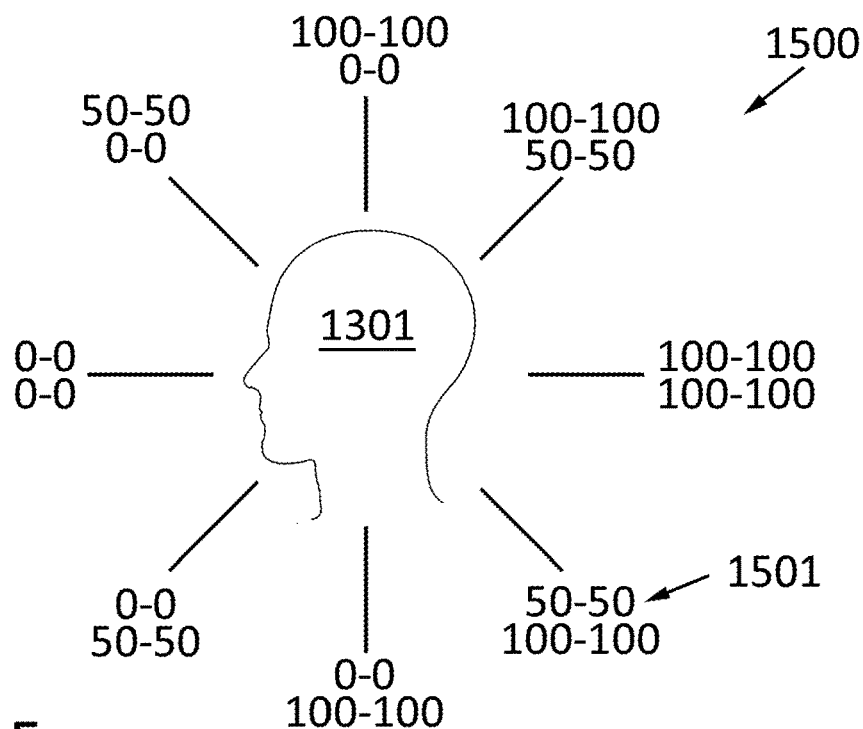
FIG. 15 is a chart indicating output power levels of a directional indication system with vibration isolation for various directions within a sagittal plane of a user.

The tactile sensations delivered to a user wearing the three-dimensional directional indication system 1000 by the tactile output devices 1201, 1202, 1203, 1204 may be used to communicate a direction to the user. The indicated direction is relative to the head of the user wearing the three-dimensional directional indication system 1000. FIGS. 13, 14 and 15 include charts 1300, 1400, and 1500 respectively that indicate power output, as a percentage of maximum set output, of the tactile output devices 1201, 1202, 1203, 1204 for various indicated directions. In FIGS. 13, 14 and 15, for each direction shown, the power outputs are shown as four numbers, two on an upper row and two on a lower row. The first number (on the left) of the two numbers on the upper row represents the power output of the tactile output device 1201 within the upper portion 1003 of the left unit 1001. The second number (on the right) of the two numbers on the upper row represents the power output of the tactile output device 1202 within the upper portion 1004 of the right unit 1002. The first number (on the left) of the two numbers on the lower row represents the power output of the tactile output device 1203 within the lower portion 1005 of the left unit 1001. The second number (on the right) of the two numbers on the lower row represents the power output of the tactile output device 1204 within the lower portion 1006 of the right unit 1002.

Chart 1300 of FIG. 13 is view of a transverse plane (viewed from above) of a head 1301 of a user with power outputs of the tactile output devices 1201, 1202, 1203, 1204 shown for various indicated directions. Chart 1400 of FIG. 14 is view of a coronal (or frontal) plane (viewed from behind) of the head 1301 with power outputs of the tactile output devices 1201, 1202, 1203, 1204 shown for various indicated directions. Chart 1500 of FIG. 15 is view of a sagittal plane (viewed from left) of the head 1301 with power outputs of the tactile output devices 1201, 1202, 1203, 1204 shown for various indicated directions.

For example, to indicate a direction to the left (with no inclination or declination) of the head 1301, the tactile output device 1201 of the upper portion 1003 of the left unit 1001 (also referred to herein as the upper left tactile output device 1201) and the tactile output device 1203 of the lower portion 1005 of the left unit 1001 (also referred to herein as the lower left tactile output device 1203) would each produce a tactile output of 100 percent of maximum set output, while the tactile output device 1202 of the upper portion 1004 of the right unit 1002 (also referred to herein as the upper right tactile output device 1202) and the tactile output device 1204 of the lower portion 1006 of the right unit 1002 (also referred to herein as the lower right tactile output device 1204) would each produce a tactile output of 0 percent of maximum set output. This is illustrated by the number group 1302 of Chart 1300.

In general, as in the immediately previous example, when the output of the upper left tactile output device 1201 is the same as the output of the lower left tactile output device 1203, and the output of the upper right tactile output device 1202 is the same as the output of the lower right tactile output device 1204, the three-dimensional directional indication system 1000 is indicating to the user a direction within the transverse plane of the head 1301 of the user.

In another example, to indicate a direction to the left and at an inclination of 45 degrees relative to the head 1301, the upper left tactile output device 1201 would produce a tactile output of 100 percent of maximum set output, the lower left tactile output device 1203 would produce a tactile output of 50 percent of maximum set output, and the upper right tactile output device 1202 and the lower right tactile output device 1204 would each produce a tactile output of 0 percent of maximum set output. This is illustrated by the number group 1401 of Chart 1400.

In general, as in the immediately previous example, when the output of one of the tactile output devices is at 100 percent of maximum set output while another of the tactile output devices is at 0 percent of maximum set output, the three-dimensional directional indication system 1000 is indicating to the user a direction within the coronal plane of the head 1301 of the user.

In another example, to indicate a direction directly behind and at a declination of 45 degrees relative to the head 1301, the upper left tactile output device 1201 and the upper right tactile output device 1202 would each produce a tactile output of 50 percent of maximum set output, and the lower left tactile output device 1203 and the lower right tactile output device 1204 would each produce a tactile output of 100 percent of maximum set. This is illustrated by the number group 1501 of Chart 1500.

In general, as in the immediately previous example, when the output of the upper left tactile output device 1201 is the same as the output of the upper right tactile output device 1202, and the output of the lower left tactile output device 1203 is the same as the output of the lower right tactile output device 1204, the three-dimensional directional indication system 1000 is indicating to the user a direction within the sagittal plane of the head 1301 of the user.

For directions not directly in front of, behind, to the left of, to the right of, above and below the user, the three-dimensional directional indication system 1000 may indicate direction to the user by producing vibration output according to the following formulas, where D is the direction (expressed in degrees) within the transverse plane to be indicated to the user with 0 degrees directly in front of the head 1301, 90 degrees to the right, 180 degrees behind, and 270 degrees to the left and I is the direction (expressed in degrees) of inclination (positive) or declination (negative) relative to the transverse plane. In Equation Set 3 below: $v=(I*D/90)$; $w=(100/90)$; $x=(270-D)$; $y=(360-D)$; and $z=(2*I)$.

In this regard, the above formulas for the three-dimensional directional indication system 1000 result in unique combination of outputs from the tactile output devices 1201, 1202, 1203, 1204 for each unique direction to be indicated. Thus it may be possible for a user of the three-dimensional directional indication system 1000 to interpret direction communicated by the three-dimensional directional indication system 1000 to a similar degree of accuracy that a normal hearing person is able to locate some sound sources. The process of learning to interpret the output of the three-dimensional directional indication system 1000 may take time and assistive devices and/or practices may be used to aid in learning to interpret the three-dimensional directional indication system 1000.

In general, the above formulas mathematically describe a system where: as sounds move to the front of the head of the user the outputs of the tactile output devices 1201, 1202, 1203, 1204 generally tend toward 0% of maximum output; as sounds move to the back of the head of the user the outputs of the tactile output devices 1201, 1202, 1203, 1204 generally tend toward 100% of maximum output; as sounds move to below the head of the user the outputs of the upper tactile output devices 1201, 1202, generally tend toward 0% of maximum output and the outputs of the lower tactile output devices 1203, 1204, generally tend toward 100% of maximum output; and as sounds move to above the head of the user the outputs of the upper tactile output devices 1201, 1202, generally tend toward 100% of maximum output and the outputs of the lower tactile output devices 1203, 1204, generally tend toward 0% of maximum output.

It is noted that the formulas described with relation to the three-dimensional directional indication system 1000 and shown in FIGS. 13-15 are exemplary and may be modified as appropriate. It is further noted that the vibration power is discussed in terms of percentage of maximum set output value, similar to as discussed above with relation to the tactile output devices 301, 302. It is also noted that, similar to as discussed above, the maximum set output value may be adjustable.

| Angle within transverse plane | Angle relative to transverse plane | Upper left tactile output 1101 | Lower left tactile output 1103 | Upper right tactile output 1102 | Lower right tactile output 1104 |
|---|---|---|---|---|---|
| 0 to 90 | 0 to 90 | $I * w$ | 0 | $(I + D - v) * w$ | $(D - v)*w$ |
| 0 to 90 | 0 to -90 | 0 | $-I * w$ | $(D + v) * w$ | $(D - I + v) * w$ |
| 90 to 180 | 0 to 90 | $(D + z - 90 - v) * w$ | $(D + I - 90 - v) * w$ | 100 | $(90 - I) * w$ |
| 90 to 180 | 0 to -90 | $(D - I - 90 + v) * w$ | $(D - z - 90 + v) * w$ | $(90 + I) * w$ | 100 |
| 180 to 270 | 0 to 90 | 100 | $(90 - I) * w$ | $(x - z + v) * w$ | $(x - 3 * I + v) * w$ |
| 180 to 270 | 0 to -90 | $(90 + I) * w$ | 100 | $(x + 3 * I + v) * w$ | $(x + z - v) * w$ |
| 270 to 360 | 0 to 90 | $(y - 3 * I + Z) * w$ | $(y - 4 * I + v) * w$ | $I * w$ | 0 |
| 270 to 360 | 0 to -90 | $(y + 4 * I - v) * w$ | $(y + 3 * I - v) * w$ | 0 | $-I * w$ |

Thus for example, according to the above formulas, a direction to be indicated of 45 degrees within the transverse plane and at an inclination of 45 degrees will result in the upper left tactile output device 1201 having an output of 45%, the lower left tactile output device 1203 having an output of 0%, the upper right tactile output device 1202 having an output of 75%, and the lower right tactile output device 1204 having an output of 25%. In another example, a direction to be indicated of 260 degrees within the transverse plane and at an declination of 60 degrees will result in the upper left tactile output device 1201 having an output of 33%, the lower left tactile output device 1203 having an output of 100%, the upper right tactile output device 1202 having an output of 4%, and the lower right tactile output device 1204 having an output of 70%.

In an alternate embodiment similar to the alternate embodiment discussed previously and illustrated in a chart 500 of FIG. 5, the three-dimensional directional indication system 1000 may be configured such that it produces a signal to the user to indicate a direction directly in front of the head 1301 of the user. In this regard, the above formulas would be modified to have an output range of, for example, 5% to 100% of the maximum set output of the tactile output devices 1201, 1202, 1203, 1204.

The formulas described with relation to the three-dimensional directional indication system 1000 and shown in FIGS. 13-15 show directional outputs that are continuously variable in three dimensions surrounding the head 1301 of the user.

In an alternate embodiment, shown in Table 4 below, the directional indication from the three-dimensional directional indication system 1000 may be a step function where the three-dimensional directional indication system 1000 indicates a general direction. In such an embodiment, the three-dimensional directional indication system 1000 may be configured to indicate a direction by selecting from a discrete number of directions.

In Table 4, the columns represent inclination or declination relative to the transverse plane of the head 1301 of the user in 45 degree increments. The rows represent the direction in the transverse plane with 0 degrees being in front of the head 1301 of the user and proceeding at 45 degree increments clockwise (as viewed from the top). The numbers in each cell of the Table 4, represent the output of the tactile output devices 1201, 1202, 1203, 1204, with the upper left number representing the output of the upper left tactile output device 1201, the lower left number representing the output of the lower left tactile output device 1203, the upper right number representing the output of the upper right tactile output device 1202, and the lower right number representing the output of the lower right tactile output device 1204.

TABLE 4

| Angle (degrees) within transverse plane | Inclination (degrees) relative to transverse plane | | | | | | | | | |
|---|---|---|---|---|---|---|---|---|---|---|
|  | -90 | | -45 | | 0 | | 45 | | 90 | |
| 0 | 0 | 0 | 0 | 0 | 0 | 0 | 44 | 44 | 100 | 100 |
|  | 100 | 100 | 56 | 56 | 0 | 0 | 0 | 0 | 0 | 0 |
| 45 |  |  | 0 | 25 | 0 | 56 | 45 | 75 |  |  |
|  |  |  | 45 | 75 | 0 | 56 | 0 | 25 |  |  |
| 90 |  |  | 0 | 44 | 0 | 100 | 44 | 100 |  |  |
|  |  |  | 56 | 100 | 0 | 100 | 0 | 56 |  |  |
| 135 |  |  | 25 | 50 | 44 | 100 | 75 | 100 |  |  |
|  |  |  | 75 | 100 | 44 | 100 | 25 | 50 |  |  |
| 180 |  |  | 44 | 44 | 100 | 100 | 100 | 100 |  |  |
|  |  |  | 100 | 100 | 100 | 100 | 56 | 56 |  |  |
| 225 |  |  | 50 | 25 | 100 | 56 | 100 | 75 |  |  |
|  |  |  | 100 | 75 | 100 | 56 | 50 | 25 |  |  |
| 270 |  |  | 44 | 0 | 100 | 0 | 100 | 44 |  |  |
|  |  |  | 100 | 56 | 100 | 0 | 56 | 0 |  |  |
| 315 |  |  | 25 | 0 | 56 | 0 | 75 | 45 |  |  |
|  |  |  | 75 | 45 | 56 | 0 | 25 | 0 |  |  |

Thus in such a scenario, the direction indicated may be one of the 26 discrete inclination/transverse plane angle combinations listed above. The three-dimensional directional indication system 1000 may receive a direction and then calculate which of the 26 discrete inclination/transverse plane angle combinations listed above best represents the direction of the received direction and then cause the three-dimensional directional indication system 1000 to output that direction.

In an another alternate embodiment, shown in Table 5 below, the directional indication from the three-dimensional directional indication system 1000 may be a step function where the three-dimensional directional indication system 1000 indicates a general direction selecting from a discrete number of directions, where the available directions are limited to cardinal directions (i.e., 0, 90, 180, and 270 degrees within the transverse plane and straight up and straight down).

TABLE 5

| Angle (degrees) within transverse plane | Inclination (degrees) relative to transverse plane | | | | | |
|---|---|---|---|---|---|---|
|  | -90 | | 0 | | 90 | |
| 0 | 0 | 0 | 0 | 0 | 100 | 100 |
|  | 100 | 100 | 0 | 0 | 0 | 0 |
| 90 |  |  | 0 | 100 |  |  |
|  |  |  | 0 | 100 |  |  |
| 180 |  |  | 100 | 100 |  |  |
|  |  |  | 100 | 100 |  |  |
| 270 |  |  | 100 | 0 |  |  |
|  |  |  | 100 | 0 |  |  |

Thus in such a scenario, the direction indicated may be one of the 6 discrete directions listed above. The three-dimensional directional indication system 1000 may receive a direction and then calculate which of the 6 discrete directions listed above best represents the direction of the received direction and then cause the three-dimensional directional indication system 1000 to output that direction.

The three-dimensional directional indication system 1000 may be operable to switch between modes of operation. For example, a health care provider or the user may be able to switch between the various modes of directional indication described above or other available modes.

Returning to the block diagram of the three-dimensional directional indication system 1000 in FIG. 12, the left unit 1001 further includes a communication module 1205 and a power source 1207, and the right unit 1002 further includes a communication module 1206 and a power source 1208. The communication modules 1205, 1206 may function similarly as described with reference to the communication modules 303, 304 of FIG. 3. Along the same lines, the left and right units 1001, 1002 may include processors 1209, 1210, respectively, to facilitate producing outputs at the tactile output devices 1201, 1202, 1203, 1204 based on signals received by one or both of the communication modules 1205, 1206. The left and right units 1001, 1002 may be capable of communicating with each other via the communication modules 1205, 1206. Such communication may be used to synchronize tactile output to better communicate an indicated direction to the user.

The power sources 1207, 1208 may be any appropriate source of power capable of powering the tactile output devices 1201, 1202, 1203, 1204, communication modules 1205, 1206, and processors 1209, 1210. The power sources 307, 308 may be replaceable batteries such as typically used in hearing aids. The power sources 307, 308 may be rechargeable batteries.

FIG. 12 depicts the left and right units 1001, 1002 with the communication modules 1205, 1206, power sources 1207, 1208, and processors 1209, 1210 located within the lower portions 1005, 1006. However, in alternate embodiments, one or more of these components may be located in the upper portions 1003, 1004. The communication modules 1205, 1206, power sources 1207, 1208, and processors 1209, 1210 may be located in whichever portions (upper or lower) that is most advantageous to ease of use, overall portion size, system performance, and/or any other appropriate reason. Moreover, the communication modules 1205, 1206 and processors 1209, 1210 may not be physically discrete items and may be incorporated into a single set of electronics or portions of the electronics used for communications or processing may be distributed between the upper portions 1003, 1004 and lower portions 1005, 1006. In this regard, there may be wiring between the upper portions 1003, 1004 and lower portions 1005, 1006 to facilitate interconnectivity between components located within the upper portions 1003, 1004 and lower portions 1005, 1006. Such wiring may be incorporated within the isolation links 1007, 1008 or they may be mechanically separate from the isolation links 1007, 1008.

In an alternate embodiment of the three-dimensional directional indication system 1000, the left and right units 1001, 1002 may be interconnected to each other by wiring. Such an embodiment may have the features and aspects relative to the three-dimensional directional indication system 1000 in a manner similar to the directional indication system 900 relative to the directional indication system 100. As such, the features discussed with respect to the directional indication system 900 may be incorporated into the present wired alternative embodiment of the three-dimensional directional indication system 1000.

The three-dimensional directional indication system 1000 may provide directional indications to users for any appropriate reason, similar to as discussed above with respect to the directional indication systems 100, 900.

Figure 16:
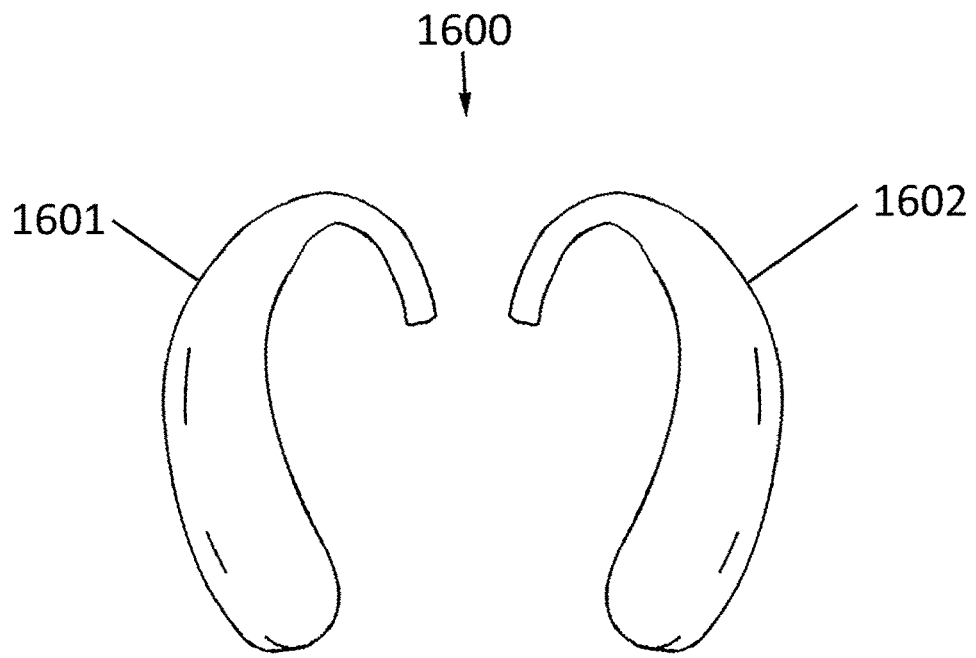
FIG. 16 is a perspective view of a three-dimensional directional indication system that may be worn by a user.
Figure 17:
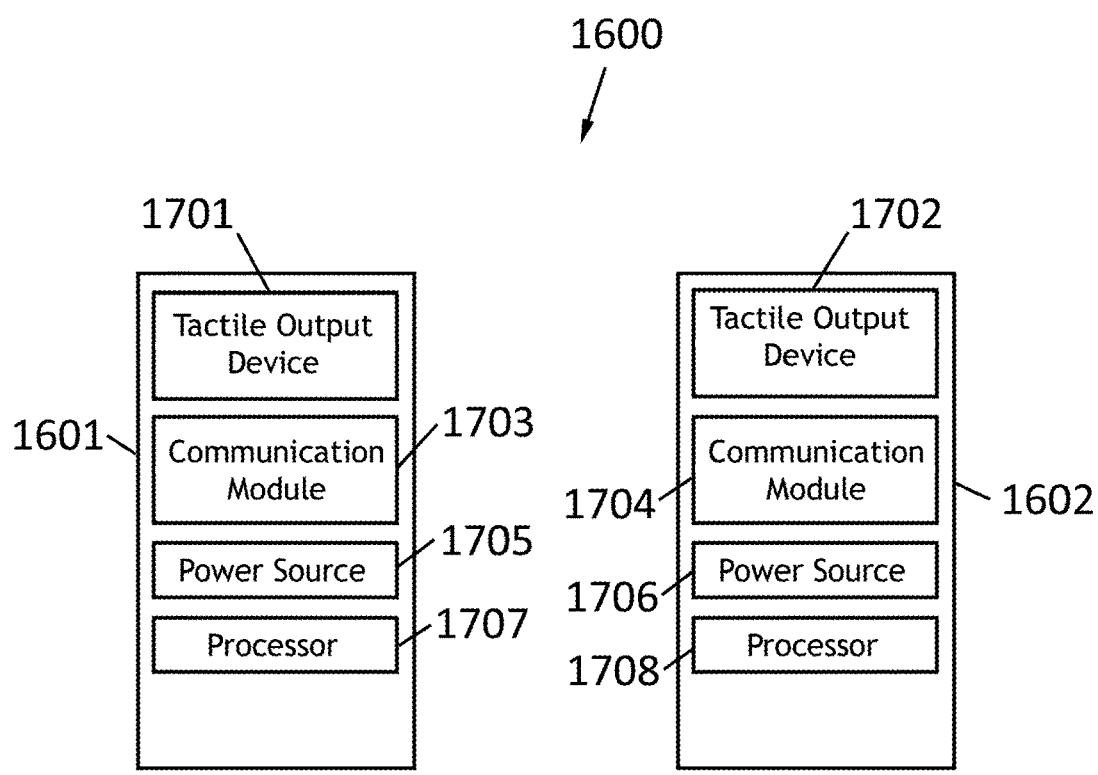
FIG. 17 is a functional block diagram of a three-dimensional directional indication system.

In another embodiment, a three-dimensional directional indication system 1600 is shown in FIGS. 16 and 17. The three-dimensional directional indication system 1600 includes a left unit 1601 and a right unit 1602. The left unit 1601 includes a tactile output device 1701, communication module 1703, power source 1705, and processor 1707. The right unit 1602 includes a tactile output device 1702, communication module 1704, power source 1706, and processor 1708.

The three-dimensional directional indication system 1600 uses two tactile output devices, tactile output device 1701 and tactile output device 1702, to indicate a direction in three dimensions. This is accomplished by varying the frequency of the output of the tactile output devices 1701, 1702 to communicate the inclination or declination of the direction to be indicated while communicating the angle of direction within the transverse plane of the head of the user in a manner similar to as discussed with respect to directional indication systems 100, 900.

For example, the frequency F (Hz) of the output of the tactile output devices 1701, 1702 may be governed by the following equation where I is the direction (expressed in degrees) of inclination (positive) or declination (negative) relative to the transverse plane:

$$F=(I+90)*(200/180)+100 \qquad \text{Equation Set 4}$$

Thus for example, when the direction to be indicated is directly above the user (+90 degrees), the output frequency of the tactile output devices 1701, 1702 is 300 Hz, when the direction to be indicated is within the transverse plane of the user (0 degrees), the output frequency of the tactile output devices 1701, 1702 is 200 Hz, and when the direction to be indicated is directly below the user (−90 degrees), the output frequency of the tactile output devices 1701, 1702 is 100 Hz.

In another example, the frequency F (Hz) of the output of the tactile output devices 1701, 1702 may be a step function where: if the indicated direction is above 30 degrees of inclination, the frequency of the output of the tactile output devices 1701, 1702 is 300 Hz; if the indicated direction is between 30 degrees of inclination and 30 degrees of declination, the frequency of the output of the tactile output devices 1701, 1702 is 200 Hz; and if the indicated direction is below 30 degrees of declination, the frequency of the output of the tactile output devices 1701, 1702 is 100 Hz.

The above examples of variable frequency to indicate elevation of a direction to be indicated are exemplary and the transition points, frequency levels, and whether a step function is used or the frequency is continuously variable, may be varied. Such varying may be performed by a technician, an audiologist, a physician and/or a user.

Accordingly, for example, in an embodiment where the indication of elevation is governed by Equation Set 4 and the indication is of angle within the transverse plane is governed by Equation Set 1, a direction to be indicated of 315 degrees within the transverse plane of the head of the user at an elevation of 45 degrees would be indicated by a left tactile output of 50 percent of maximum set power and a right tactile output of 0 percent of maximum set power with both tactile output devices 1701, 1702 operating at 250 Hz. In another example, where the indication of elevation is governed by Equation Set 4 and the indication of angle within the transverse plane is governed by Equation Set 1, a direction to be indicated of 100 degrees within the transverse plane of the head of the user at an elevation of −20 degrees (i.e., 20 degree declination) would be indicated by a left tactile output of 11 percent of maximum set power and a right tactile output of 100 percent of maximum set power with both tactile output devices 1701, 1702 operating at 178 Hz.

Figure 18:
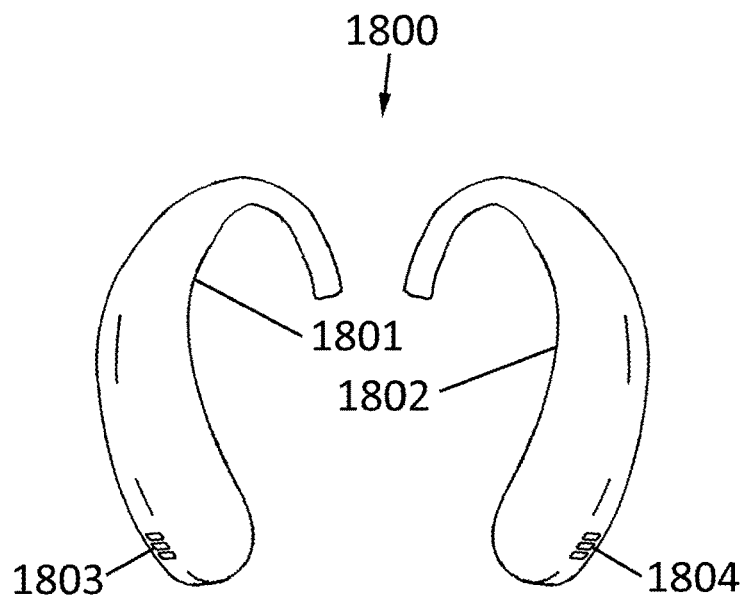
FIG. 18 is a perspective view of an audio source localization and indication system that may be worn by a user.

FIG. 18 is an illustration of an audio source localization and indication system 1800. The audio source localization and indication system 1800 is operable to determine a direction of an audio source and indicate that direction to a user. In this regard, the audio source localization and indication system 1800 may inform the user of the direction from which a sound is originating. Such an embodiment may be helpful to a user who does not have the ability to localize sound sources, such as an individual who has SSD, unilateral hearing loss, bilateral hearing loss or is completely deaf.

Any embodiments of the directional indication systems 100, 900 and three-dimensional directional indication systems 1000 discussed above may be incorporated in the audio source localization and indication system 1800 to provide directional indication to the user.

The audio source localization and indication system 1800, shown in FIG. 18, comprises a left unit 1801 and a right unit 1802. Similar to the left 101, 901, 1001 and right 102, 902, 1002 units discussed above, the left and right units 1801, 1802 may be shaped and include features such that the left and right units 1801, 1802 may be worn proximate to the left and right ears, respectively, of a user. Other configurations and related methods of attaching devices to the ear of a user known to those skilled in the art may be incorporated in the audio source localization and indication system 1800.

Figure 19:
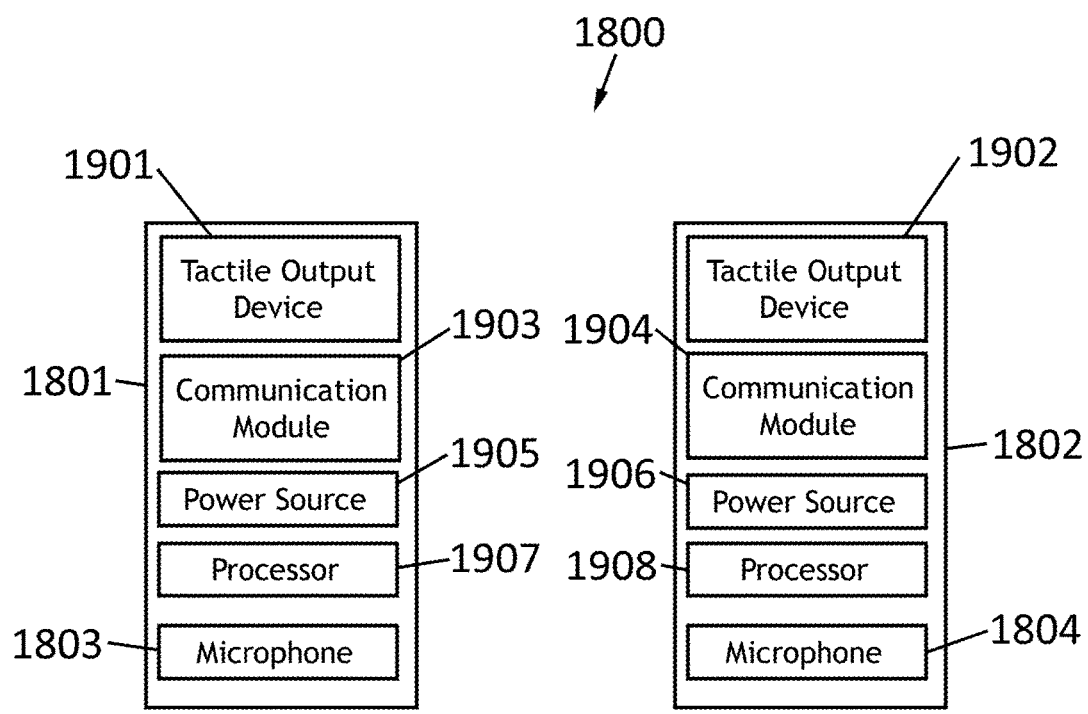
FIG. 19 is a functional block diagram of an audio source localization and indication system.

FIG. 19 is a block diagram of the audio source localization and indication system 1800 depicting internal components of the left and right units 1801, 1802. The left and right units 1801, 1802 include a tactile output device 1901 and a tactile output device 1902, respectively, that may be similar to the tactile output devices 301, 302 previously described. The left and right units 1801, 1802 further include communication module 1903 and communication module 1904, respectively, that may be similar to the communication modules 303, 304 previously described. The left and right units 1801, 1802 further include power source 1905 and power source 1906, respectively, that may be similar to the power sources 305, 306 previously described.

The left and right units 1801, 1802 further include processor 1907 and processor 1908, respectively, that perform a function similar to as previously described with respect to the processors 307, 308 along with additional audio source localization functions described below.

Returning to FIG. 18, the left unit 1801 further includes a microphone 1803 and the right unit 1802 further includes a microphone 1804. Microphones 1803, 1804 are also illustrated in FIG. 19. The microphones 1803, 1804 along with the processors 1907, 1908 may be used to determine a direction from which a sound is originating.

In general, the audio source localization and indication system 1800 will monitor sound being received by the microphones 1803, 1804 and, when a triggering event occurs, the audio source localization and indication system 1800 will output tactile sensations to the user via the tactile output devices 1901, 1902 to indicate the direction from which the triggering event occurred.

A triggering event, as defined herein, is an acoustical event that has been predetermined to be of adequate significance such that the audio source localization and indication system 1800 will produce a tactile output to provide the user with directional information related to the acoustical event. What constitutes a triggering event may be pre-programmed into the audio source localization and indication system 1800 and/or may be definable by, for example, an audio technician, audiologist and/or a user. The audio source localization and indication system 1800 may detect and respond to several different types of triggering events, including simultaneous triggering events.

In a first example of a triggering event, a triggering event may be any sound detected by the audio source localization and indication system 1800 where the audio source localization and indication system 1800 is able to determine a direction of (i.e., localize) the source of the sound. Such a determination may, for example, be whether the sound source is to the left or to the right of a user, or the determination may be more precise, such as a vector along which the sound source is located. The detected and localized sound may be the only sound detected and localized by the audio source localization and indication system 1800, or it may be one of two or more sounds simultaneously detected and localized by the audio source localization and indication system 1800. Where two or more sounds are simultaneously detected and localized, the audio source localization and indication system 1800 may select one of the detected and localized sounds and produce a tactile output to indicate the direction of the source of the selected sound to the user. Such a selection may, for example, be based on the volume of the simultaneously detected and localized sound. In another example, the selection may be based on the type of sound: for example, if only one of the simultaneously detected and localized sounds is speech, the speech may be the sound selected by the audio source localization and indication system 1800.

Alternatively, the audio source localization and indication system 1800 may select all of the simultaneously detected and localized sounds or any subset thereof and alternately produce tactile outputs for each of the selected sounds. For example, if first and second sounds are simultaneously detected and localized by the audio source localization and indication system 1800, the audio source localization and indication system 1800 may alternate between producing tactile output indicating the direction of the source of the first sound and producing a tactile output indicating the direction of the source of the second sound. The duration of time that each sound is indicated may be selected such that the user is able to comprehend each direction being indicated. The duration may be adjustable by, for example, the user or an audiologist.

In a second example of a triggering event, a triggering event may be any sound detected that is over a predetermined decibel level. That is, whenever the audio source localization and indication system 1800 detects a sound that is over the predetermined decibel level, the audio source localization and indication system 1800 reacts by outputting tactile sensations to indicate to the user the direction from which the sound originated. The audio source localization and indication system 1800 may continue to output tactile sensations indicating source direction as long as the audio source localization and indication system 1800 detects the sound over the predetermined decibel level. Therefore, for example, if a siren were to emit a high decibel sound, the audio source localization and indication system 1800 may output tactile sensations for as long as the decibel level of the siren remains above the predetermined level sensed at the audio source localization and indication system 1800.

Alternatively, the audio source localization and indication system 1800 may only output tactile sensations for a predetermined amount of time after the initial sensing of the sound that is over the predetermined decibel level. Therefore, for example, if a siren were to emit a high decibel sound, the audio source localization and indication system 1800 may output tactile sensations indicating source direction for a predetermined amount of time (for example, 1 second) and then stop outputting the tactile sensations after the predetermined amount of time has passed. Such an alert scheme may be beneficial in that once the user has been alerted to the direction of the sound, the user may no longer need the tactile outputs and stopping the tactile outputs has the benefits of freeing up the tactile output devices 1901, 1903 for delivery of additional localization information (e.g., such as a second siren) and/or saving battery life by limiting the duration of the tactile outputs.

In general, if the position of the sound source moves relative to the head of the user (due to the user moving his head and/or due to the sound source moving), the audio source localization and indication system 1800 may change or resume the tactile outputs to indicate the new direction of the source of the sound relative to the user's head.

In a third example of a triggering event, a triggering event may be any sound detected that is over a predetermined decibel level above the ambient or background level of sound at a particular time. That is, whenever the audio source localization and indication system 1800 detects a sound that is over the predetermined decibel level above the ambient level of sound at a particular time, the audio source localization and indication system 1800 reacts by outputting tactile sensations to indicate to the user the direction from which the sound that is over the predetermined decibel level above the ambient level originated.

The audio source localization and indication system 1800 may continue to output tactile sensations indicating source direction as long as the audio source localization and indication system 1800 detects the sound over the predetermined decibel level. Therefore, for example, if the user were in a quiet room and another person said something to the user at a normal conversational level, the audio source localization and indication system 1800 may output tactile sensations indicating direction in response to detecting the other person's speech if the speech is at a decibel level that is over the predetermined decibel level above the ambient noise level. In another example, if the user were in a relatively noisy room (e.g., a factory floor), the other person may need to raise their voice significantly such that their voice exceeds the requisite predetermined decibel level above the ambient noise level, in order to trigger the audio source localization and indication system 1800 outputting tactile sensations to indicate the direction of the other person's speech and thereby getting the user's attention. In the present example, as in the first example, the audio source localization and indication system 1800 may output tactile sensations for as long as the triggering event is occurring, or it may only output tactile sensations for a predetermined amount of time after the initial triggering event.

In a fourth example of a triggering event, a triggering event may be a new sound relative to recent sounds detected by the audio source localization and indication system 1800. For example, if a user is in an environment, such as a gathering, where there are many people talking simultaneously, and then a different type of sound occurs, such as a door squeaking as it is opened or a plate of food hitting the floor, the audio source localization and indication system 1800 may treat the different type of sound as a triggering event and alert the user to the direction of the source of the different type of sound. The different type of sound may be treated as a triggering event even though its decibel level may be at or below the ambient noise level.

In a fifth example of a triggering event, a triggering event may be a particular type of sound. For example, if the audio source localization and indication system 1800 detects speech, it may output tactile sensations indicating the direction of the speech. The audio source localization and indication system 1800 may output tactile sensations for as long as the speech is occurring, or it may only output tactile sensations for a predetermined amount of time after the speech source direction is initially indicated. The audio source localization and indication system 1800 may indicate a sound source direction every instance where a distinct speech source direction is attainable. For example, if a user is talking to several people in a group, the audio source localization and indication system 1800 may indicate direction each time a single speaker is discernable.

Other types of sounds may be treated as triggering events. For example, sirens, the sounds of vehicles running and/or moving, buzzers, bells, alarms, and/or any other appropriate sound may be programmed into the audio source localization and indication system 1800 as a triggering event.

In a sixth example of a triggering event, a triggering event may be particular elements of speech. That is, the audio source localization and indication system 1800 may be programmed to recognize particular words and then output tactile sensations to indicate to the user the direction from which the particular words originated. For example, the audio source localization and indication system 1800 may be programmed to recognize the user's name and/or words generally used to get someone's attention, such as "Hey", "Look out", and "Head's up", and then output tactile sensations indicating the direction of the triggering words.

In a seventh example of a triggering event, a triggering event may be programmed by the user. That is, the user may indicate to the audio source localization and indication system 1800 that a particular sound event is an event which the audio source localization and indication system 1800 should indicate a source direction. For example, a user who is a basketball player may select the sound of a bouncing basketball as a sound which should be considered a triggering event by the audio source localization and indication system 1800, thus enabling the user to track the position of the bouncing ball.

In an eighth example of a triggering event, a triggering event may the loudest sound detected by the audio source localization and indication system 1800. That is, the audio source localization and indication system 1800 may output tactile sensations to indicate to the user the direction from which the loudest sound currently detected by the audio source localization and indication system 1800 originated. In a variation, the loudest and the second loudest sounds detected by the audio source localization and indication system 1800 may be treated as triggering events.

Any other appropriate sound or decibel level (absolute or relative) may be treated as a triggering event by the audio source localization and indication system 1800. The above examples and other appropriate triggering events may be combined, added to, and/or modified as appropriate for any particular user's specific needs and/or preferences.

For example, a basketball player named Jake who can hear, but who does not have localization capabilities, may use the audio source localization and indication system 1800 programmed to treat the word "Jake" and the sound of a bouncing basketball as triggering events. In this regard, while playing basketball, Jake could be alerted as to the direction of anyone shouting his name and/or the bouncing ball.

Where the audio source localization and indication system 1800 has determined that a triggering event has occurred, and has determined the direction of the source of the triggering event, the direction determination may be of a general direction, such as to the left or to the right of the head of the user, or it may be more precise as discussed below in additional embodiments.

In a basic embodiment for completely deaf people, the audio source localization and indication system 1800 may only indicate that a particular sound occurred and not communicate direction. For example, the audio source localization and indication system 1800 may be configured to cause a tactile output whenever speech is detected or whenever speech is initially detected after a predetermined amount of time has passed without detected speech. In this regard, the audio source localization and indication system 1800 may alert a completely deaf person that speech is occurring, allowing them to search out the speaker and begin communicating with them (for example, through sign language). In such an embodiment, only one of the left unit 1801 and the right unit 1802 may be included.

In another embodiment, the audio source localization and indication system 1800 may make a determination of the direction of the source of a triggering event by determining which microphone (microphone 1803 or microphone 1804) first detected the triggering event and then causing the tactile output device on the same side as the first detecting microphone to vibrate, thereby indicating a direction to the user.

The output of such a system would be as described above with reference to chart 800 of FIG. 8.

In the present embodiment, for example, the left unit 1801 may detect sounds using the microphone 1803 and immediately send a signal via the communication module 1801 to the right unit that is representative of those sounds. The right unit 1802 may also be detecting sounds, and it may receive the signal from the left unit 1801 via the communication module 1904 and compare the sounds detected by the left unit 1801 to those detected by the right unit 1802. This comparison may be performed by the processor 1908 of the right unit 1802. When a triggering event is detected, the processor 1908 may compare the time of arrival of the triggering event to the left unit 1801 to the time of arrival of the triggering event to the right unit 1801 and then cause a tactile output at whichever unit 1801, 1802 first detected the triggering event. To facilitate such a comparison, the left and right units 1801, 1802 may periodically communicate with each other to synchronize clocks or other apparatus used to determine relative time of arrival of sounds. Also, the detected sounds by the left and right units 1801, 1802 may be time-stamped.

Using more complex analysis of sounds detected by each microphone 1803, 1804, the audio source localization and indication system 1800 may be operable to generate a more precise estimation of sound source direction. This direction determination may be in the form of a unique direction from 0 to 360 degrees within the transverse plane of the head of the user. Such localization with two microphones 1803, 1804 may be performed using beamforming techniques such as those used by Siemens Insio binax CIC hearing aids which use two CIC hearing aids with one microphone each. The unique direction may then be communicated to the user through any of the methodologies of to the two-tactile output device systems (directional indication system 100 and directional indication system 900) discussed above.

Figure 20:
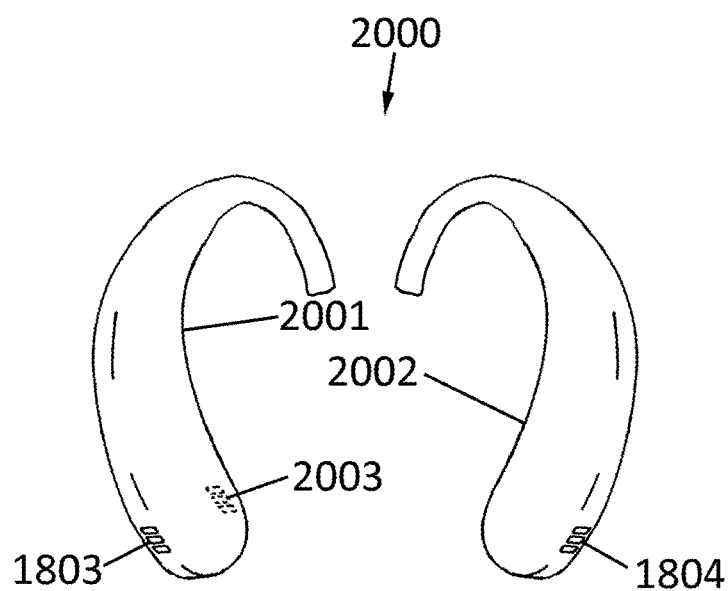
FIG. 20 is a perspective view of an audio source localization and indication system with three microphones that may be worn by a user.

In other embodiments, an audio source localization and indication system may be able to make more precise determinations of sound source direction through the use of one or more additional microphones. FIG. 20 is an illustration of an audio source localization and indication system 2000 similar to the audio source localization and indication system 1800 described above. The audio source localization and indication system 2000 comprises a left unit 2001 with a microphone 1803 and a right unit 2002 with a microphone 1804. Additionally, the audio source localization and indication system 2000 includes a third microphone 2003 located in the left unit 2001 (though alternately it may be placed within the right unit 2002). The third microphone 1804 may be used to help the audio source localization and indication system 2000 make a determination of direction within the transverse plane of the head of a user. This direction determination may be in the form of a unique direction from 0 to 360 degrees within the transverse plane of the head of the user. The unique direction may then be communicated to the user through any of the methodologies of to the two-tactile output device systems (directional indication system 100 and directional indication system 900) discussed above. The audio source localization and indication system 2000, with its third microphone 2003 is operable to discern between sources in front of and behind the user within the transverse plane of the head of the user based on time-of-arrival differences between all three microphones 1803, 1804, 2003. That is, for any particular set of arrival times of a triggering event, there will be only one directional solution within the transverse plane of the head of the user.

Figure 21:
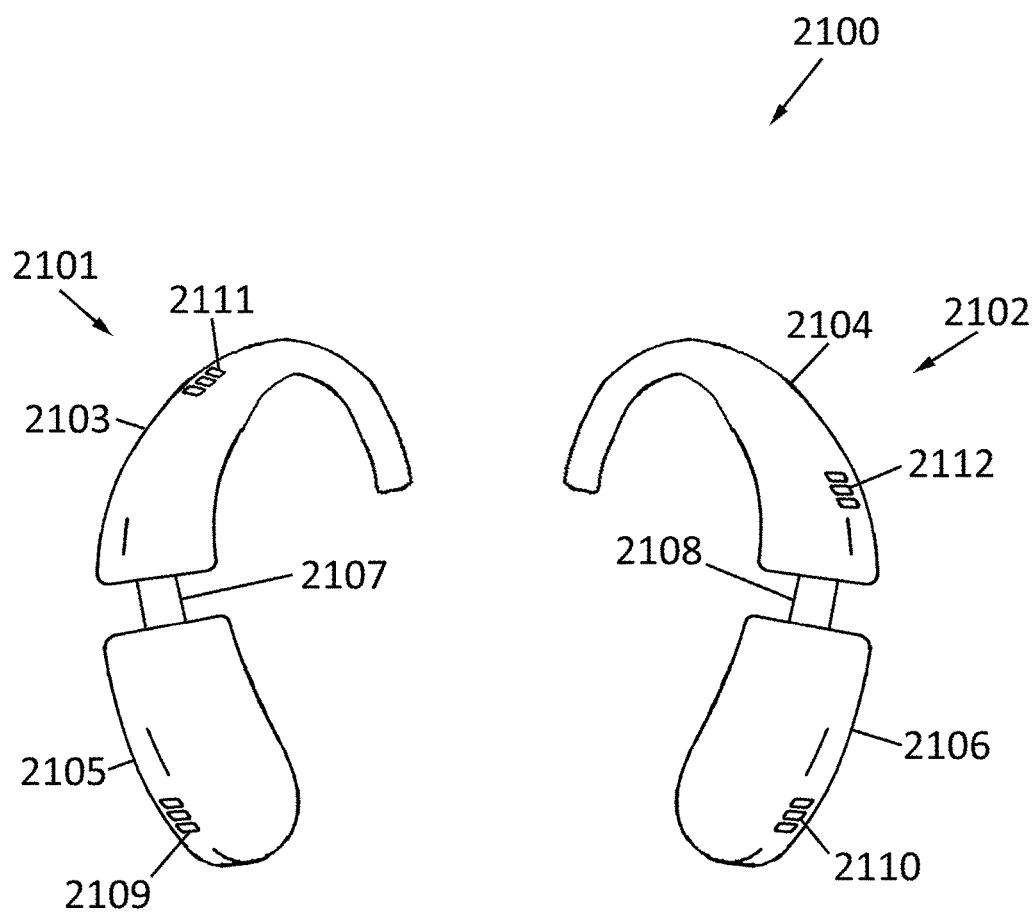
FIG. 21 is a perspective view of an audio source localization and indication system with vibration isolation and four microphones that may be worn by a user.

FIG. 21 is an illustration of a three-dimensional audio source localization and indication system 2100. The three-dimensional audio source localization and indication system 2100 is operable to determine a direction of an audio source in three dimensions and indicate that direction to a user. The three-dimensional audio source localization function is performed by incorporating the three-dimensional indication system 1000, described above, into the three-dimensional audio source localization and indication system 2100. The three-dimensional audio source localization and indication system 2100 may be used in similar applications as described above. In this regard, the three-dimensional audio source localization and indication system 2100 may inform the user of the direction, in three dimensions, from which a sound is originating.

The three-dimensional audio source localization and indication system 2100, comprises a left unit 2101 and a right unit 2102. Similar to the left 1001 and right 1002 units discussed above, the left 2101 and right 2102 units may be shaped and include features such that the left 2101 and right 2102 units may be worn behind the left and right ears, respectively, of a user. Other configurations and related methods of attaching devices to the ear of a user known to those skilled in the art may be incorporated in the three-dimensional audio source localization and indication system 2100.

The left unit 2101 includes an upper portion 2103 and a lower portion 2105. The upper portion 2103 and the lower portion 2105 are interconnected by an isolation link 2107. Similarly, the right unit 2102 includes an upper portion 2104 and a lower portion 2106. The upper portion 2104 and the lower portion 2106 are interconnected by an isolation link 2108. The left 2101 and right 2102 units may be configured in any appropriate variation, similar to as discussed above with respect to the left 1001 and right 1002 units.

Figure 22:
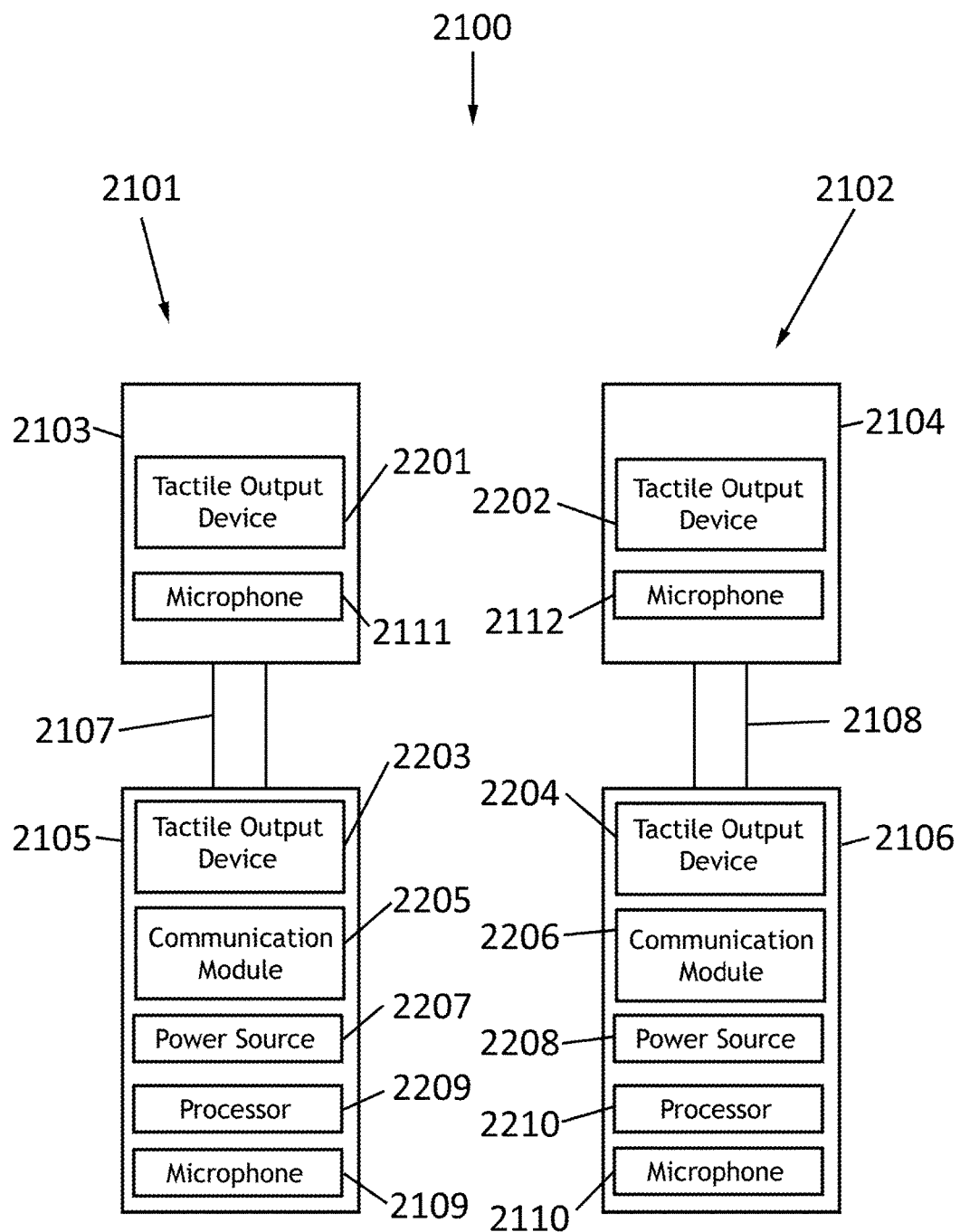
FIG. 22 is a functional block diagram of an audio source localization and indication system with vibration isolation and four microphones.

FIG. 22 is a block diagram of the three-dimensional audio source localization and indication system 2100 depicting components of the left 2101 and right 2102 units.

The left unit 2101 includes a tactile output device 2201 interconnected to the upper portion 2103 and a tactile output device 2203 interconnected to the lower portion 2105. The upper portion 2103 and the lower portion 2105 are interconnected to each other by the isolation link 2107. The right unit 2102 includes a tactile output device 2202 interconnected to the upper portion 2104 and a tactile output device 2204 interconnected to the lower portion 2106. The upper portion 2104 and the lower portion 2106 are interconnected to each other by the isolation link 2108. The tactile output devices 2201, 2202, 2203, 2204 are capable of independently producing a tactile output that a user wearing the left 2101 and right 2102 units can feel proximate to the user's left and right ears, respectively.

The isolation links 2107, 2108 function to vibrationally isolate the upper 2103, 2104 and lower 2105, 2106 portions from each other similar to as described above with respect to isolation links 1007, 1008.

The tactile output devices 2201, 2202, 2203, 2204 may be positioned and configured similar to tactile output devices 1201, 1202, 1203, 1204 discussed above. Moreover, together the tactile output devices 2201, 2202, 2203, 2204 are capable of communicating to the user a direction in three dimensions relative to the head of a user in a manner similar to as discussed with respect to tactile output devices 1201, 1202, 1203, 1204 of the three-dimensional directional indication system 1000 discussed above.

The left unit 2101 further includes a communication module 2205 and a power source 2207, and the right unit 2102 further includes a communication module 2206 and a power source 2208. The communication modules 2205, 2206 may function similarly as described with references to the communication modules 1205, 1206 of FIG. 12. Along the same lines, the left and right units 2101, 2102 may include processors 2209, 2210, respectively, which facilitate sound source direction determination and producing outputs at the tactile output devices 2201, 2202, 2203, 2204.

The power sources 2207, 2208 may be any appropriate source of power capable of powering the three-dimensional audio source localization and indication system 2100 similar to as described with respect to the power sources 1207, 1208.

The three-dimensional audio source localization and indication system 2100 may provide directional indications to users for any appropriate reason, similar to as discussed above with respect to the directional indication systems 100, 900 and the three-dimensional directional indication system 1000.

The three-dimensional audio source localization and indication system 2100 is operable to determine a three-dimensional direction of an audio source and indicate that direction to a user. Three-dimensional, as used herein, refers to a direction, relative to the head of a user that may be at any angle within the transverse plane of the head of the user or at any angle within the transverse plane and at any inclination or declination relative to the transverse plane. In this regard, three-dimensional encompasses an entire sphere around the head of the user.

Any appropriate features of the embodiments of the directional indication systems 100, 900, and the three-dimensional directional indication system 1000 discussed above may be incorporated in the three-dimensional audio source localization and indication system 2100 to provide directional indication to the user.

Returning to FIG. 21, the left unit 2101 further includes a microphone 2109 and a microphone 2111. As shown, the microphone 2109 may be in the lower portion 2105 and the microphone 2111 may be in the upper portion 2103. The microphones 2109, 2111 may be so disposed to provide separation between them in order to beneficially facilitate the determination of the direction of a sound source. In this regard, the more physical separation between the microphones, the greater the time difference between arrival of sound from a sound source, which may be beneficial in sound source determination. However, alternatively, the microphones may be placed within the same portion (upper 2103 or lower 2105). Similarly, the right unit further includes a microphone 2110 and a microphone 2112 in the lower portion 2106 and upper portion 2104, respectively. The microphones 2109, 2110, 2111, 2112 along with the processors 2209, 2210 may be used to determine a direction from which a sound is originating.

In general, the three-dimensional audio source localization and indication system 2100 will monitor sound being received by the microphones 2109, 2110, 2111, 2112 and, when a triggering event occurs, the three-dimensional audio source localization and indication system 2100 will output tactile sensations to the user via the tactile output devices 2201, 2202, 2203, 2204 to indicate the three-dimensional direction from which the triggering event occurred.

The three-dimensional audio source localization and indication system 2100 may determine the direction of a sound source by analyzing the sounds detected by each of the microphones 2109, 2110, 2111, 2112 and comparing the time of arrival at each of the microphones 2109, 2110, 2111, 2112 for a particular triggering event. The technique of analyzing time of arrival of a sound to determine a direction of a sound source is known to those skilled in the art. For example, military systems (e.g., Boomerang Systems from Raytheon) have used time of arrival analysis to determine source direction of incoming arms fire. For any particular triggering event detected, analyzing the time of arrival of the event at the four microphones 2109, 2110, 2111, 2112 will yield a single directional solution in three dimensions which can then be used to be the basis for the indication of direction to the user through the tactile output devices 2201, 2202, 2203, 2204, as described above with reference to the three-dimensional directional indication system 1000.

In this regard, the microphones 2109, 2110, 2111, 2112 may not all be positioned within a single plane, as such a single-plane configuration may have difficulty discerning the direction the sound source relative to the plane in which the microphones 2109, 2110, 2111, 2112 are located. That is, for example, if all of the microphones 2109, 2110, 2111, 2112 were disposed within the transverse plane of the head of the user, the three-dimensional audio source localization and indication system 2100 may have difficulty distinguishing between a sound source above the transverse plane from a sound source similarly positioned but below the transverse plane. Accordingly, the microphones 2109, 2110, 2111, 2112 may be positioned such that they all do not occupy the same plane. Such a configuration is illustrated in FIG. 21 where the microphone 2111 is positioned further forward (relative to the head of the user) than microphone 2112, while the other microphones 2109, 2110, 2112 generally are disposed in a plane parallel to the coronal plane, thus all four microphones 2109, 2110, 2111, 2112 are not is a single plane.

Accordingly, the microphones 2109, 2110, 2111, 2112 may be positioned within the three-dimensional audio source localization and indication system 2100 to produce relative positions between each other to aid in sound source direction detection. In this regard, some microphone positioning configurations may beneficially result in reduced processing loads and lower power processor consumption relative to other microphone positioning configurations.

To aid in sound source localization, the three-dimensional audio source localization and indication system 2100 may incorporate additional microphones to provide more data to facilitate directional determination. Any of the microphones 2109, 2110, 2111, 2112 may be directional microphones to further reduce processor burden and/or increase sound source direction accuracy and/or speed. Directional microphones are acoustic sensors known to those skilled in the art that are more responsive to sounds coming from certain directions as compared to other directions.

The audio source localization by the audio source localization and indication systems 1800, 2000, 2100 described herein may take into account portions of the HRTF. For example, when calculating direction, the audio source localization and indication systems 1800, 2000, 2100 may take into account the size of the user's head to interpret interaural time differences. Alternatively, these factors may be ignored to, for example, reduce direction calculation times.

Sound source localization may be beneficial even if the audio source localization and indication systems 1800, 2000, 2100 were only able to distinguish whether sound was coming from the left or the right side of the user thus enabling left/right indication as described with reference to FIG. 8. Relatedly, the audio source localization and indication systems 1800, 2000, 2100 may be beneficial to users even if their ability to localize sound is relatively coarse. For example, if an embodiment of the audio source localization and indication system 2000 is configured to determine sound source direction within +/−45 degrees, such a system would be beneficial to a user. Such accuracy would be beneficial since it would give a general indication to the user of the direction of the sound source, and the user may then respond by turning toward the sound source and then using visual clues to determine a more precise direction of the sound source. As human vision generally has a binocular field of view of about 120 degrees in the transverse and sagittal planes, a sound source direction accuracy of +/−45 degrees may allow the user to quickly locate the sound source. Sound source direction accuracies better than +/−45 degrees may be more beneficial in aiding sound source direction determination. In general, sound source direction accuracies may be balanced against other considerations, such as the speed at which the sound source direction is determined (e.g., processor load), power consumption, and/or system costs.

Figure 23:
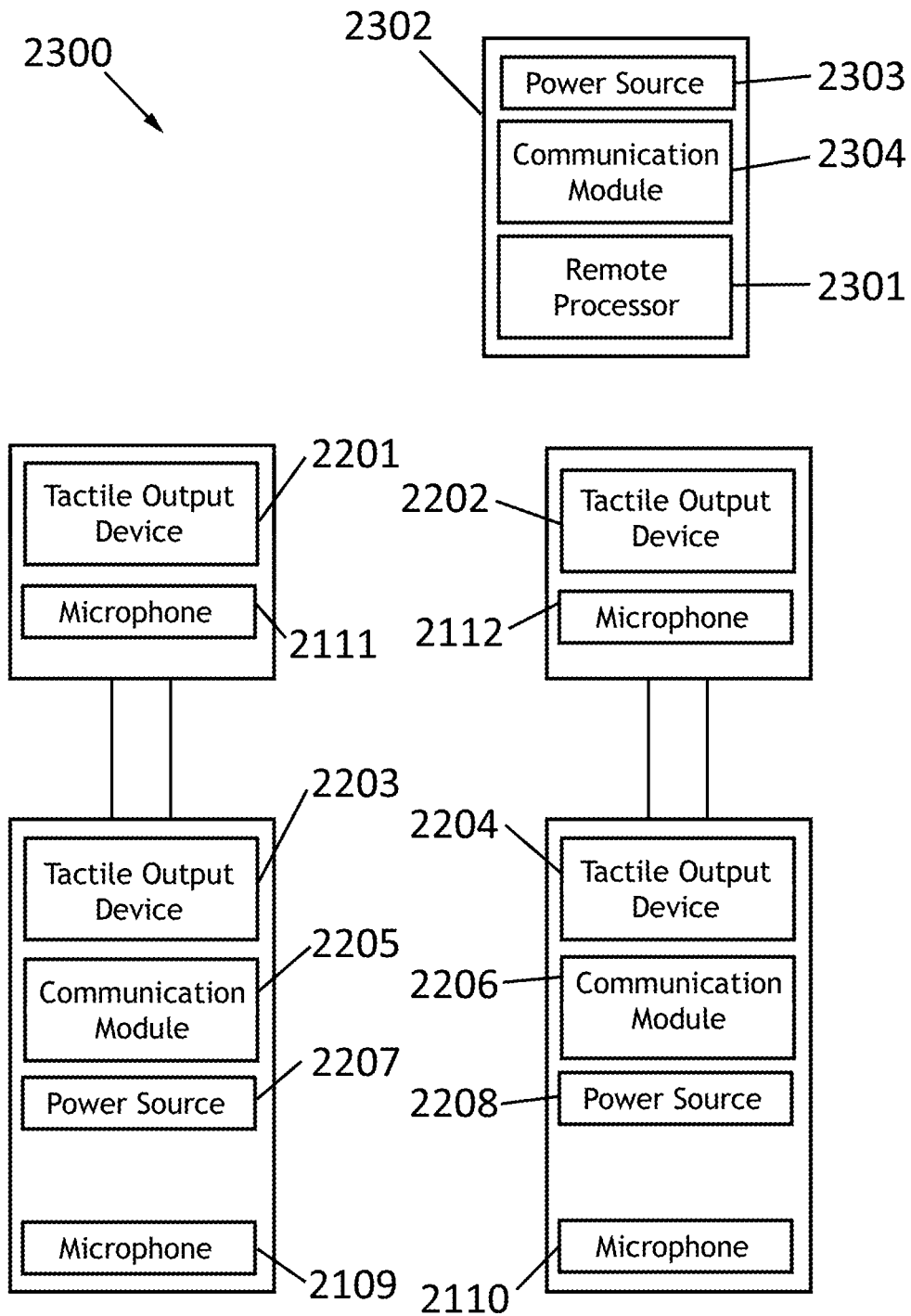
FIG. 23 is a functional block diagram of an audio source localization and indication system with vibration isolation, four microphones, and a remote unit.

The audio source localization and indication systems 1800, 2000, 2100 may be wireless systems configured as described above. Alternatively, as shown in an audio source localization and indication system 2300 FIG. 23, the processing described above as being performed by processors 1907, 1908, 2209, 2210 may be performed by a remote processor 2301. The audio source localization and indication system 2300 is similar to audio source localization and indication system 2100, but with a remote unit 2302 that contains the remote processor 2301, a power source 2303, and a communications module 2304. Locating the remote processor 2301 remotely may have the benefit of allowing a more powerful processor to be used to perform the direction determination calculations than would be possible with a processor sized to fit within units designed to be worn at the ears of the user. Such a more powerful remote processor 2301 may reduce system response time (the time between sound reaching the system and the system responding with tactile directional indications).

In an alternate embodiment of the audio source localization and indication system 2300, the system may be hard wired instead of using wireless communications. Such a system may not need the communication modules 2205, 2206, 2304 and power sources 2207, 2208 shown in FIG. 23.

In the audio source localization and indication systems 1800, 2000, 2100, 2300, the frequency of vibration produced by the tactile output devices may be independent of the frequency of the sound being localized. Also, the power level of vibration produced by the tactile output devices may be independent of the power of the sound being localized. Thus as previously discussed, the frequency of the vibration produced by the tactile output devices may, for example, be between about 100 Hz and 300 Hz regardless of the frequency of the sound source being localized. It is noted that the frequency of the vibration produced by the tactile output devices need not communicate any information to the user regarding the qualities (other than source direction) of the sounds which are being localized since the user (unless they are completely deaf) will be able to hear the sound that is being localized.

Figure 24:
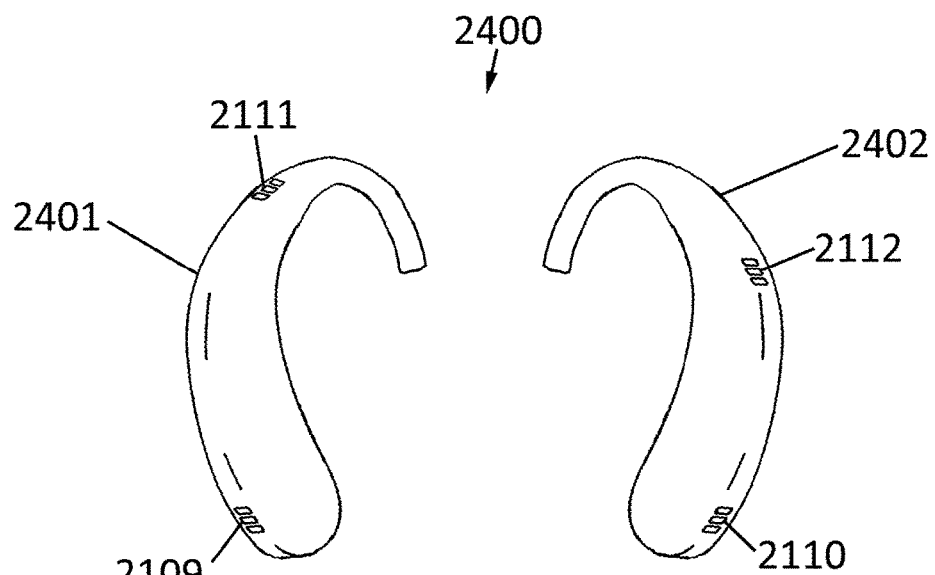
FIG. 24 is a perspective view of a three-dimensional directional indication system with four microphones that may be worn by a user.
Figure 25:
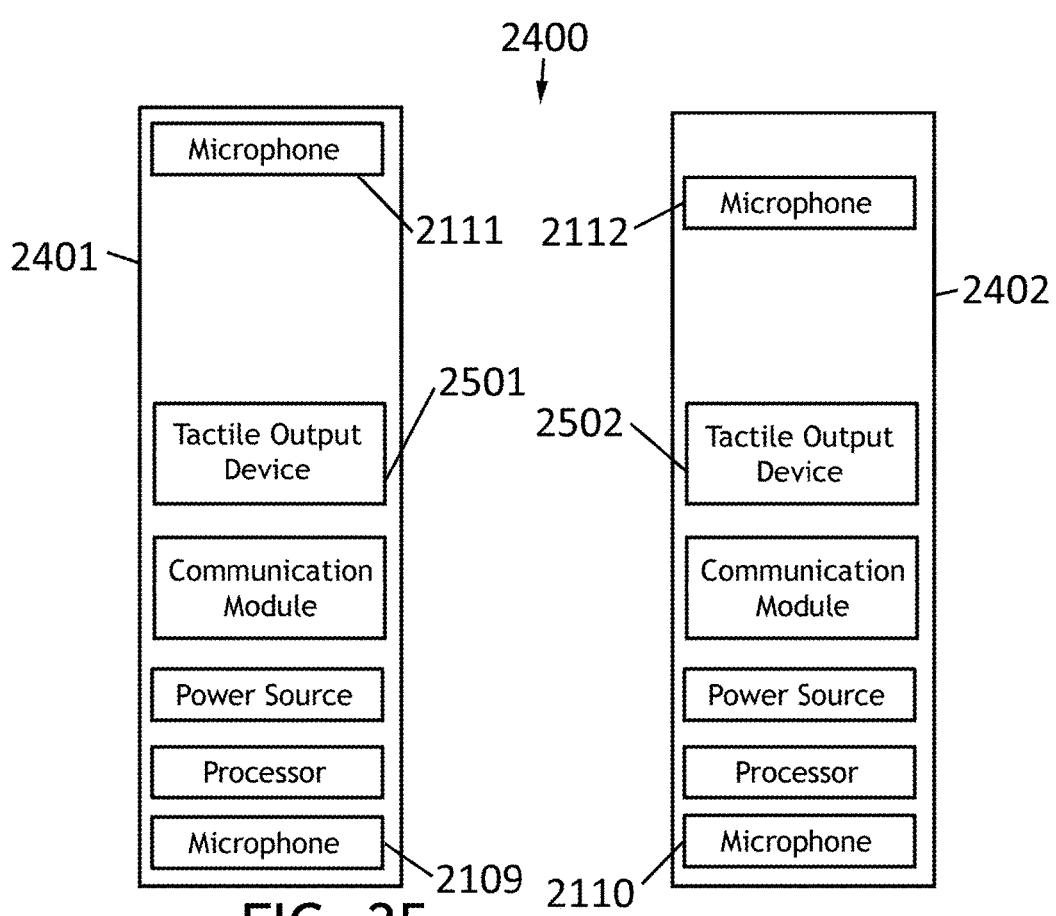
FIG. 25 is a functional block diagram of a three-dimensional audio source localization and indication system with four microphones that may be worn by a user.

In another embodiment of an audio source localization and indication system 2400 as shown in FIGS. 24 and 25, the audio source localization and indication system 2400 is capable of determining a three-dimensional direction of a sound source similarly to as discussed above in various embodiments. This determination may be achieved, for example, through the use of four microphones 2109, 2110, 2111, 2112. The microphones 2109, 2110, 2111, 2112 are disposed similarly to the microphones in the audio source localization and indication system 2100 shown in FIG. 21 with two microphones 2109, 2111 in a left unit 2401 and two microphones 2110, 2112 in a right unit 2402. However, in place of using four tactile output devices to communicate a three-dimensional direction, the audio source localization and indication system 2400 uses two tactile output devices, a tactile output device 2501 and a tactile output device 2502. The audio source localization and indication system 2400 may indicate direction as described above with reference to the three-dimensional directional indication system 1600. That is, the directional indication is accomplished by varying the frequency of the output of the tactile output devices 2501, 2502 to communicate the inclination or declination of the sound source direction while communicating the angle of direction within the transverse plane of the head of the user in a manner similar to as discussed with respect to directional indication systems 100, 900.

Accordingly, for example, in an embodiment where the indication of elevation is governed by Equation Set 4 and the indication is of angle within the transverse plane is governed by Equation Set 1, a sound source direction of 315 degrees within the transverse plane of the head of the user at an elevation of 45 degrees would be indicated by a left tactile output of 50 percent of maximum set power and a right tactile output of 0 percent of maximum set power with both tactile output devices 2501, 2502 operating at 250 Hz. In another example, where the indication of elevation is governed by Equation Set 4 and the indication is of angle within the transverse plane is governed by Equation Set 1, a sound source direction of 100 degrees within the transverse plane of the head of the user at an elevation of −20 degrees (i.e., 20 degree declination) would be indicated by a left tactile output of 11 percent of maximum set power and a right tactile output of 100 percent of maximum set power with both tactile output devices 2501, 2502 operating at 178 Hz.

The audio source localization and indication systems 1800, 2000, 2100, 2300, 2400 and variations thereof discussed herein may, for example, be worn by a person with SSD. In this regard, the person with SSD may adequately hear sounds in his environment, but may lack localization capabilities without assistance. Thus by wearing an audio source localization and indication system, the person with SSD may quickly be able to localize sound using input from the audio source localization and indication system.

The audio source localization and indication systems 1800, 2000, 2100, 2300, 2400 and variations thereof discussed herein may, for example, be worn by individuals who use one or two hearing aids and lack normal sound localization capabilities. That is, an audio source localization and indication system may be worn along with one or two hearing aids. For example, an audio source localization and indication system may be worn behind both ears of an individual who is also wearing ITE (In The Ear) hearing aids.

Figure 26:
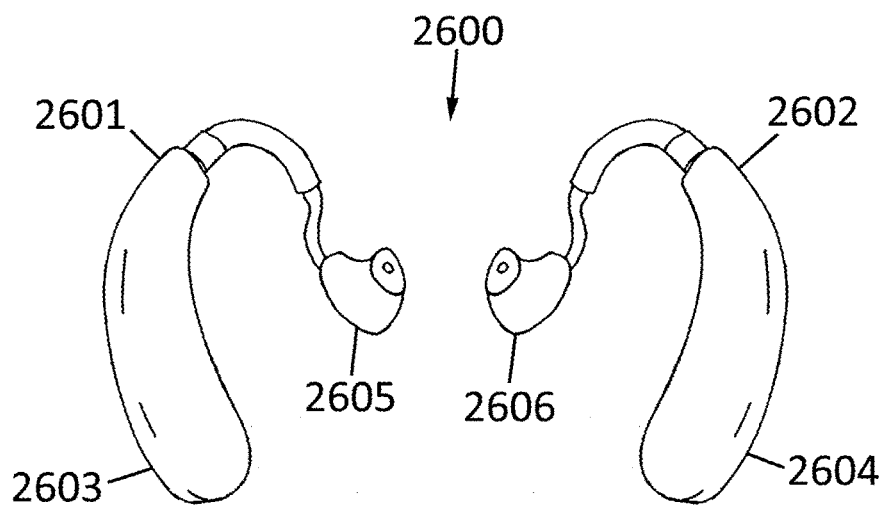
FIG. 26 is a perspective view of hearing aid system that may be worn by a user.

FIG. 26 is an illustration of a hearing aid system 2600 that incorporates an audio source localization and indication system (any one of audio source localization and indication systems 1800, 2000, 2100, 2300, or 2400 or any associated embodiment) as described herein. The hearing aid system 2600 includes a left unit 2601 and a right unit 2602. The left unit 2601 includes a left housing 2603 which may house the electronics of the incorporated audio source localization and indication system along with any electronics and elements necessary for the hearing aid system 2600 to function as a hearing aid or hearing aids. The right unit 2602 includes a right housing 2604 which may house the electronics of the incorporated audio source localization and indication system along with electronics and elements necessary for the hearing aid system 2600 to function as a hearing aid or hearing aids.

In systems where the left unit 2601 delivers amplified sound to the left ear of the user, the left unit 2601 may further include a left earmold 2605 capable of being inserted into the left ear of the user. Similarly, in systems where the right unit 2602 delivers amplified sound to the right ear of the user, the right unit 2602 may further include a right earmold 2606 capable of being inserted into the right ear of the user. The earmolds 2601, 2602 may be custom molded specifically to fit within the ears of a particular user as is common in the art.

The hearing aid system 2600 may be configured as a crossover hearing aid system for users with SSD, a single amplifying hearing aid for users with unilateral hearing loss, or two amplifying hearing aids for users with bilateral hearing loss. Users who use any of these types of hearing aids may have difficulty locating the direction of a sound source as hearing aids may not aid in localization and may mask, reduce or eliminate the aural clues needed for sound localization.

Figure 27:
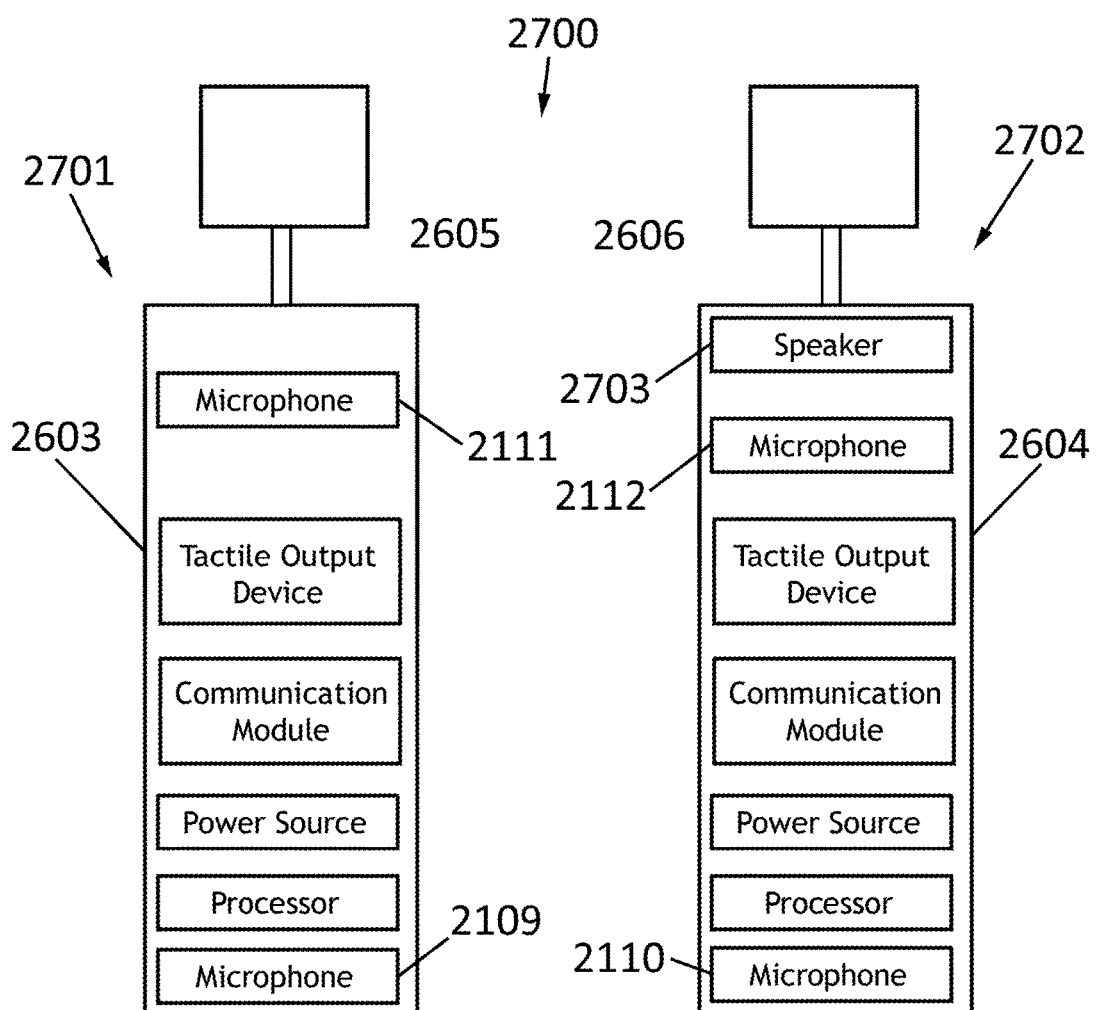
FIG. 27 is a functional block diagram of a crossover hearing aid system that may be worn by a user.

The hearing aid system 2600 may be configured as a crossover hearing aid system 2700 as illustrated in FIG. 27, where one of a left unit 2701 or a right unit 2702 may be a sound producing unit and the other of the left unit 2701 or right unit 2702 may be a sound detecting unit. The crossover hearing aid system 2700 is configured for a person who is deaf in their left ear. In the crossover hearing aid system 2700, the left unit 2701 may be operable to detect sound that arrives at the left unit 2701 via a microphone (the microphone may be one of the microphones 2109, 2111 or it may be an additional microphone for the crossover function) within the left unit 2701, and transmit a signal to the right unit 2702 representative of the sound received by the left unit 2701. The right unit 2702 may receive the signal from the left unit 2701 and produce an audio output via an audio output device such as a speaker 2703 to the user through the right earmold 2606, wherein the audio output is based on the received signal. The speaker 2703 is a device that turns electrical signals into audio output and is sometimes referred to in the art as a receiver. In this regard, sounds that arrive at the left ear of the user may be heard in the right ear of the user. The audio output to the user may be filtered (for example, to filter out background noise to make speech clearer) as is known to those skilled in the art. While operating as crossover hearing aids, the crossover hearing aid system 2700 may also operate as any one of audio source localization and indication systems 1800, 2000, 2100, 2300, or 2400 or any associated embodiments thereof. The crossover hearing aid system 2700 is shown in FIG. 27 as including the audio source localization and indication system 2400. Thus the crossover hearing aid system 2700 may provide both crossover hearing aid functions and sound localization indication.

Figure 28:
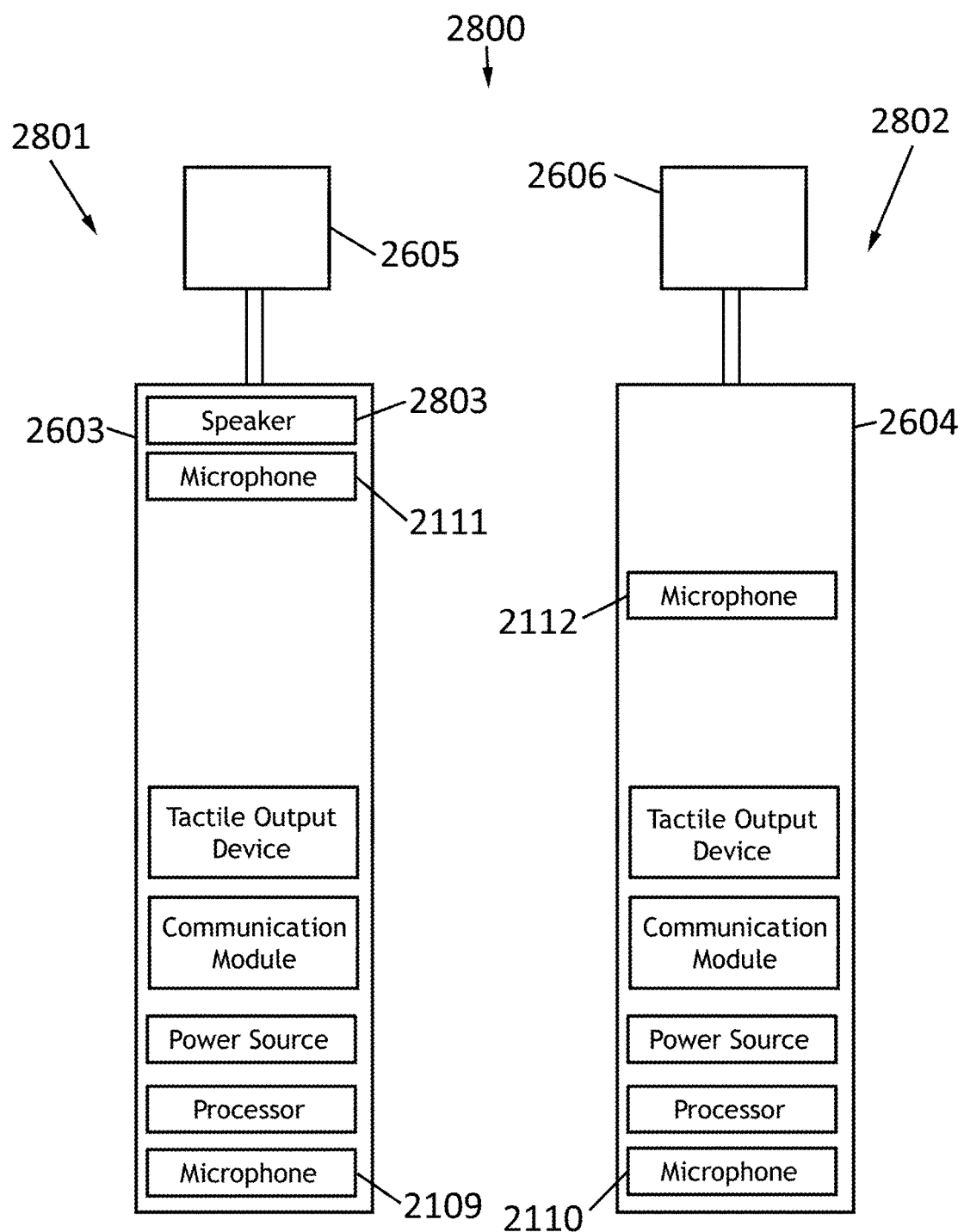
FIG. 28 is a functional block diagram of a single amplifying hearing aid system that may be worn by a user.

The hearing aid system 2600 may be configured as a single amplifying hearing aid system 2800 as illustrated in FIG. 28, where one of a left unit 2801 or a right unit 2802 may function as an amplifying hearing aid. The single amplifying hearing aid system 2800 is configured for a person who has hearing loss in their left ear. In the single amplifying hearing aid system 2800, the left unit 2801 may be operable to detect sound that arrives at the left unit 2801 via a microphone (the microphone may be one of the microphones 2109, 2111 or it may be an additional microphone for the amplification function) within the left unit 2801, and produce an amplified audio output via a speaker 2803 to the user through the left earmold 2605, wherein the audio output is based on the received signal. The audio output to the user may be filtered or manipulated (for example, to match the amplified audio signal to the frequencies where the user has hearing loss) as is known to those skilled in the art. While operating as a single amplifying hearing aid, single amplifying hearing aid system 2800 may also operate as any one of audio source localization and indication systems 1800, 2000, 2100, 2300, or 2400 or any associated embodiments thereof. The single amplifying hearing aid system 2800 is shown in FIG. 28 as including the audio source localization and indication system 2400. Thus the single amplifying hearing aid system 2800 may provide both single ear hearing aid functions and sound localization indication.

Figure 29:
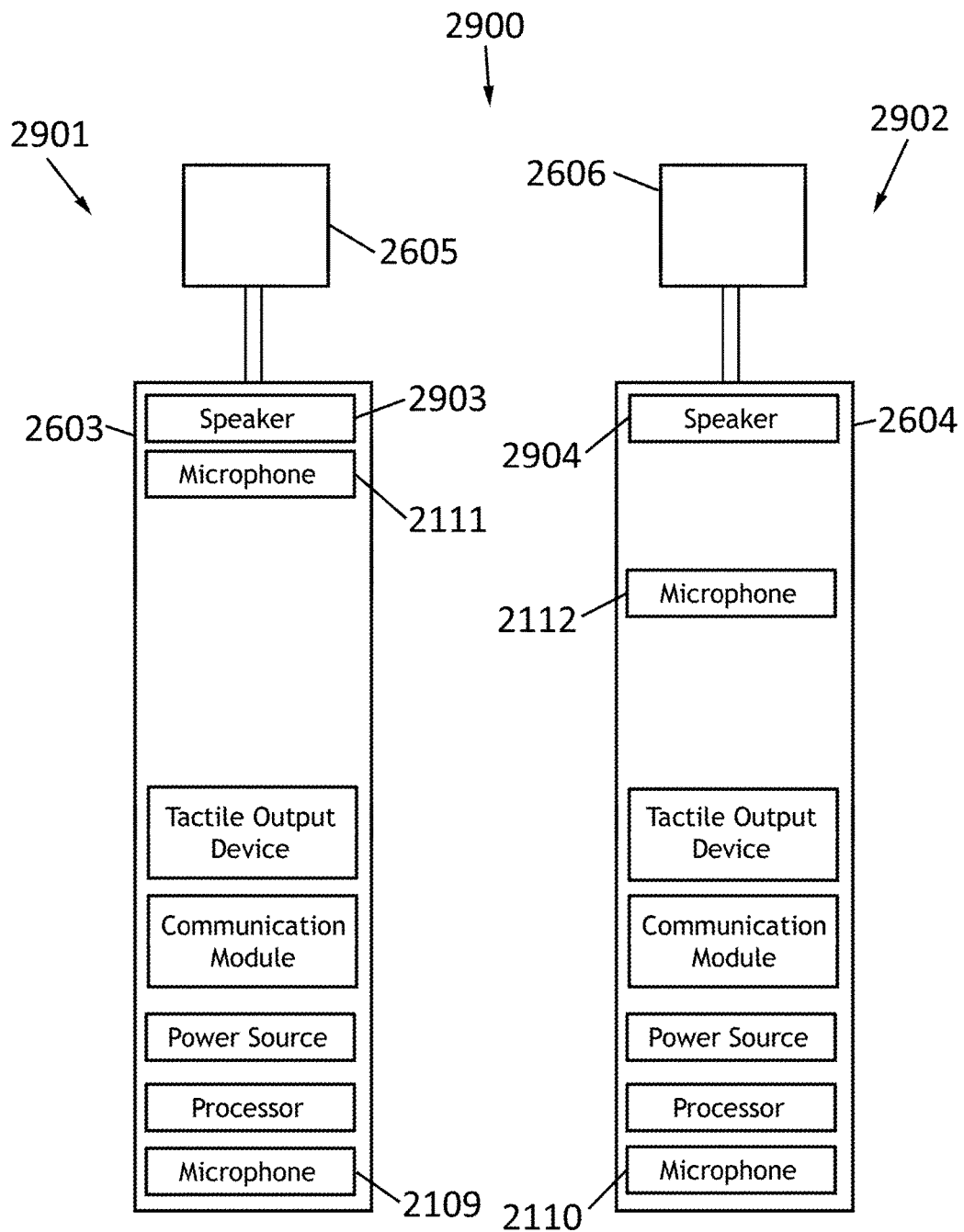
FIG. 29 is a functional block diagram of a dual amplifying hearing aid system that may be worn by a user.

The hearing aid system 2600 may be configured as a dual amplifying hearing aid system 2900 as illustrated in FIG. 29, where both a left unit 2901 and a right unit 2902 function as amplifying hearing aids. The dual amplifying hearing aid system 2900 is configured for a person who has hearing loss in both ears. In the dual amplifying hearing aid system 2900, the left unit 2901 may be operable to detect sound that arrives at the left unit 2901 via a microphone (the microphone may be one of the microphones 2109, 2111 or it may be an additional microphone for the amplification function) within the left unit 2901, and produce an amplified audio output via a speaker 2903 to the user through the left earmold 2605, wherein the audio output is based on the received signal. Similarly, the right unit 2902 may be operable to detect sound that arrives at the right unit 2902 via a microphone (the microphone may be one of the microphones 2110, 2112 or it may be an additional microphone for the amplification function) within the right unit 2902, and produce an amplified audio output via a speaker 2904 to the user through the right earmold 2606, wherein the audio output is based on the received signal. The audio outputs to the user may be filtered or manipulated (for example, to match the amplified audio signal to the frequencies where the user has hearing loss in each ear) as is known to those skilled in the art. While operating as dual amplifying hearing aids, the dual amplifying hearing aid system 2900 may also operate as any one of audio source localization and indication systems 1800, 2000, 2100, 2300, or 2400 or any associated embodiments thereof. The dual amplifying hearing aid system 2900 is shown in FIG. 29 as including the audio source localization and indication system 2400. Thus the dual amplifying hearing aid system 2900 may provide both dual ear hearing aid functions and sound localization indication.

Figure 30:
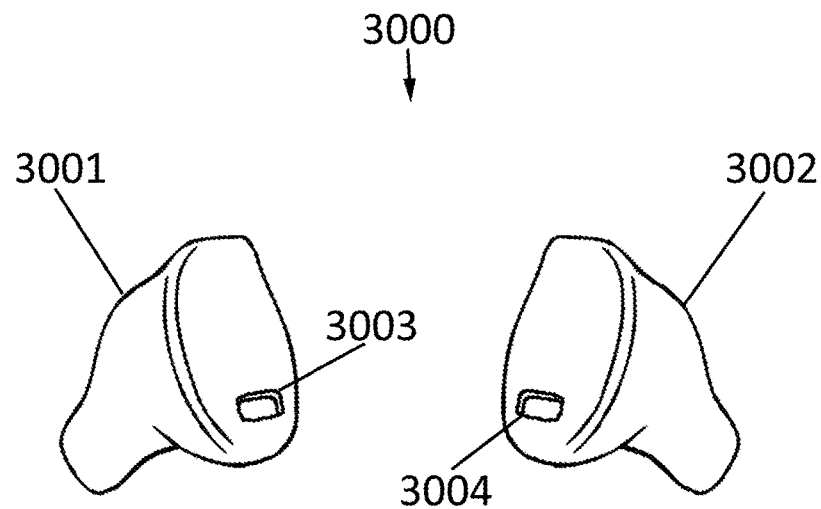
FIG. 30 is a perspective view of an ITE (In The Ear) dual amplifying hearing aid system that may be worn by a user.

The systems shown in FIGS. 1, 2, 10, 11, 16, 18, 20, 21, 24, and 26 are configured to be worn behind the ear (BTE). However, any of these systems or combination of systems may be of any appropriate configuration or combination of configurations typically used in hearing aids. These configurations include completely in the canal (CIC) systems, in the canal (ITC) systems, and ITE systems. For example, FIG. 30 is an illustration of an ITE dual amplifying hearing aid system 3000 that incorporates the embodiment of the audio source localization and indication system 1800 that is operable to produce tactile outputs as described above with reference to chart 800 of FIG. 8. The ITE dual amplifying hearing aid system 3000 includes a left unit 3001 and a right unit 3002 that are configured to fit within the left and right ears, respectively, of a user. The left unit 3001 includes a microphone 3003. The right unit 3002 includes a microphone 3004

Figure 31:
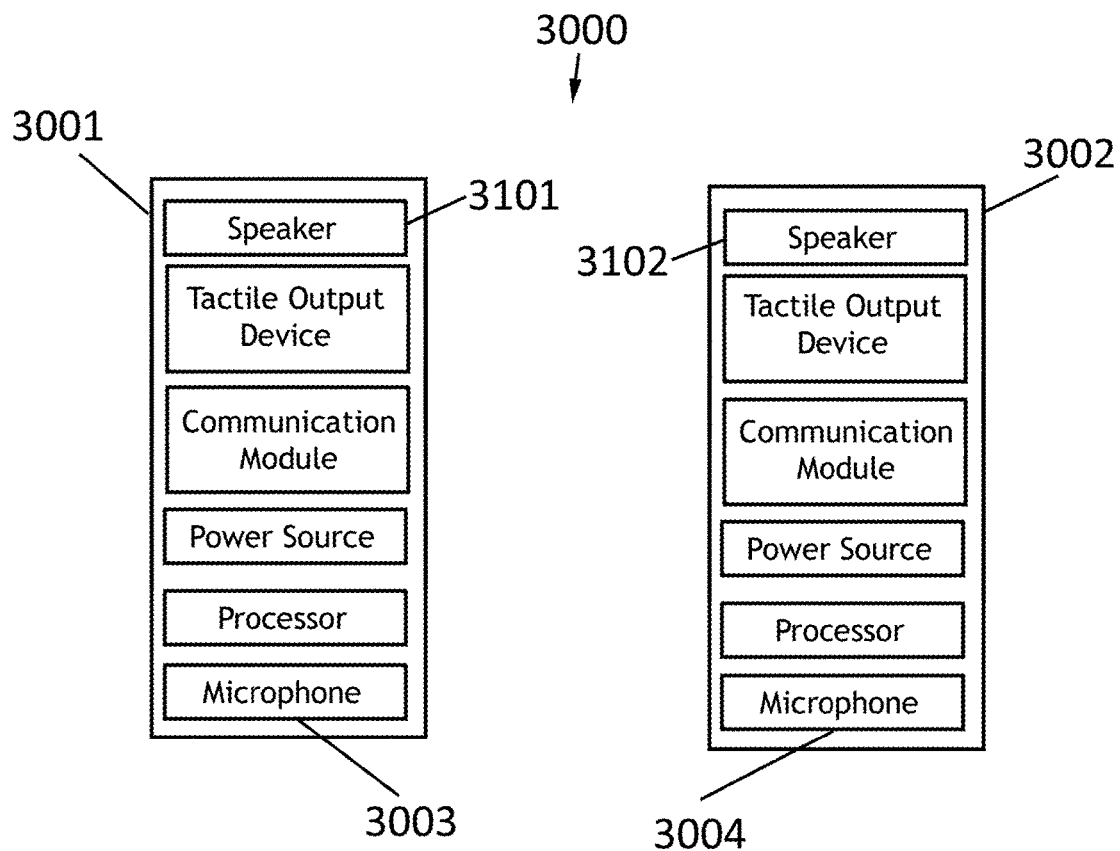
FIG. 31 is a functional block diagram of an ITE dual amplifying hearing aid system that may be worn by a user.

FIG. 31 is a block diagram of the ITE dual amplifying hearing aid system 3000. The ITE dual amplifying hearing aid system 3000 includes components for producing amplified audio signals at a left speaker 3101 and a right speaker 3102. The ITE dual amplifying hearing aid system 3000 further includes components for audio source localization and directional indication. Thus, the ITE dual amplifying hearing aid system 3000 simultaneously performs typical hearing aid functions and localization functions.

In a variation of the ITE dual amplifying hearing aid system 3000, the ITE dual amplifying hearing aid system 3000 may include additional microphones and/or may be capable of determining the direction of a sound source in three-dimensions. Such a system may be operable to indicate a three-dimensional direction to the user using variable frequencies to represent elevation as discussed above with reference to audio source localization and indication system 2400.

The hearing aids systems discussed herein may incorporate any appropriate hearing aid technology. For example, the hearing aid functions discussed herein may be performed using analog components, digital components, or any appropriate combination thereof.

Variations of the systems discussed herein may be wireless or hard wired. Where the systems are wireless, the wireless communication may use any appropriate method, including, but not limited to Bluetooth and WiFi.

Variations of the systems discussed herein may have portions of the systems disposed remotely. The remote portions may be interconnected wirelessly or through wiring.

FIG. 32 is an illustration of a crossover hearing aid system 3200 that incorporates a tactile output device to alert a user of a fault in the crossover hearing aid system 3200. As previously noted, the crossover hearing aid system is a hearing aid system that detects sounds at the deaf ear of a person with SSD, transmits information regarding the detected sounds to a hearing aid at the functioning ear of the SSD person, and then plays sounds based on the detected sounds into the functioning ear of the SSD person. FIG. 33 is a block diagram of the crossover hearing aid system 3200. The crossover hearing aid system 3200 is configured for a person who is deaf in the left ear. An opposite configuration may be used for an individual deaf in the right ear. Accordingly, a left unit 3201 includes a microphone 3301 for detecting sound at the left ear and a communication module 3303 for transmitting information regarding the detected sound to a right unit 3202. The left unit 3201 further includes a power source 3305 and a processor 3307. The right unit 3202 receives the transmitted information at a communication module 3304 and plays an audio stream based on the received information through a speaker 3302. As known in the art, the played audio stream may be modified to make selected sounds clearer, such as speech. The right unit 3202 further includes a power source 3306 and a processor 3308.

The left unit 3201 may include an earmold 3205. However, the earmold 3205 may be used solely to secure the left unit 3201 to the user since in this example the user is deaf in the left ear. The communication module 3303, the power source 3305, the processor 3307, the microphone 3301, and a tactile output device 3309 may all be disposed within a left housing 3203 of the left unit 3201.

The right unit 3202 may include an earmold 3206 to direct the sound produced by the speaker 3302 into the ear canal of the user and to help secure the right unit 3202. The communication module 3304, the power source 3306, the processor 3308, and the speaker 3302 may all be disposed within a right housing 3204 of the right unit 3202.

In the crossover hearing aid system 3200, the right unit 3202 may alert the user when a fault condition exists, such as a loss of communication with the left unit 3201. The loss of communication may be due to the power source 3305 of the left unit 3201 being depleted (such as a drained battery) below a predetermined level. The loss of communication may be due to the left unit 3201 being out of communication range, possibly due to it falling off of the user or the user removing the left unit 3201. The alert produced by the right unit 3202 may be in the form of a specific audible tone that the user may recognize as an alert.

In traditional crossover hearing aid systems, if the unit for the hearing ear experiences a depleted battery or falls off of the user, there is no way for the unit for the deaf ear to alert the user of the fault. This may be particularly problematic when the unit for the hearing ear falls off the user, since any delay between the unit for the hearing ear falling off and the user recognizing that it has fallen off may greatly increase the chances of losing the unit for the hearing ear. It is particularly important for active people and children to quickly recognize that the unit for the hearing ear has fallen off since significant distances or movement may occur between the time the unit for the hearing ear falls off and the user notices that the unit for the hearing ear has fallen off. The user may not immediately recognize that the unit for the hearing ear has fallen off for many reasons, such as an extremely noisy environment, an extremely quiet environment, or where the system was particularly tuned to boost speech and no speech was present.

In the crossover hearing aid system 3200, the left unit 3202 may alert the user when a fault condition exists by causing the tactile output device 3309 to produce a tactile sensation at the left ear of the user. Thus, if the right unit 3202 were to fall off of the user, the left unit 3201 may immediately alert the user, allowing the user to immediately look for the right unit 3202.

The tactile output device 3309 may be any appropriate device for producing a physical sensation felt by a user. For example, the tactile output device 3309 may be a vibration device of any appropriate type, such as an eccentric rotating mass vibration motor, a linear resonant actuator, a moving coil transducer, or a piezoelectric transducer. The vibration created by the tactile output device 3309 may be of any appropriate frequency.

In an embodiment, the tactile output device 3309 may be a speaker capable of outputting sound at a level such that it produces a tactile sensation that can immediately be detected by the user. For example, a low frequency, high decibel sound produced by the tactile output device 3309 may be felt by the user despite it being transmitted to the deaf ear. Such a low frequency, high decibel sound may be heard by the hearing ear of the user due to the sound being transmitted to the hearing ear through bone conduction. By making the sound produced a distinct signal, such as producing the sound at regular intervals, the user may immediately recognize the sound as the crossover hearing aid system 3200 signaling a fault situation.

To be able to signal when the right unit 3202 loses communication with the left unit 3201, the left unit 3201 may be in regular communication with the right unit 3202. This communication may be in the form of a signal being transmitted from the communication module 3304 of the right unit 3202 to the communication module 3303 of the left unit 3201 at regular intervals, and a lack of receiving the signal by the left unit 3201 may be interpreted as a fault.

As noted, the crossover hearing aid system 3200 of FIG. 33 is configured for a person who is deaf in the left ear. A configuration for a person who is deaf in the right ear would be similar with the internal components and functions of the left 3201 and right 3202 switched.

The function and associated components described with reference to the crossover hearing aid system 3200 alerting a user when the unit for the hearing ear has fallen off may be incorporated into any appropriate system discussed herein. For example, the left and right units 101,102 of the directional indication system 100, may be in contact with each other and when they lose contact (for example, due to out of communication range or battery depletion), they may each produce a tactile sensation alerting the user to the fault, or in the case where one of the power sources is depleted below a predetermined level, the other unit may produce a tactile sensation alerting the user to the fault.

The systems described above that include microphones may be configured to detect and indicate direction of sounds outside the normal hearing range of humans. For example, the systems may be configured to detect and indicate direction of a 30 kHz tone. In this regard, directional information may be communicated to a wearer of the system without anyone but the wearer being aware of the communication. Such a feature may be used, for example, by a child user who is separated from their parent in a crowded area. The parent may activate an intermittent 30 kHz tone and the system worn by the child may in response indicate the direction of the source of the tone, leading the child back to the parent.

Figure 34:
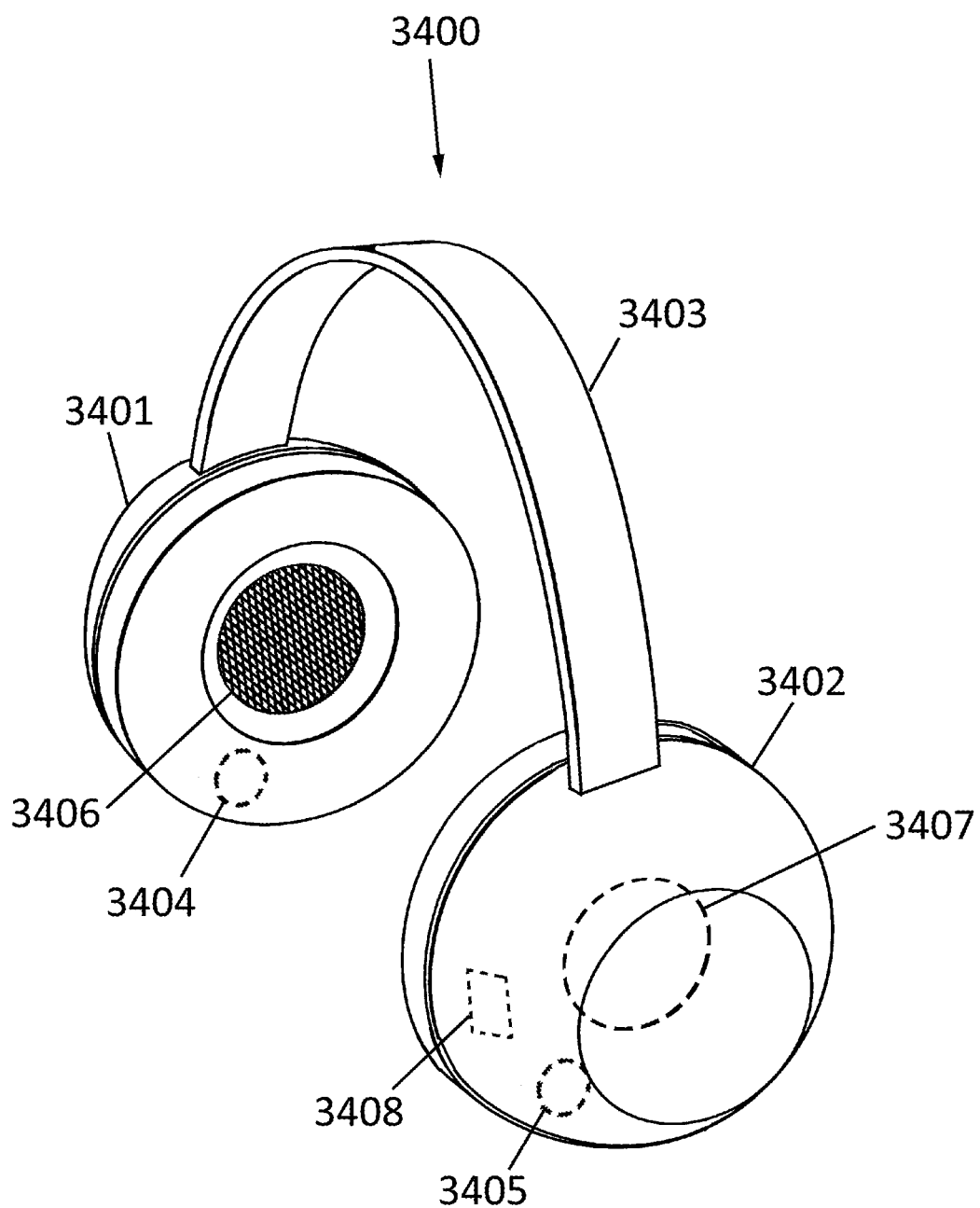
FIG. 34 is a perspective view of headphones that may be worn by a user.

The systems described above may, where appropriate, be incorporated into headphones 3400 as illustrated in FIG. 34 that are configured to deliver audio and tactile information to a user. Such headphones 3400 may be of any appropriate configuration, such as the headphones 3400 shown including a first portion 3401 and a second portion 3402 configured to fit over or against the ears of the user with an interconnecting portion 3403 that interconnects the first 3401 and second 3402 portions and enables the headphones 3400 to be secured to the user's head. The first portion 3401 includes a first tactile output device 3404 configured to deliver a tactile output to the first ear. The second portion 3402 includes a second tactile output device 3405 configured to deliver a tactile output to the second ear. The first portion 3401 may further include a first speaker 3406 and/or the second portion 3402 may further include a second speaker 3407. Additional tactile outputs may also be included. Other known headphone configurations may be used, such as headphones including two portions that may be partially inserted in the ears (often referred to as earbuds) which may also include members to help secure the partially inserted portions to the user's ears. Such headphones 3400 may be configured to deliver audio information and include one of the described directional indication systems 100, 900. The audio may be stereo or the audio may be mono (i.e., where the same audio information is delivered to each of the portions configured to fit over, against, or in the ears of the user). Headphones 3400 using stereo may, for example, be used by a user with normal hearing who seeks a more immersive experience that may be delivered through use of the tactile output devices 3404, 3405. Headphones 3400 using mono may, for example, be worn by a user with SSD, thereby delivering the full audio information to the user's hearing ear while delivering directional information through the tactile output devices 3404, 3405 proximate to both ears. Alternatively, headphones 3400 using mono may be configured to only deliver the audio to one ear of the user (i.e., the hearing ear for a user with SSD).

The headphones 3400 may further include a processor 3408, configured to cause tactile output from at least one of the first 3404 and second 3405 tactile output devices indicative of a direction relative to the user. The processor 3408 may be configured to determine the tactile outputs to be produced based on an audio stream provided to the headphones 3400. In this regard, the processor 3408 may be operable to receive a stereo audio stream, analyze the stream to determine which sounds are to be accompanied by tactile outputs, and cause the determined tactile outputs to be produced by the first 3404 and second 3405 tactile output devices. Thus the headphones 3400 may be a standalone system that when provided a stereo audio stream may be capable of producing tactile outputs indicative of the direction of stereo elements within the audio stream.

Such a system incorporated into headphones may be incorporated into video gaming systems. Many video gaming systems use stereo sound to communicate locations of various elements with the games. For example, an explosion to the right of the player may be heard primarily through a right speaker or right portion of a headset. However, a player with SSD and/or difficulty localizing sounds may not be able to receive this information through audio communication. By incorporating one of the described directional indication systems 100, 900 into headphones and using such directional indication systems 100, 900 to communicate the direction of the various elements within the video game, the player with SSD and/or difficulty localizing sounds may receive directional information, thus enabling an improved gaming experience.

Figure 35:
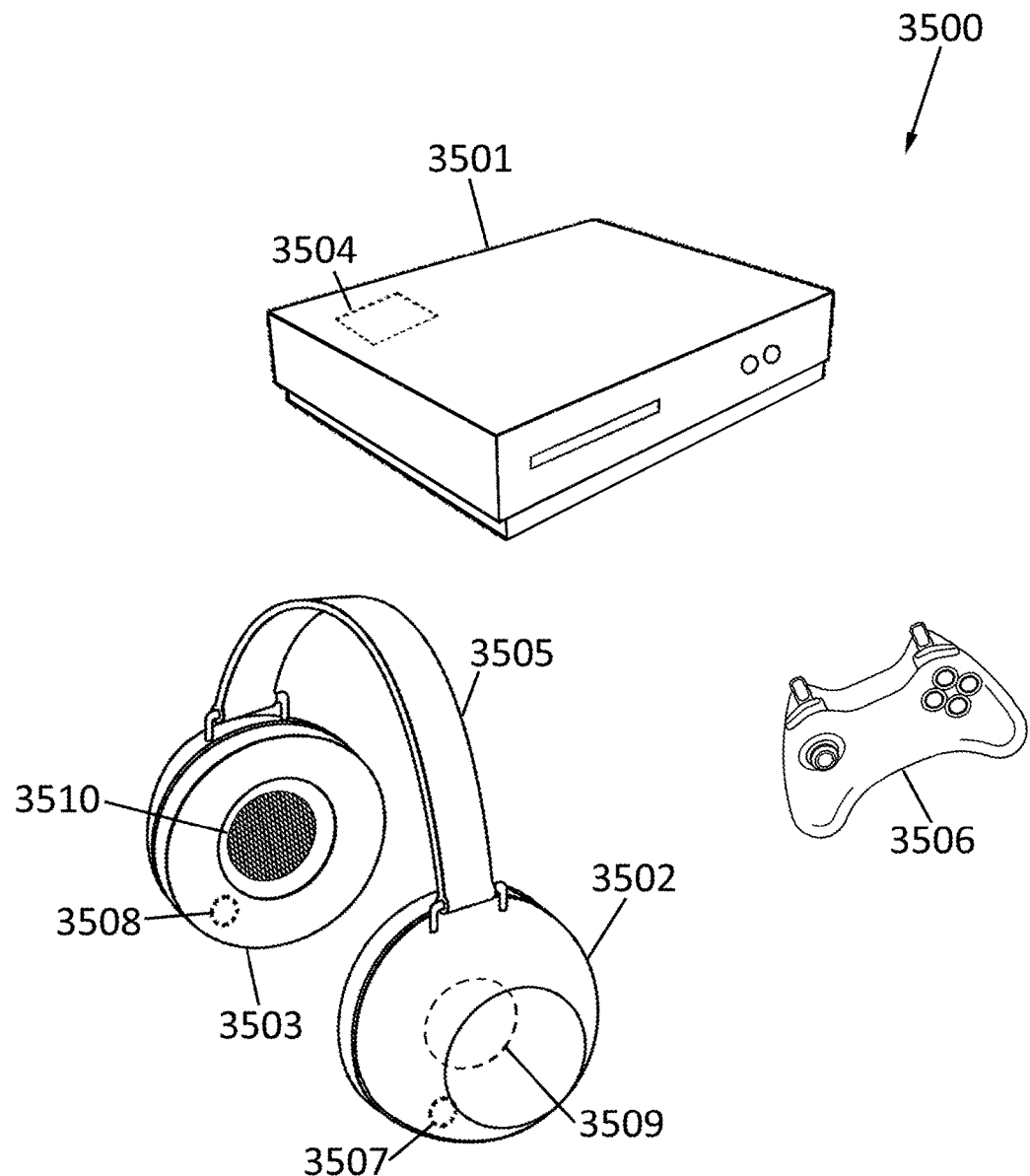
FIG. 35 is a perspective view of a video game system.

Such a video game system 3500 is illustrated in FIG. 35. The video game system 3500 includes a video game console 3501, a first unit 3502 configured to be worn at a first ear of a user, a second unit 3503 configured to be worn at a second ear of the user, and a processor 3504. As shown, the first 3502 and second 3503 units may be configured as a headphone system 3505. The video game system 3500 may include any other components, such as a controller 3506, that may be part of video game systems. The processor 3504 may be disposed within the video game console 3501 as illustrated, or it may be disposed at any appropriate location, such as within one of or both of the first 3502 and second 3503 units. The first unit 3502 includes a first tactile output device 3507 configured to deliver a tactile output to the first ear. The second unit 3503 includes a second tactile output device 3508 configured to deliver a tactile output to the second ear. The processor 3504 is configured to cause tactile output from at least one of the first 3507 and second 3508 tactile output devices indicative of a direction relative to the user. The first unit 3502 may further include a first speaker 3509 and/or the second unit 3503 may further include a second speaker 3510. The video game system 3500 may operate in a stereo mode or the video game system 3500 may operate in a mono mode where the first 3509 and second 3510 speakers deliver the same audio information. While in either stereo or mono mode, directional information may be provided by the first 3507 and/or second 3508 tactile output devices.

Any of the systems described above may include the ability to disable and enable the tactile output devices and/or other features. This may be accomplished by physically interfacing with components of the system, such as pressing a button or manipulating a switch on a component of the system, or it may be done remotely through a wireless interface. The remote device may be a dedicated remote, it may be a device, such as a phone or tablet, with wireless communications capabilities, or it may be any other appropriate device.

Any of the systems described above may include the ability to store system parameters in a memory. The system parameters may include triggering events, directional indication schemes, personal preferences, and/or hearing aid parameters. Such memory may be of any appropriate form.

Any of the sound localization techniques and components discussed herein may be modified where appropriate to incorporate other localization technologies. For example, beamforming techniques that may be able to make directional determinations with two or three microphones may be substituted for the four-microphone techniques discussed herein.

The systems described above may include additional components and have additional capabilities beyond those disclosed. The hearing aid systems may include additional features for hearing aid systems known to those skilled in the art.

Figure 36:
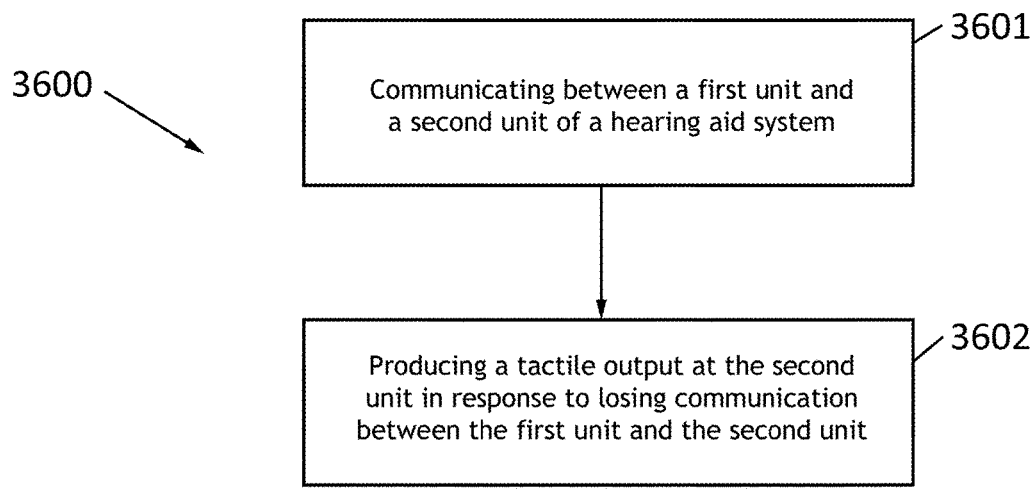
FIG. 36 is a flowchart of a method of operating a hearing aid system that includes using a tactile output to notify a user of a loss of communication.

FIG. 36 is a flowchart 3600 of a method of operating a hearing aid system. The hearing aid system includes a first unit and a second unit configured to be worn proximate to the left and right ears of a user. The first step 3601 includes communicating between the first unit and the second unit. Such communication may occur through a wireless or wired connection between the first and second units. The next step 3602 includes producing a tactile output at the second unit in response to losing communication between the first unit and the second unit. The producing step may include producing a tactile output at a frequency and power level that is independent of any sound proximate to the hearing aid system. The tactile output may be created by a vibration device of any appropriate type, such as an eccentric rotating mass vibration motor, a linear resonant actuator, a moving coil transducer, or a piezoelectric transducer. The tactile output may be created by a low frequency audio output at a decibel level such that the output can be felt by a user wearing the second unit independent of whether or not the user can hear the output from the second unit. The low frequency audio output frequency may be independent of any sound proximate to the hearing aid system.

Figure 37:
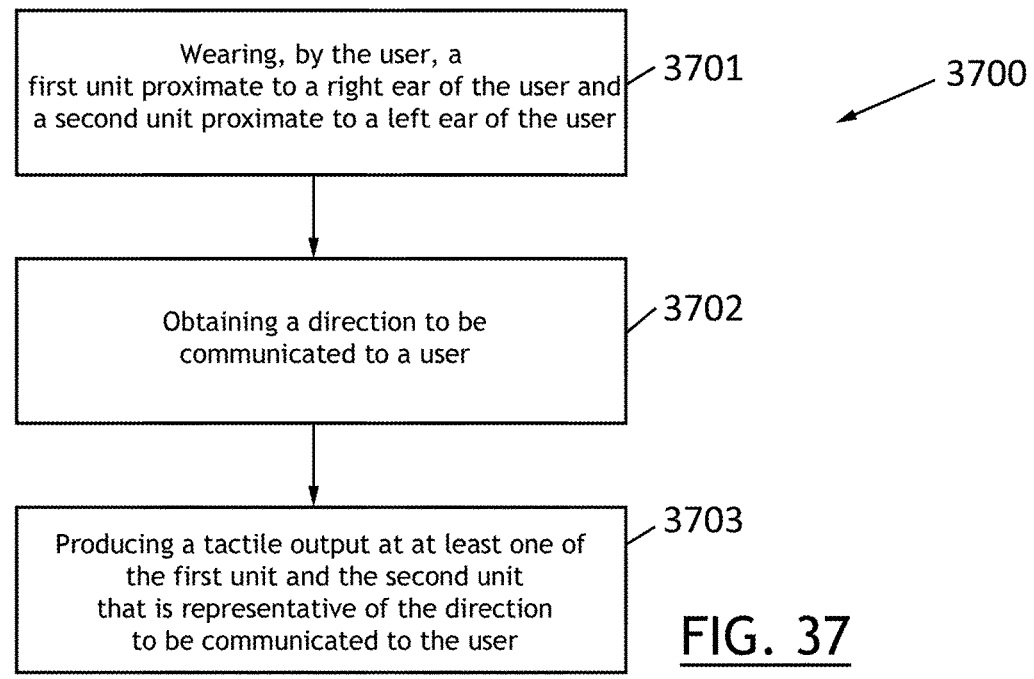
FIG. 37 is a flowchart of a method of transmitting directional information to a user.

FIG. 37 is a flowchart 3700 of a method of transmitting directional information to a user. The first step 3701 includes wearing, by the user, a first unit proximate to a right ear of the user and a second unit proximate to a left ear of the user. The next step 3702 includes obtaining a direction to be communicated to a user. The direction may be related to the direction of a sound source, the direction of interest in a video game or virtual reality application, or any other appropriate situation where it is appropriate to communicate a direction to the user. The direction obtained in step 3702 may be obtained by the first unit and/or second unit, or it may be obtained from a source external to the first and second units. The next step 3703 includes producing a tactile output at at least one of the first unit and the second unit that is representative of the direction to be communicated to the user. The tactile output frequency and power level may be independent of any sound proximate to the hearing aid system. The tactile outputs of the first and second units may be produced such that the direction to be communicated to the user is three-dimensional relative to the head of the user. A frequency of the tactile output may be a function of the elevation of the direction to be communicated to the user relative to the head of the user.

In a variation of the method of FIG. 37, the producing a tactile output step includes producing tactile output at two locations proximate to the right ear of the user and producing tactile output at two locations proximate to the left ear of the user. The tactile outputs of the first and second units are performed such that the direction to be communicated to the user is three-dimensional relative to the head of the user.

Figure 38:
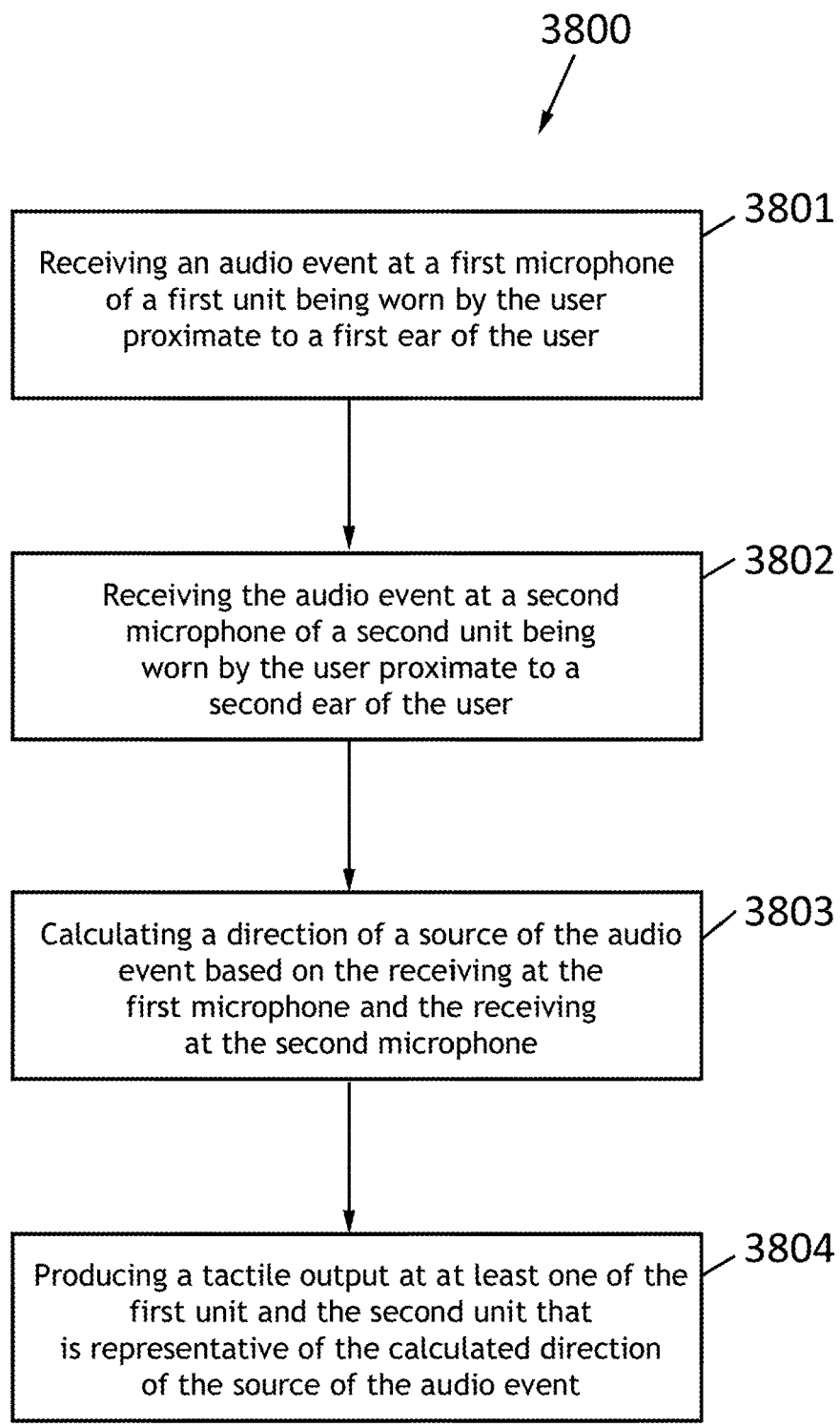
FIG. 38 is a flowchart of a method for transmitting sound location information to a user.

FIG. 38 is a flowchart 3800 of a method for transmitting sound location information to a user. The first step 3801 includes receiving an audio event at a first microphone of a first unit being worn by the user proximate to a first ear of the user. The second step 3802 includes receiving the audio event at a second microphone of a second unit being worn by the user proximate to a second ear of the user. The delay between the receiving of the first step 3801 and the receiving of the same audio event in the second step 3802 is due to the ITD of the audio event. That is, the first unit receives the audio event before the second unit. In this regard, whichever unit being worn by the user that receives the audio event first is considered the first unit, whether it is being worn at the left ear or the right ear of the user.

The next step 3803 includes calculating a direction of a source of the audio event based on the receiving at the first microphone and the receiving at the second microphone. That is, calculating the direction of the source of the audio event based on audio received in steps 3801 and 3802.

The next step 3804 includes producing a tactile output at at least one of the first unit and the second unit that is representative of the calculated direction of the source of the audio event. The tactile output frequency and power level may be independent of any sound proximate to the hearing aid system. The tactile outputs of the first and second units may be produced such that the direction to be communicated to the user is three-dimensional relative to the head of the user.

In a first variation of the method of FIG. 38, the method may further include receiving the audio event at a third microphone. In such a variation, the calculating a direction step may be based on the receiving at the first, second and third microphones. Such a calculation may provide for a single solution in the two dimensional transverse plane of the head of the user. In a variation of the first variation, the method may further include receiving the audio event at a fourth microphone and the calculating a direction step may be based on the receiving at the first through fourth microphones. In this embodiment, the calculating a direction may determine a three-dimensional direction, relative to the head of the user, of the audio event.

In a second variation of any of the above variations of the method of FIG. 38, a frequency of the tactile output may be a function of the elevation of the direction of the source relative to the head of the user. In a third variation of the method of FIG. 38 or of the first variation thereof, the producing a tactile output step includes producing tactile output at two locations proximate to the right ear of the user and producing tactile output at two locations proximate to the left ear of the user. The tactile outputs of the first and second units are performed such that the direction to be communicated to the user is three-dimensional relative to the head of the user.

In a fourth variation of any of the above variations of the method of FIG. 38, the method may further include receiving an audio stream by the first unit, transmitting data representative of the audio stream from the first unit to the second unit, and then producing an audio output by the second unit according to the transmitted data. Thus in the current variation, the method may perform sound source localization and directional indication along with crossover hearing aid system functions.

In a fifth variation of any of the first through third variations of the method of FIG. 38, the method may further include amplifying, by the first unit, sound received by the first unit. In this regard, the method may include the first unit functioning as a typical hearing aid. In a variation of the fifth variation, the method may further include amplifying, by the second unit, sound received by the second unit. In this regard, the method may include the first and second units functioning as typical hearing aids.

In a sixth variation of any of the variations of the method of FIG. 38, the frequency and power level of the tactile output representing the calculated direction of the source of the audio event may be independent of the frequency and power of the audio event.

Figure 39:
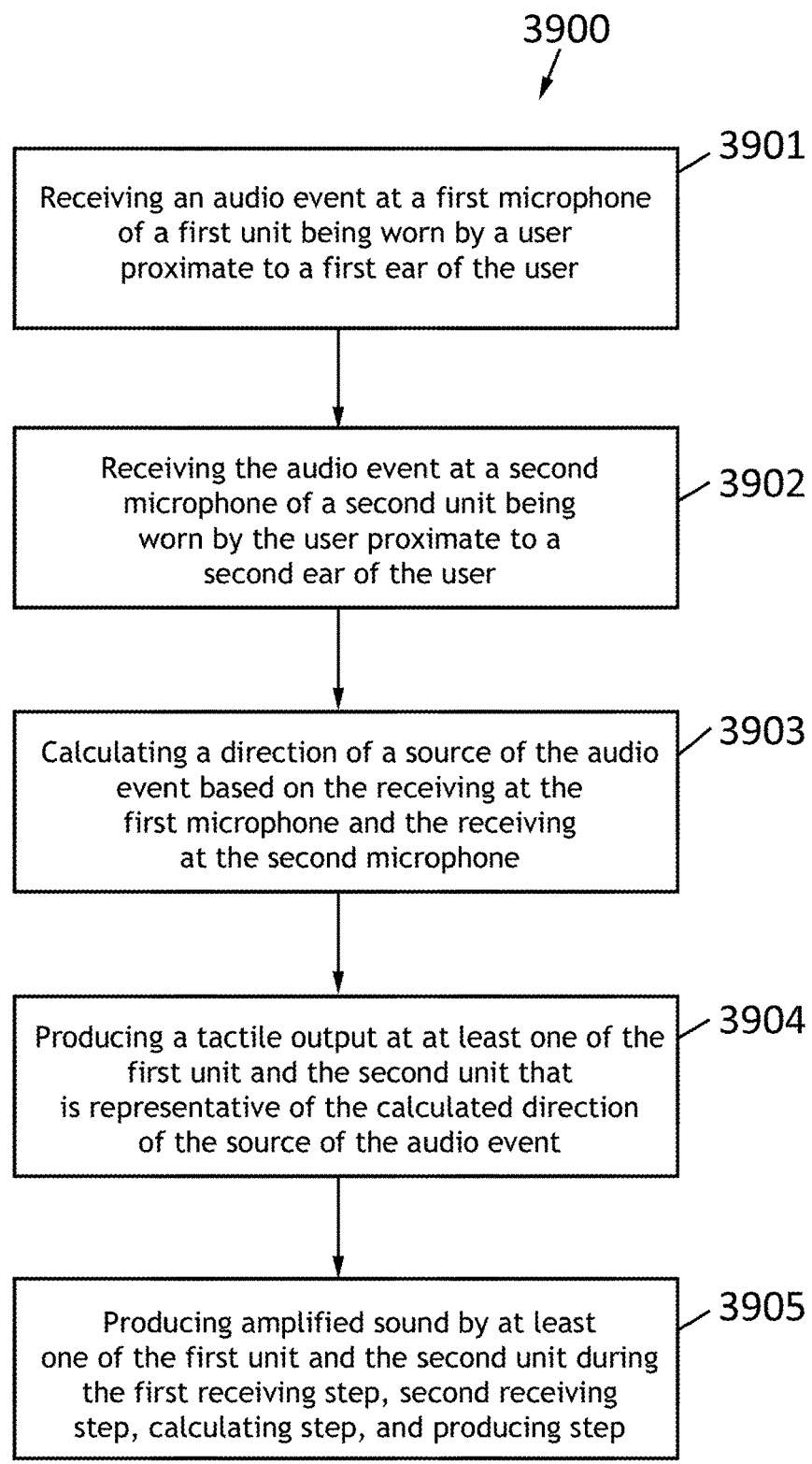
FIG. 39 is a flowchart of a method for operating a hearing aid system that includes producing tactile outputs representative of a direction of a source of an audio event.

FIG. 39 is a flowchart 3900 of a method for operating a hearing aid system. The first step 3901 includes receiving an audio event at a first microphone of a first unit being worn by a user proximate to a first ear of the user. The second step 3902 includes receiving the audio event at a second microphone of a second unit being worn by the user proximate to a second ear of the user. The delay between the receiving of the first step 3901 and the receiving of the same audio event in the second step 3902 is due to the ITD of the audio event. That is, the first unit receives the audio event before the second unit. In this regard, whichever unit being worn by the user that receives the audio event first is considered the first unit, whether it is being worn at the left or right ear of the user.

The next step 3903 includes calculating a direction of a source of the audio event based at least in part on the receiving at the first microphone and the receiving at the second microphone. That is, calculating the direction of the source of the audio event based at least in part on audio received in steps 3901 and 3902. The next step 3904 includes producing a tactile output at at least one of the first unit and the second unit that is representative of the calculated direction of the source of the audio event. The tactile output frequency and power level may be independent of any sound proximate to the hearing aid system. The tactile outputs of the first and second units may be produced such that the direction to be communicated to the user is three-dimensional relative to the head of the user.

The next step 3905 includes producing amplified sound by at least one of the first unit and the second unit during the first receiving step, second receiving step, calculating step, and producing step. Thus the method includes operating as a hearing aid system during the direction determination and indication functions.

In a variation of the method of FIG. 39, a frequency of the tactile output may be a function of the elevation of the direction of the source relative to the head of the user.

The foregoing written description of the invention enables one skilled in the art to make and use what is considered presently to be the best mode thereof. Additional variations, combinations, and equivalents of the specific embodiments, methods, and examples described herein will be apparent to those skilled in the art. Such modifications and extensions are intended to be within the scope of the present invention as defined by the claims that follow. The invention should therefore not be limited by the above described variations, embodiments, methods, and examples, but by all variations, embodiments and methods within the scope and spirit of the invention.

What is claimed is:

1. A directional information communication system comprising:
   a first unit configured to be worn at a first ear of a user, the first unit comprising a first tactile output device configured to deliver a tactile output to the first ear, wherein said tactile output to the first ear is operable to produce a tactile sensation at the first ear of the user;
   a second unit configured to be worn at a second ear of the user, the second unit comprising a second tactile output device configured to deliver a tactile output to the second ear, wherein said tactile output to the second ear is operable to produce a tactile sensation at the second ear of the user; and
   a processor configured to cause tactile output from at least one of the first and second tactile output devices according to directional information received by the directional information communication system such that a direction is operable to be communicated to the user through said tactile sensation at the first ear of the user and said tactile sensation at the second ear of the user, wherein said direction corresponds to said directional information received by the directional information communication system.

2. The directional information communication system of claim 1, wherein the first unit further comprises a first audio output device, wherein the second unit further comprises a second audio output device, and wherein the directional information communication system is a headphone set operable to produce audio streams at each ear of the user wearing the directional information communication system.

3. The directional information communication system of claim 1, further comprising:
   a microphone; and
   an audio output device, wherein the audio output device is operable to produce an amplified audio stream according to sound received by the microphone.

4. The directional information communication system of claim 3, wherein the first tactile output device is a vibrator that comprises at least one of an eccentric rotating mass vibration motor, a linear resonant actuator, and a piezoelectric transducer, and wherein the second tactile output device is a vibrator that comprises at least one of an eccentric rotating mass vibration motor, a linear resonant actuator, and a piezoelectric transducer.

5. The directional information communication system of claim 1, wherein said tactile sensation at the first ear of the user is operable to produce a tactile sensation at a pinna of the left ear of the user, wherein said tactile sensation at the pinna of the left ear of the user is operable to communicate to the user a direction to the left of the user, and wherein said tactile sensation at the second ear of the user is operable to produce a tactile sensation at a pinna of the right ear of the user, wherein said tactile sensation at the pinna of the right ear of the user is operable to communicate to the user a direction to the right of the user.

6. An audio source localization aid system comprising:
   a first unit configured to be worn at a first ear of a user, the first unit comprising:
      a first microphone;
      a first tactile output device configured to deliver a tactile output to the first ear; and
      a first communication module;
   a second unit configured to be worn at a second ear of the user, the second unit comprising:
      a second microphone;
      a second tactile output device configured to deliver a tactile output to the second ear; and
      a second communication module configured to communicate with the first communication module, wherein the first communication module is configured to communicate with the second communication module; and a processor configured to determine source location information of sound received by the audio source localization aid system based on sound received by the first and second microphones, the processor also configured to cause a tactile output from at least one of the first and second tactile output devices according to the determined source location information, wherein said tactile output from at least one of the first and second tactile output devices is indicative of direction and is of a frequency that is independent of the frequency of sound received by the audio source localization aid system.

7. The audio source localization aid system of claim 6, wherein the first unit further comprises a first audio output device, wherein the audio source localization aid system is configured for a user with unilateral hearing loss, wherein the second unit is operable to transmit a first data stream to the first unit, wherein the first data stream is representative of sound received by the second microphone, and wherein the first audio output device is configured to produce an audio stream according to the first data stream.

8. The audio source localization aid system of claim 7, wherein the first tactile output device is a vibrator that comprises at least one of an eccentric rotating mass vibration motor, a linear resonant actuator, and a piezoelectric transducer, and wherein the second tactile output device is a vibrator that comprises at least one of an eccentric rotating mass vibration motor, a linear resonant actuator, and a piezoelectric transducer.

9. The audio source localization aid system of claim 6, wherein the first unit further comprises a first audio output device, wherein the first unit is a hearing aid operable to produce an amplified audio stream to the first ear according to sound received by the first microphone, wherein the second unit further comprises a second audio output device, and wherein the second unit is a hearing aid operable to produce an amplified audio stream to the second ear according to sound received by the second microphone.

10. The audio source localization aid system of claim 9, further comprising a third microphone and a fourth microphone, wherein the processor is configured to determine source location information of sound received by the audio source localization aid system based on sound received by the first, second, third, and fourth microphones.

11. The audio source localization aid system of claim 10, wherein the processor is configured to determine a three-dimensional direction, relative to the head of the user, of the sound received by the audio source localization aid system.

12. The audio source localization aid system of claim 6, wherein the audio source localization aid system is operable to produce a tactile sensation indicative of a direction at a left ear of a user in response to sound received from the left side of the head of the user, and wherein the audio source localization aid system is operable to produce a tactile sensation indicative of a direction at a right ear of a user in response to sound received from the right side of the head of the user.

13. The audio source localization aid system of claim 12, wherein the audio source localization aid system is operable to simultaneously produce a tactile sensation indicative of a direction at both a left ear of a user and a right ear of a user in response to sound received from behind the head of the user.

14. The audio source localization aid system of claim 12, wherein the first tactile output device is a vibrator that comprises at least one of an eccentric rotating mass vibration motor, a linear resonant actuator, and a piezoelectric transducer, and wherein the second tactile output device is a vibrator that comprises at least one of an eccentric rotating mass vibration motor, a linear resonant actuator, and a piezoelectric transducer.

15. The audio source localization aid system of claim 6, wherein a frequency of the tactile output from at least one of the first and second tactile output devices is a function of the elevation of the source location relative to the head of the user.

16. The audio source localization aid system of claim 6, wherein the audio source localization aid system is operable to produce a tactile output in response to a sound that is a predetermined level above the ambient level of sound at a user of the audio source localization aid system.

17. The audio source localization aid system of claim 6, wherein the audio source localization aid system is operable to produce a tactile output in response to a sound that is selected from a plurality of preprogrammed sounds.

18. A method for operating a hearing aid system, the method comprising:
receiving an audio event at a first microphone of a first unit being worn by a user proximate to a first ear of the user;
receiving the audio event at a second microphone of a second unit being worn by the user proximate to a second ear of the user;
calculating a direction of a source of the audio event based at least in part on the receiving at the first microphone and the receiving at the second microphone;
producing a tactile output at at least one of the first unit and the second unit that is representative of the calculated direction of the source of the audio event, wherein a frequency and power level of the tactile output representative of the calculated direction of the source of the audio event is independent of the frequency and power level of the audio event; and
producing amplified sound by at least one of the first unit and the second unit during the first receiving step, second receiving step, calculating step, and producing step.

* * * * *